ID

US009198914B2

(12) United States Patent
Connell et al.

(10) Patent No.: US 9,198,914 B2
(45) Date of Patent: Dec. 1, 2015

(54) METHODS AND COMPOSITIONS FOR MODULATING RAD51 AND HOMOLOGOUS RECOMBINATION

(71) Applicant: The University of Chicago, Chicago, IL (US)

(72) Inventors: Philip P. Connell, Chicago, IL (US); Douglas K. Bishop, Chicago, IL (US); Ralph R. Weichselbaum, Chicago, IL (US)

(73) Assignee: The University of Chicago, Chicago, IL (US)

( * ) Notice: Subject to any disclaimer, the term of this patent is extended or adjusted under 35 U.S.C. 154(b) by 38 days.

(21) Appl. No.: 14/074,395

(22) Filed: Nov. 7, 2013

(65) Prior Publication Data

US 2014/0142103 A1 May 22, 2014

Related U.S. Application Data

(62) Division of application No. 12/671,147, filed as application No. PCT/US2008/071364 on Jul. 28, 2008, now Pat. No. 8,597,949.

(60) Provisional application No. 60/952,565, filed on Jul. 30, 2007, provisional application No. 60/972,593, filed on Sep. 14, 2007, provisional application No. 61/024,497, filed on Jan. 29, 2008, provisional application No. 61/024,513, filed on Jan. 29, 2008.

(51) Int. Cl.
| | |
|---|---|
| *A61K 31/535* | (2006.01) |
| *A61K 31/5377* | (2006.01) |
| *A61K 31/00* | (2006.01) |
| *A61K 31/18* | (2006.01) |
| *A61K 31/415* | (2006.01) |
| *A61K 31/4178* | (2006.01) |
| *A61K 31/4406* | (2006.01) |
| *A61K 31/4409* | (2006.01) |
| *A61K 45/06* | (2006.01) |

(52) U.S. Cl.
CPC .............. *A61K 31/5377* (2013.01); *A61K 31/00* (2013.01); *A61K 31/18* (2013.01); *A61K 31/415* (2013.01); *A61K 31/4178* (2013.01); *A61K 31/4406* (2013.01); *A61K 31/4409* (2013.01); *A61K 45/06* (2013.01)

(58) Field of Classification Search
USPC ................ 435/455, 375; 514/235.5
See application file for complete search history.

(56) References Cited

U.S. PATENT DOCUMENTS

| | | | |
|---|---|---|---|
| 6,090,539 | A | 7/2000 | Haaf ................................ 435/4 |
| 6,719,520 | B2* | 4/2004 | Coghlan et al. ............... 514/425 |
| 2003/0157693 | A1 | 8/2003 | Verdin et al. ............... 435/235.1 |
| 2003/0229004 | A1 | 12/2003 | Zarling et al. .................... 514/1 |

FOREIGN PATENT DOCUMENTS

| | | |
|---|---|---|
| EP | 1 731 609 | 12/2006 |
| WO | WO 03/013488 | 2/2003 |
| WO | WO 2004/097426 | 11/2004 |
| WO | WO 2007/120726 | 10/2007 |
| WO | WO 2008/022171 | 2/2008 |

OTHER PUBLICATIONS

Bishop et al., "Xrcc3 is required for assembly of Rad51 complexes in vivo," *J. Biol. Chem.*, 273:21482-21488, 1998.
Burgeev et al., Ca2+ activates human homologous recombination protein Rad51 by modulating its ATPase activity, *PNAS*, 101(27):9988-9993, 2004.
Caldecott and Jeggo, "Cross-sensitivity of gamma-ray-sensitive hamster mutants to cross-linking agents," *Mutat. Res.*, 255:111-121, 1991.
Chen et al., "Expression of BRC repeats in breast cancer cells disrupts the BRCA2-RAD51 complex and leads to radiatoin hypersensitivity and loss of $G_2$/M checkpoint control," *J. Biol. Chem.*, 274(46):32931-32935, 1999.
Chen et al., "The BRC repeats in BRCA2 are critical for RAD51 binding and resistance to methyl methanesulfonate treatment," *Proc. Natl. Acad. Sci. USA*, 95:5287-5292, 1998.
Collis et al., "Ribozyme minigene-mediated RAD51 down-regulation increases radiosensitivity of human prostate cancer cells," *Nucleic Acids Res.*, 29:1534-1538, 2001.
Cui et al., "The XRCC2 and XRCC3 repair genes are required for chromosome stability in mammalian cells," *Mutat. Res.*, 434:75-88, 1999.

(Continued)

*Primary Examiner* — Shirley V Gembeh
(74) *Attorney, Agent, or Firm* — Norton Rose Fulbright US LLP

(57) ABSTRACT

The present invention concerns methods and compositions involving inhibitors and enhancers of RAD51, a protein involved in homologous recombination. In some embodiments, the present invention concerns methods for stimulating homologous recombination, which has a number of significant research and clinical applications. In certain other embodiments, there are methods for protecting cells using a compound that enhances RAD51 activity. Such enhancers may also be employed to prevent or reduce damage to cells that may be caused by DNA damaging agents. In other embodiments, there are methods for sensitizing cells to the effects of DNA damaging agents, which can have particular applications for cancer patients. In some embodiments of the invention, the RAD51 enhancer or inhibitor is a small molecule that directly affects RAD51 activity, such as its ability to promote filament formation.

20 Claims, 41 Drawing Sheets

(56) References Cited

OTHER PUBLICATIONS

Davies et al., "Role of BRCA2 in control of the RAD51 recombination and DNA repair protein," *Mol. Cell*, 7:273-282, 2001.
Ellouze et al., "Difference between active and inactive nucleotide cofactors in the effect on the DNA binding and the helical structure of RecA filament : Dissociation of RecA—DNA complex by inactive nucleotides," *Eur. J. Biochem.*, 262(1):88-94, 1999.
Esashi et al., "CDK-dependent phosphorylation of BRCA2 as a regulatory mechanism for recombinational repair," *Nature*, 434:598-604, 2005.
Fuller and Painter, "A Chinese hamster ovary cell line hypersensitive to ionizing radiation and deficient in repair replication," *Mutat. Res.*, 193:109-121, 1988.
Gasior et al., "Assembly of RecA-like recombinases: distinct roles for mediator proteins in mitosis and meiosis," *Proc. Natl. Acad. Sci. USA*, 98:8411-8418, 2001.
Godthelp et al., "Mammalian Rad51C contributes to DNA cross-link resistance, sister chromatid cohesion and genomic stability," *Nucleic Acids Res.*, 30:2172-2182, 2002.
Han et al., "Accelerated screening of phage-display output with alkaline phosphatase fusions," *Comb. Chem. High Throughput Screen*, 7:55-62, 2004.
Han et al., "Identification of differentially expressed genes in pancreatic cancer cells using cDNA microarray," *Cancer Res.*, 62:2890-2896, 2002.
Hansen et al., "The role of RAD51 in etoposide (VP16) resistance in small cell lung cancer," *Int. J. Cancer*, 105:472-479, 2003.
Henning and Sturzbecher, "Homologous recombination and cell cycle checkpoints: Rad51 in tumour progression and therapy resistance," *Toxicology*, 193:91-109, 2003.
Hiendleder, "Mitochondrial DNA inheritance after SCNT," *Adv. Exp. Med. Biol.*, 591:103-16, 2007.
International Preliminary Report on Patentability, issued in International Application No. PCT/US2008/071364, dated Feb. 2, 2010.
International Search Report and Written Opinion, issued in International Application No. PCT/US2008/071364, dated Feb. 23, 2009.
Ishibashi et al., "Nonhomologous chromosomal integration of foreign DNA is completely dependent on MUS-53(human Lig4 homolog) in Neurospora," *PNAS*, 103(40):14871-14876, 2006.
Ishida et al., "DIDS, a chemical compound that inhibits RAD51-mediated homologous pairing and strand exhange," *Nucleic Acids Research*, 37(10):3367-3376, 2009.
Ito et al., "Rad51 siRNA delivered by HVJ envelope vector enhances the anti-cancer effect of cisplatin," *J. Gene Med.*, 7(8):1044-1052, 2005.
Jayathilaka et al., "A chemical compound that stimulates the human homologous recombination protein RAD51," *PNAS*, 105(41):15848-15853, 2008.
Jayathilaka et al., "Identification of a small molecule that stimulates human RAD51 protein," *Int. J. Radiation Oncology, Biology, Physics*, vol. 69, No. 3, Supplement, p. S598, Abstract #2719, 2007.
Jayathilaka, et al., *PNAS* 105(41):15848-15853, 2008.
Kim et al., "Effect of ions and nucleotides on the interactions of yeast Rad51 protein with single-stranded oligonucleotides," *J. Biochem.* (Tokyo), 129:469-475, 2001.
Lee et al., "A complementary pair of rapid molecular screening assays for RecA activities," *Analytical Biochemistry*, 367:247-258, 2007.
Liu et al., "Involvement of Rad51C in two distinct protein complexes of Rad51 paralogs in human cells," *Nucleic Acids Res.*, 30:1009-1015, 2002.
Liu et al., "XRCC2 and XRCC3, new human Rad51-family members, promote chromosome stability and protect against DNA cross-links and other damages," *Mol. Cell*, 1:783-793, 1998.
Maacke et al., "Autoantibodies in sera of pancreatic cancer patients identify recombination factor Rad51 as a tumour-associated antigen," *J. Cancer Res. Clin. Oncol.*, 128:219-222, 2002.
Maacke et al., "DNA repair and recombination factor Rad51 is overexpressed in human pancreatic adenocarcinoma," *Oncogene*, 19:2791-2795, 2000.
Maacke et al., "Over-expression of wild-type Rad51 correlates with histological grading of invasive ductal breast cancer," *Int. J. Cancer*, 88:907-913, 2000.
Masson et al., "Complex formation by the human RAD51C and XRCC3 recombination repair proteins," *Proc. Natl. Acad. Sci. USA*, 98:8440-8446, 2001.
Masson et al., "Identification and purification of two distinct complexes containing the five RAD51 paralogs," *Genes Dev.*, 15:3296-3307, 2001.
Moynahan et al., "BRCA2 is required for homology-directed repair of chromosomal breaks," *Mol. Cell*, 7:263-272, 2001.
Ohnishi et al., "In vitro and in vivo potentiation of radiosensitivity of malignant gliomas by antisense inhibition of the RAD51 gene," *Biochem. Biophys. Res. Commun.*, 245:319-324, 1998.
Pellegrini et al., "Insights into DNA recombination from the structure of a RAD51-BRCA2 complex," *Nature*, 420:287-293, 2002.
Qiao et al., "High-level expression of Rad51 is an independent prognostic marker of survival in non-small-cell lung cancer patients," *Br. J. Cancer*, 93:137-143, 2005.
Qui et al., "Stereoselective synthesis of chiral IBR2 analogues," *J. Org. Chem.*, 74:2018-2027, 2009.
Raderschall et al., "Elevated levels of Rad51 recombination protein in tumor cells," *Cancer Res.*, 62:219-225, 2002.
Russell et al., "Gleevec-mediated inhibition of Rad51 expression and enhancement of tumor cell radiosensitivity," *Cancer Res.*, 63:7377-7383, 2003.
Shin et al., "Full-length archaeal Rad51 structure and mutants: mechanisms for RAD51 assembly and control by BRCA2," *Embo. J.*, 22:4566-4576, 2003.
Shinohara et al., "Rad51 protein involved in repair and recombination in *S. cerevisiae* is a RecA-like protein," *Cell*, 69:457-470, 1992.
Takata et al., "Chromosome instability and defective recombinational repair in knockout mutants of the five Rad51 paralogs," *Mol. Cell Biol.*, 21:2858-2866, 2001.
Tebbs et al., "Correction of chromosomal instability and sensitivity to diverse mutagens by a cloned cDNA of the XRCC3 DNA repair gene," *Proc. Natl. Acad. Sci. USA*, 92:6354-6358, 1995.
Thompson and Schild, "Homologous recombinational repair of DNA ensures mammalian chromosome stability," *Mutat. Res.*, 477:131-153, 2001.
Thompson and Schild, "The contribution of homologous recombination in preserving genome integrity in mammalian cells," *Biochimie.*, 81:87-105, 1999.
Wachters et al., "Selective targeting of homologous DNA recombatyion repair by gemcitabine," *Int. J. of Radiation Oncology, Biology, Physics*, 57(2):553-562, 2003.
Wang et al., "Caffeine inhibits homology-directed repair of I-SceI-induced DNA double-stranded breaks," *Oncogene*, 23(3):824-834, 2004.
Wiese et al., "Interactions involving the Rad51 paralogs Rad51C and XRCC3 in human cells," *Nucleic Acids Res.*, 30:1001-1008, 2002.
Wittung et al., "Thermochemical and kinetic evidence for nucleotide-sequence-dependent RecA-DNA interactions," *Eur. J. Biochem.*, 245:715-719, 1997.
Wong et al., "RAD51 interacts with the evolutionarily conserved BRC motifs in the human breast cancer susceptibility gene brca2," *J. Biol. Chem.*, 272:31941-31944, 1997.
Yoshikawa et al., "Abnormal expression of BRCA1 and BRCA 1-interactive DNA-repair proteins in breast carcinomas," *Int. J. Cancer*, 88:28-36, 2000.
Yu et al., "Dynamic control of Rad51 recombinase by self-association and interaction with BRCA2," *Mol. Cell*, 12:1029-1041, 2003.
Yuan et al., "BRAC2 is required for ionizing radiation-induced assembly of Rad51 complex in vivo," *Cancer Res.*, 59:3547-3551, 1999.
Zaitseva et al., "The DNA binding properties of *Saccharomyces cerevisiae* Rad51 protein," *J. Biol. Chem.*, 274:2907-2915, 1999.
Zhang et al., "A Simple Statistical Parameter for Use in Evaluation and Validation of High Throughput Screening Assays," *J. Biomol. Screen*, 4:67-73, 1999.

\* cited by examiner 5253121 (also called compound 45488, or RS-1)

5914853

5917713

5916200

7907350

5916303

7985232

5350615

5921419

5525541

7935080

7942414

7954461

5917607

7989470

5319265

7956290

5922054

7930070

7977308

7937621

43783 (also called 5784166, or RS-2)

41936 (also called 7194, 5574720, or RS-3)

5207433   3092261   1144169

| Structure | Mol ID | ID | Formula | MW | Plate location |
|---|---|---|---|---|---|
| 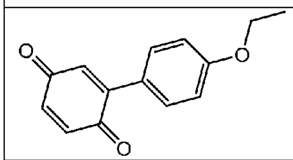 | 3939 | 5406172 | $C_{14}H_{12}O_3$ | 228.243 | 47693 |
| 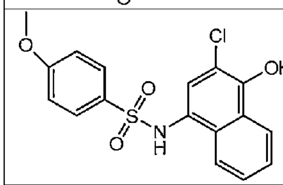 | 6068 | 5541102 | $C_{17}H_{14}ClNO_4S$ | 363.815 | 49872 |
| 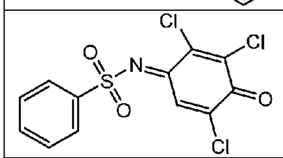 | 229 | 5158512 | $C_{12}H_6Cl_3NO_3S$ | 350.605 | 45264 |
| 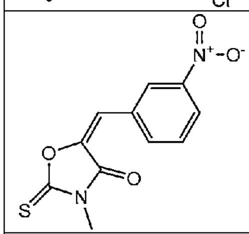 | 241 | 5162490 | $C_{11}H_8N_2O_4S$ | 264.257 | 45268 |
| 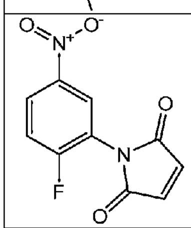 | 3479 | 5375199 | $C_{10}H_5FN_2O_4$ | 236.156 | 47283 |
| 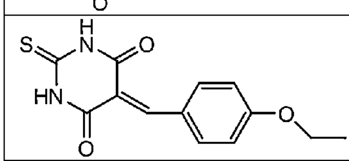 | 2714 | 5337665 | $C_{13}H_{12}N_2O_3S$ | 276.311 | 46762 |
| 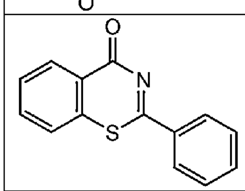 | 6366 | 5549187 | $C_{14}H_9NOS$ | 239.292 | 49735 |

| Structure | | | | | |
|---|---|---|---|---|---|
| 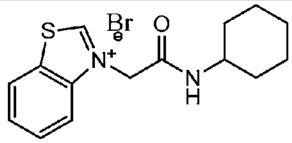 | 2990 | 5349209 | $C_{15}H_{19}BrN_2OS$ | 355.293 | 52098 |
| 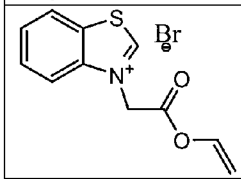 | 2850 | 5344209 | $C_{11}H_{10}BrNO_2S$ | 300.172 | 52051 |
| 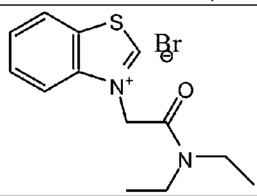 | 2905 | 5346214 | $C_{13}H_{17}BrN_2OS$ | 329.256 | 52072 |
| 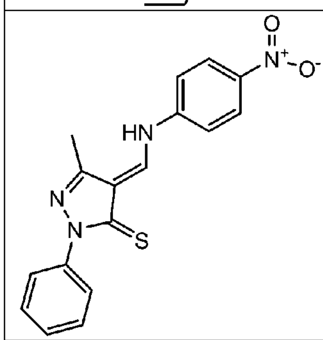 | 1658 | 5304192 | $C_{17}H_{14}N_4O_2S$ | 338.384 | 44867 |
| 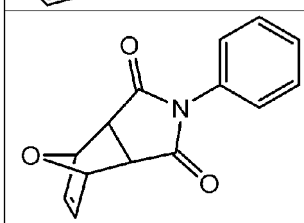 | 3576 | 5378138 | $C_{14}H_{11}NO_3$ | 241.242 | 474112 |
| 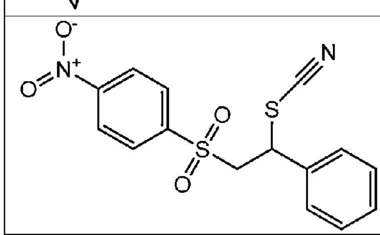 | 463 | 5218498 | $C_{15}H_{12}N_2O_4S_2$ | 348.397 | 50986 |

| | 2221 | 5318481 | $C_{19}H_{16}N_2O_4$ | 336.341 | 46147 |
|---|---|---|---|---|---|
|  | | | | | |
|  | 2893 | 5345879 | $C_{13}H_{12}BrNO_2$ | 294.144 | 46967 |
|  | 3560 | 5376628 | $C_{15}H_{13}NO_3$ | 255.269 | 47455 |
|  | 4916 | 5480050 | $C_{14}H_6N_2O_6$ | 298.207 | 52458 |
|  | 3578 | 5378298 | $C_{14}H_{10}BrNO_3$ | 320.138 | 474114 |
|  | 5040 | 5483251 | $C_{15}H_9ClN_2O_3S$ | 332.762 | 487114 |
|  | 5316 | 5510034 | $C_{17}H_{14}N_2O$ | 262.306 | 48786 |
|  | 7504 | 5612286 | $C_{15}H_{13}NO_4$ | 271.268 | 53498 |

FIG. 9D

| Structure | | | | | |
|---|---|---|---|---|---|
| (4-methylpyridin-2-yl-imino-methyl-naphthol structure) | 5317 | 5510037 | $C_{17}H_{14}N_2O$ | 262.306 | 48787 |
| (4-chlorophenyl nitrone of hydroxybenzaldehyde) | 6294 | 5547305 | $C_{13}H_{10}ClNO_2$ | 247.677 | 49768 |
| (6-methylpyridin-2-yl-imino-methyl-naphthol structure) | 5315 | 5510029 | $C_{17}H_{14}N_2O$ | 262.306 | 48785 |
| (benzothiazolium methyl 4-nitrobenzyl iodide structure) | 3044 | 5350986 | $C_{15}H_{13}IN_2O_2S$ | 412.245 | 47054 |
| (naphthol-imine-methylbenzimidazole-Br structure) | 1645 | 5303988 | $C_{19}H_{14}BrN_3O$ | 380.238 | 44862 |
| (bromonaphthol-imine-benzothiadiazole structure) | 1817 | 5308753 | $C_{17}H_{10}BrN_3OS$ | 384.25 | 46062 |
| (ethyl-methyl-phenyl-triazolidine-thione structure) | 3819 | 5404697 | $C_{11}H_{15}N_3S$ | 221.322 | 412103 |

| ChemBridge Compound ID | Structure |
|---|---|
| 5404694 | 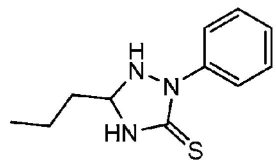 |
| 5792605 | 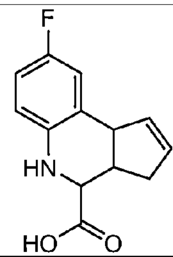 |
| 5318527 | 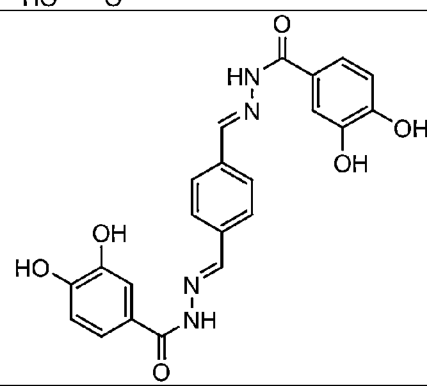 |
| 5404698 | 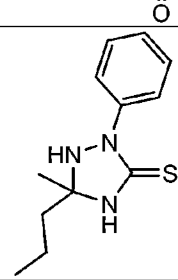 |
| 5373654 | 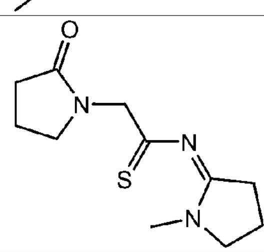 |
| 5343926 | 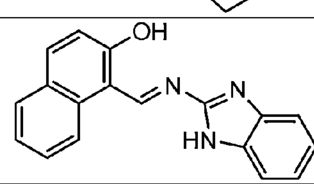 |

FIG. 9F

| ID | Structure |
|---|---|
| 5223737 | (phenyl-thiazole hydrazone benzylidene structure) |
| 5241203 | (piperidine-2,4,6-trione with ethoxyphenyl and nitrobenzylidene substituents) |
| 5404701 | (isobutyl-phenyl-triazolidine-thione structure) |
| 5304849 | (bis-trifluoromethyl propanamide linked to sulfamoylphenyl) |
| 5478849 | (carboxylic acid-substituted cyclopenta[c]quinoline with 2-chlorophenyl) |
| 5780801 | (4-methylpiperazine ethyl linked to methyl-furan) |

FIG. 9G

| 5240838 | |
| --- | --- |
| 5660163 | |
| 5691558 | |
| 5481902 | |
| 5404719 | |
| 5148736 | |
| 5343437 | |

FIG. 9H

| | |
|---|---|
| 5934813 | |
| 5316206 | |
| 5349669 | |
| 5193678 | |
| 5344003 | |
| 5376236 | |
| 5354404 | |
| 5285287 | |

| | |
|---|---|
| 5278811 |  |
| 5343472 |  |
| 5570197 |  |
| 5318477 |  |
| 5932095 |  |
| 5145339 |  |
| 5935565 |  |

FIG. 9J

| | |
|---|---|
| 5792001 | |
| 5615259 | |
| 5374241 | |
| 5475440 | |
| 5474807 | |
| 5347130 | |
| 5349054 | |

| 5347498 |  |
|---------|---|
| 5374218 | |

5681157

5748106

5667306

5784196

5784308

5785015

5787061

5784166

5784207

5784307

5751959

METHODS AND COMPOSITIONS FOR MODULATING RAD51 AND HOMOLOGOUS RECOMBINATION

This application is a divisional of co-pending U.S. patent application Ser. No. 12/671,147 filed May 19, 2010, which is a national phase application under 35 U.S.C. §371 of International Application No. PCT/US2008/071364 filed Jul. 28, 2008, which claims priority to U.S. Provisional Application No. 60/952,565 filed on Jul. 28, 2007, U.S. Provisional Patent Application 60/972,593 filed on Sep. 14, 2007, U.S. Provisional Patent Application 61/024,497 filed on Jan. 29, 2008, and U.S. Provisional Application No. 61/024,513 filed on Jan. 29, 2008, each of which is hereby incorporated by reference in its entirety.

BACKGROUND OF THE INVENTION

1. Field of the Invention

The present invention relates generally to the fields of biochemistry, cell biology, and oncology. More specifically, it concerns methods for modulating RAD51 protein activity in a cell.

2. Description of Related Art

Homologous recombination (HR) has multiple roles in DNA repair including the repair of DNA double-strand breaks (DSBs) and recovery from the replication blocking lesions formed by DNA cross-linking agents. HR repairs DSBs by locating a homologous stretch of DNA and replicating the missing genetic information from the homologous template. In contrast to repair by non-homologous end joining (NHEJ), DSB repair by HR generally occurs without mutations (Thompson and Schild, 2001). Numerous studies have also shown HR to be critically important in the maintenance of genomic stability (Thompson and Schild, 2001; Godthelp et al., 2002; Tebbs et al., 1995; Takata et al., 2001; Liu et al., 2002; Cui et al., 1999; Thompson and Schild, 1999). The proposed mechanism for this pathway begins with 5' to 3' nuclease activity at the DSB, resulting in a 3' single stranded tail (FIG. 1). The tail is coated by Replication Protein A (RPA), which is subsequently replaced by a helical filament of RAD51 protein. This displacement of RPA by RAD51 appears to be mediated by a number of protein complexes, which include RAD52 and a family of RAD51 paralog proteins (Thompson and Schild, 2001; Gasior et al., 2001). These RAD51 filaments can be microscopically visualized with fluorescent antibodies, and they appear as sub-nuclear foci (Bishop et al., 1998). The RAD51 coated 3' tail then invades a double stranded stretch of homologous template DNA. The genetic code is essentially copied from this template by polymerase activity and branch migration, in a structure termed the Holliday junction.

In addition to RAD51, repair via HR requires five RAD51 paralog proteins. The paralogs form two complexes in solution, a XRCC3/RAD51C heterodimer and a RAD51B/RAD51C/RAD51/XRCC2 heterotetramer (Liu et al., 2002; Masson et al., 2001a; Masson et al., 2001b; Wiese et al., 2002). Mutation of any one of the five paralog genes prevents subnuclear assembly of recombinase at damaged sites and reduces the cell's ability to perform HR repair (Godthelp et al., 2002; Tebbs et al., 1995; Takata et al., 2001; Bishop et al., 1998; Fuller and Painter, 1988; Caldecott and Jeggo, 1991; Liu et al., 1998). These paralogs are thought to serve as assembly 'mediators' for RAD51. RPA can inhibit assembly of RAD51 recombinase at sites of damage, and mediator proteins are thought to help overcome this inhibition. Studies have demonstrated a sensitization to certain DNA damaging therapies associated with cellular defects in proteins that promote HR DNA repair. This sensitization is particularly dramatic for DNA cross-linking chemotherapeutic drugs (30-100 times) and ionizing radiation (3-5 times) (Godthelp et al., 2002; Tebbs et al., 1995; Takata et al., 2001; Liu et al., 1998).

Several groups have recently demonstrated that HR can be partially inhibited in order to sensitize cells to DNA damaging therapies. Inhibition of XRCC3 (a RAD51 paralog protein), has been demonstrated using a synthetic peptide corresponding to another paralog protein. This peptide sensitized Chinese Hamster Ovary (CHO) cells to cisplatin and inhibited the formation of sub-nuclear RAD51 foci in response to DNA damage (Connell et al., 2004). Other researchers have inhibited the expression of the RAD51 protein itself (Russell et al., 2003; Hansen et al., 2003; Ohnishi et al., 1998; Ito et al., 2005; Collis et al., 2001) or blocked its function by over-expressing a dominant negative BRC peptide fragment derived from BRCA2 (Chen et al., 1999).

In view of the connection between increased sensitivity to certain DNA damaging therapies and cellular defects in HR DNA repair-related proteins, methods and compounds that provide for selective manipulation of this balance are desirable.

SUMMARY OF THE INVENTION

The present invention is based on the identification and characterization of compounds that alter the ability of the RAD51 protein to bind fluorescently labeled oligonucleotides. Therefore, the present invention concerns methods and compositions involving compounds that directly modulate the activity of the RAD51 protein. In certain embodiments, methods and compositions concern compounds that modulate RAD51 activity by increasing, enhancing, or stimulating RAD51 activity. In other embodiments, methods and compositions concern compounds that modulate RAD51 activity by decreasing, inhibiting, or reducing RAD51 activity.

In certain embodiments, there are methods for modulating a RAD51 protein in a cell comprising providing to the cell an effective amount of a RAD51 protein modulator, wherein the modulator is a small molecule that directly modulates the activity of RAD51 protein. This means that small molecules of the invention alter the activity of RAD51 protein (or a RAD51 protein analog or homolog) directly (i.e., RAD51 activity increases when the RAD51 protein is contacted or incubated with the small molecule), and not indirectly, such as by altering the expression level of RAD51.

In some embodiments of the invention, methods and compositions concern a compound that is a RAD51 enhancer, meaning that the compound directly increases, enhances, and/or stimulates RAD51 protein activity when the RAD51 protein is exposed to the compound. The terms "enhancer" and "stimulator" are used interchangeably herein. In particular embodiments, the RAD51 enhancer increases RAD51 filament formation when the enhancer is incubated with RAD51 protein and nucleic acid molecules under conditions to promote filament formation. In certain other embodiments, the RAD51 enhancer increases or stimulates homologous recombination via RAD51 in a cell. In even further embodiments, the RAD51 enhancer prevents or reduces damage to DNA in a cell. In additional embodiments, the RAD51 enhancer prevents or reduces cell death insofar as RAD51 activity can contribute to that effect. The present invention also concerns embodiments in which a RAD51 enhancer prevents or reduces mutations in a cell.

Therefore, the present invention is contemplated to cover a number of methods involving a RAD51 enhancer, which may increase, enhance or stimulate a RAD51 activity by or by at least 10, 15, 20, 25, 30, 35, 40, 45, 50, 55, 60, 65, 70, 75, 80, 85, 90, 95, 100% or more (and any range derivable therein) compared to RAD51 activity in the absence of the RAD51 enhancer. In certain embodiments there are methods for increasing RAD51 activity in a cell involving providing to the cell an effective amount of a RAD51 enhancer.

Some embodiments of the invention involve methods for preventing or reducing DNA damage in cells comprising providing to the cells an effective amount of a RAD51 enhancer, wherein the RAD51 enhancer directly increases RAD51 activity. In particular embodiments it is contemplated that the damage may be from a treatment such as chemotherapy or radiation or from environmental exposure to a DNA damaging agent. In some situations it is contemplated that the DNA damaging agent may be from an industrial accident or from a weapon, such as a bomb ("dirty bomb").

In certain embodiments, there are methods for stimulating homologous recombination in cells comprising providing to the cell an effective amount of a RAD51 enhancer that directly increases the activity of RAD51 or a RAD51 homolog in the cells.

In additional embodiments there are methods for reducing the incidence of mutations in a cell comprising providing to the cell an effective amount of a RAD51 enhancer such that the number of mutations is decreased. It is contemplated that some mutations may lead to genetic defects or birth defects and therefore, the present invention may be applied in the context of sex cells, fetal cells, and embryo cells. In some cases, the RAD51 enhancer could be provided to cells systemically.

In other embodiments, there are methods for incorporating exogenous DNA into cells' DNA comprising: a) transfecting the cells with a composition comprising the exogenous DNA; and, b) contacting the cells with an effective amount of a RAD51 enhancer.

The present invention also concerns methods for increasing the efficiency of gene therapy in a patient comprising administering gene therapy to the patient and an effective amount of a RAD51 enhancer that directly increases RAD51 activity.

In some embodiments it is contemplated that methods of the invention involving a RAD51 enhancer may be used for gene targeting (altering or deleting a gene through recombination using an exogenous sequence) or for gene conversion (nonreciprocal transfer of genetic information through recombination). Such embodiments may be implemented by introducing into a cell a nucleic acid that is to be used for the gene targeting or for the gene conversion and by exposing the cell to an effective amount of a composition comprising a RAD51 enhancer. In some embodiments involving gene targeting, the nucleic acid contains sequences adjacent to the sequence to be deleted (knocked out). In other embodiments the nucleic acid contains a sequence that an endogenous sequence will be converted to. In specific embodiments, the exogenous nucleic acid contains one or more mutations relative to an endogenous sequence. In other embodiments, the exogenous nucleic acid has a wild-type sequence relative to an endogenous sequence, and such methods can be used to correct genetic defects.

The present invention also covers methods in which homologous recombination is stimulated to alter genetic map distances, such as for improving the efficiency or resolution of gene mapping. In such situations a RAD51 enhancer can be employed. In other embodiments, it may be advantageous to inhibit homologous recombination so as to alter genetic map distances. A RAD51 inhibitor could be used for these types of situations.

Other embodiments involving the use of an effective amount of RAD51 enhancer to promote recombination within a cell that contains a heterologous nucleic acid sequence already incorporated in a cell's DNA. In some cases, the heterologous nucleic acid sequence has been incorporated into a random site in the DNA and this may be employed to re-position the heterologous sequence or better target it to a particular site. In particular embodiments, such methods may be employed in any variety of cells, including human cells or *Drosophila melanogaster* cells.

A RAD51 enhancer is a compound that acts in conjunction with RAD51 protein to increase, enhance, or stimulate the activity of the RAD51 protein. In certain embodiments the RAD51 enhancer is a small molecular weight compound. In specific embodiments, the RAD51 stimulator is a compound of formula (VII):

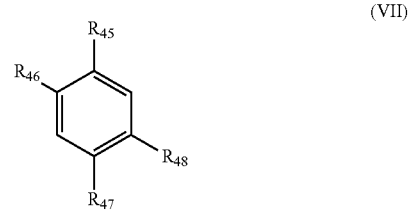

(VII)

or a salt thereof, wherein $R_{45}$ is H, —C(O)(CH$_2$)$_q$NH-aryl, —NHC(O)O-alkyl, or

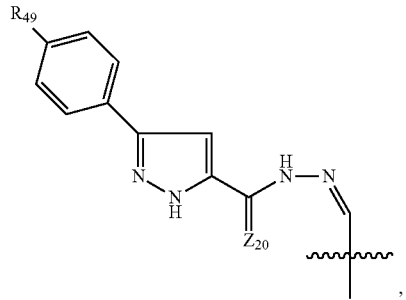

wherein $R_{49}$ is halogen or alkoxy; $Z_{20}$ is O or S; and q is 0-6; $R_{46}$ is H or halogen; $R_{47}$ is H, alkyl, hydroxy, or halogen; $R_{48}$ is H, hydroxy, or —SO$_2$NH(CH$_2$)$_r$-aryl, wherein r is 0-6; and $R_{50}$ is H or hydroxy. In certain embodiments, $R_{45}$ is —C(O)(CH$_2$)$_q$NH-aryl. In certain embodiments, q is 0. In certain embodiments, the aryl group is phenyl. In certain embodiments, the aryl group is mono-substituted phenyl. In certain embodiments, the mono-substituted phenyl is further defined as phenyl substituted at the para-position by a halogen. In certain embodiments, $R_{49}$ is alkoxy, such as methoxy or ethoxy. In certain embodiments $R_{45}$ is —NHC(O)O-alkyl. In certain embodiments, the alkyl group of —NHC(O)O-alkyl is a linear heteroatom-unsubstituted alkyl group (e.g., butyl) or a branched heteroatom-unsubstituted alkyl group (e.g., tert-butyl).

The RAD51 stimulator may, in certain embodiments, be selected from the compounds shown in FIGS. 8A-8E, or a salt thereof.

It is contemplated that derivatives, metabolites, and prodrugs of these compounds may also be used as RAD51 enhancers in some embodiments of the invention.

In addition, the present invention is contemplated to cover a number of methods involving a RAD51 inhibitor, which may decrease, inhibit or reduce a RAD51 activity by or by at least 10, 15, 20, 25, 30, 35, 40, 45, 50, 55, 60, 65, 70, 75, 80, 85, 90, 95, or 100% (and any range derivable therein) compared to RAD51 activity in the absence of the RAD51 inhibitor. Therefore, in some embodiments of the invention, there are methods for inhibiting RAD51 in a cell comprising providing to the cell an effective amount of a RAD51 small molecule that directly inhibits RAD51 activity in a cell.

In some embodiments, a RAD51 inhibitor decreases RAD51 filament formation. In further embodiments, the RAD51 inhibitor does not interact with a RAD51 DNA binding domain. In still further embodiments, the RAD51 inhibitor interferes with RAD51 ATPase activity.

In other embodiments of the invention, there are methods for protecting non-cancerous cells in a cancer patient comprising administering to the patient an effective amount of a RAD51 small molecule enhancer prior to being exposed to a DNA damaging agent.

Additional embodiments concern methods for sensitizing cancer cells to a DNA damaging agent comprising administering to a cancer patient an effective amount of a RAD51 small molecule that directly inhibits RAD51 activity in a cell. Other embodiments include methods for preventing or reducing DNA damage in a subject comprising administering to the subject an effective amount of RAD51 enhancer, wherein the enhancer directly increases the amount of RAD51 activity.

Other embodiments of the invention include methods for inhibiting conception or the use of compositions of the invention as contraceptives. Because homologous recombination is required for forming function of eggs and sperm, it is contemplated that RAD51 inhibitors can be used to reduce fertility of an individual by exposing the individual's sex cells to an effective amount of a RAD51 inhibitor.

An "effective amount" of a compound or composition, generally, is defined as that amount sufficient to detectably and repeatedly achieve the stated desired result, for example, to ameliorate, reduce, minimize or limit the extent of the disease or its symptoms or to increase, stimulate, or promote a desirable physiological response, such as homologous recombination. More rigorous definitions may apply, including elimination, eradication or cure of disease.

It is contemplated that in certain embodiments, a cell is a human cell and the subject or patient is a human patient. In other embodiments, a cell is a mammalian cell and the subject or patient is a mammalian patient. In some embodiments, a cell is a *Drosophila* cell and the subject or patient is a *Drosophila* patient. It will be understood that different mammals have their own RAD51 protein that would be a homolog of the human protein. In certain other embodiments, the cell is a eukaryotic cell, while in other embodiments, the cell is a prokaryotic cell and a RAD51 protein homolog or analog is the protein that is modulated. In specific embodiments, a cell may be a sex cell, while in others, the cell is a somatic cell. In particular embodiments, cells used in methods of the invention may be from a cell line. In certain embodiments, the cell is a cell from or in any organism described herein. Moreover, in some embodiments the cell is a cancer cell, while in other embodiments a cell is non-cancerous or normal. In some cases, a cancer cell is resistant to chemotherapy or radiation. Furthermore, it is contemplated that a cell can be in a patient. Additionally, a cell may be an embryonic stem (ES) cell, such as a murine ES cell, which are used for generating knockout mice. Alternatively, cells may be murine cells that are used for generating a transgenic mouse. Other transgenic animals can be generated using a particular animals cells in the context of methods of the invention.

Methods of the invention may involve a RAD51 inhibitor that is a small molecular weight compound. In certain embodiments, a RAD51 inhibitor is selected from the group consisting of: (a) a compound of the formula:

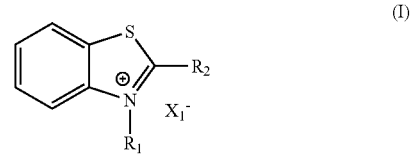

or a salt thereof, wherein $R_1$ is alkyl or a compound of formula (a):

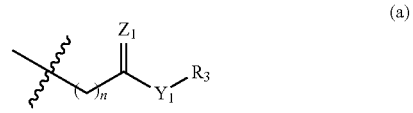

wherein $R_3$ is alkyl, alkenyl, or alkylamino; $Y_1$ is NH or O; $Z_1$ is O or S; and n is 1-5; $R_2$ is H, alkyl, or aralkyl; and $X_1$ is a monovalent anion; (b) a compound of the formula:

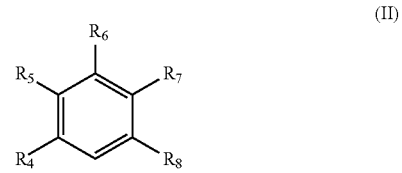

or a salt thereof, wherein $R_4$ is H, alkyl, alkoxy or halogen; $R_5$ is H or nitro; $R_6$ is H or alkyl; $R_7$ is H, alkyl, a compound of formula (b):

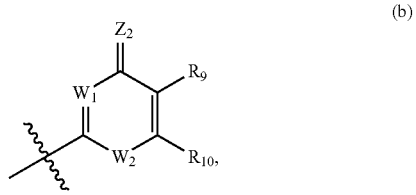

or a compound of formula (c):

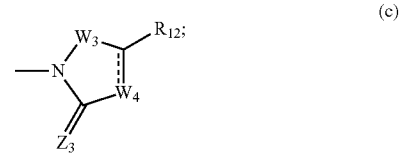

wherein R$_9$ and R$_{10}$ are each H or taken together form

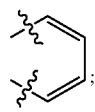

R$_{12}$ is H, alkyl, halogen, or taken together with W$_4$ forms

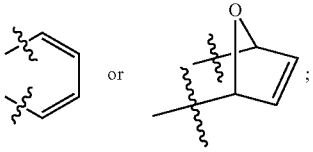

W$_1$-W$_4$ are each independently CH, CH$_2$, N, NH, or S; and Z$_2$-Z$_3$ are each independently S or O; and R$_8$ is H, alkyl, or halogen; (c) a compound of the formula:

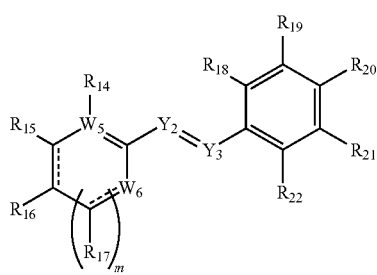

(III)

or a salt thereof, wherein R$_{14}$ is H or alkyl; R$_{15}$ is H, alkyl, or together with R$_{16}$ forms

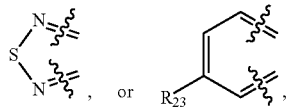

wherein R$_{23}$ is H or halogen; R$_{16}$ is H, alkoxy, hydroxy, or together with R$_{15}$ forms

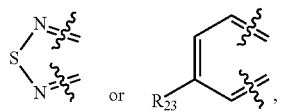

wherein R$_{23}$ is H or halogen; R$_{17}$ is H or alkyl; R$_{18}$ is H or together with R$_{19}$ forms

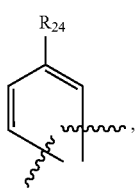

wherein R$_{24}$ is H or halogen; R$_{19}$ is H, halogen, or together with R$_{18}$ faints

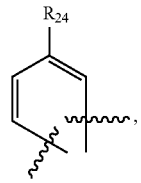

wherein R$_{24}$ is H or halogen; R$_{20}$ is H, alkyl, or hydroxy; R$_{21}$ is H or together with R$_{22}$ forms

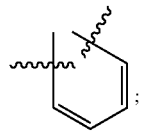 [SMILES: */C=C\C=C/*]

R$_{22}$ is H, hydroxy, or together with R$_{21}$ forms

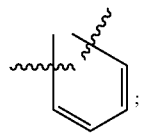 [SMILES: */C=C\C=C/*]

W$_5$ and W$_6$ are each independently CH, CH$_2$, N, NH, or alkylamino; Y$_2$ and Y$_3$ are each independently CH, N, N+-O$^-$, or SO$_2$; and m is 0 or 1; (d) a compound of the formula:

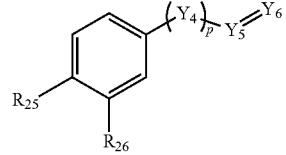

(IV)

or a salt thereof, wherein R$_{25}$ is H, alkoxy, or nitro; R$_{26}$ is H or nitro; Y$_4$ is SO$_2$ or NH; Y$_5$ is N or CH; Y$_6$ is

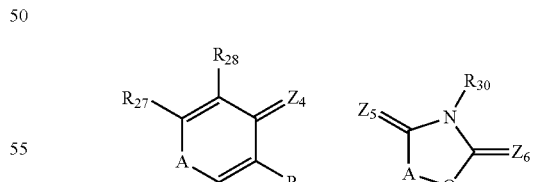

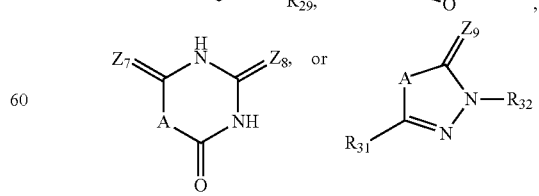

wherein the point of attachment of Y$_6$ to the double bond between Y$_5$ and Y$_6$ is at ring atom A; R$_{27}$-R$_{32}$ are each independently H, alkyl, aryl, or halogen; and $Z_4$—$Z_9$ are each independently O or S; and p is 0 or 1; (e) a compound of the formula:

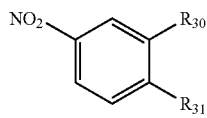
(V)

or a salt thereof, wherein $R_{30}$ is H,

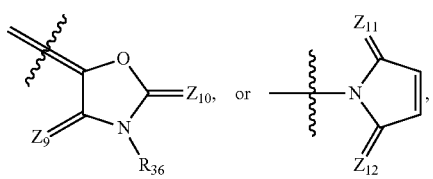

or $R_{30}$ taken together with $R_{31}$ forms the fused tricyclic structure

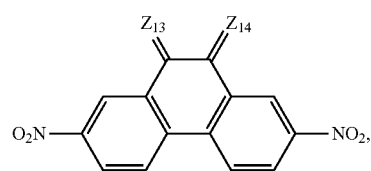

wherein $R_{36}$ is H or alkyl; and $Z_9$-$Z_{14}$ are each independently O or S; $R_{31}$ is H, halogen,

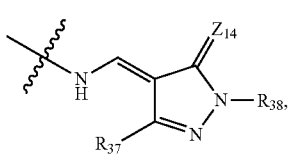

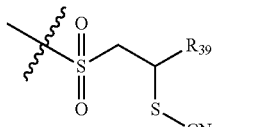

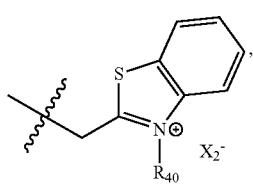

or $R_{31}$ taken together with $R_{30}$ forms the fused tricyclic structure

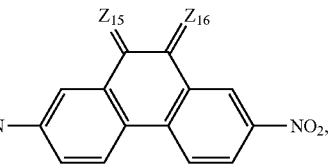

wherein $Z_{14}$-$Z_{16}$ are each independently O or S; $R_{37}$-$R_{40}$ are each independently H, alkyl, or aryl; and $X_2$ is a monovalent anion; (f) a compound of the formula:

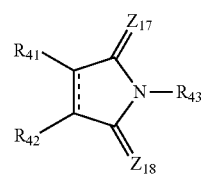
(VI)

or a salt thereof, wherein $R_{41}$ and $R_{42}$ are each independently H or halogen, or together form

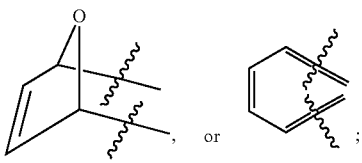 [SMILES: *C1C=CC(*)O1 ; *=C/C=C\C=*]

$R_{43}$ is aryl or

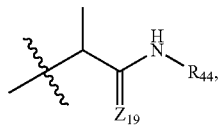

wherein $R_{44}$ is aryl; and $Z_{19}$ is O or S; and (g) a compound of formula (VIII):

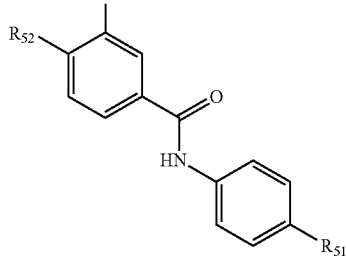
(VIII)

or a salt thereof, wherein $R_{51}$ and $R_{52}$ are each independently H or bromide, and t is 0 or 1, provided that: (i) when $R_{51}$ is H, then $R_{52}$ is bromide and t=1; (ii) when $R_{51}$ is Br and $R_{52}$ is H, then t=1; and (iii) when $R_{51}$ and $R_{52}$ are each bromide, then t=0.

In particular embodiments, a RAD51 inhibitor is selected from the compounds listed in FIGS. 9A-9K, or a salt thereof. It is contemplated that derivatives, metabolites, and pro-drugs of these compounds may also be used as RAD51 inhibitors in some embodiments of the invention.

In certain embodiments, the inhibitor is not a nucleotide diphosphate, a nucleotide analog, a DNA minor groove binding drug, a xanthine, or xanthine derivative. In particular embodiments, the RAD51 inhibitor does not bind to RAD51's DNA binding domain. In certain cases, the RAD51 inhibitor interacts with RAD51's ATPase domain.

The small molecules described herein typically contain an aryl group. Accordingly, in certain embodiments, compounds comprising one or more aryl groups are contemplated. The aryl groups may be substituted by any substituent known to those of skill in the art (e.g., H, amino, nitro, halo, mercapto, cyano, azido, silyl, hydroxy, alkyl, alkenyl, alkynyl, aryl, aralkyl, alkoxy, alkenoxy, alkynyloxy, aryloxy, acyloxy, alkylamino, alkenylamino, alkynylamino, arylamino, aralkylamino, amido, alkylthio, alkenylthio, alkynylthio, arylthio, aralkylthio, acylthio, alkylsilyl, phosphonate, phosphinate, or any combination thereof). Subsets of these substituent groups at any aryl position are also contemplated (e.g., compounds of formula I, II, III, IV, V, VI, VII, VIII, or any combination thereof). In certain embodiments, the small molecules are any one or more of the specific chemical compounds whose structures are shown herein.

In some embodiments, the present invention concerns methods involving a nucleic acid to be homologously recombined (exogenous DNA) with a cell's DNA (endogenous DNA). In some of these embodiments, method involve providing or administering to a cell a composition comprising a nucleic acid under conditions that promote homologous recombination of all or part of the nucleic acid with the cell's DNA. In some embodiments, all or part of the exogenous DNA is incorporated into the cell's endogenous DNA. It is contemplated that a cell's endogenous DNA may be chromosomal, episomal, mitochondrial, or nuclear, any of which may be homologously recombined with exogenous DNA.

In certain embodiments, the nucleic acid is in a vector. In specific embodiments the nucleic acid is in a DNA construct. In further embodiments, the DNA construct is a plasmid. It is specifically contemplated that methods of the invention may involve a nucleic acid, all or part of which may undergo homologous recombination with the host cell's DNA.

In certain embodiments, the nucleic acid is a therapeutic nucleic acid to be introduced into the cell's DNA. A "therapeutic nucleic acid" is defined herein to refer to a nucleic acid that is known or suspected to be of benefit in the treatment or prevention of a disease or health-related condition. For example, the "therapeutic nucleic acid" may be a nucleic acid that encodes a protein or polypeptide that is known or suspected to be of benefit in the treatment of a disease or health-related condition. Also included in the definition of "therapeutic nucleic acid" is a nucleic acid that transcribes a second nucleic acid that is known or suspected to be of benefit in the treatment of a disease or health-related condition (e.g., a DNA transcribed into ribozyme or siRNA). Alternatively, the "therapeutic nucleic acid" may be one which is known or suspected to provide for a therapeutic benefit without undergoing transcription (e.g., a siRNA or a ribozyme).

In other embodiments, the nucleic acid contains one or more alterations relative to the cell's endogenous DNA, wherein the alterations will be recombined into the cell's DNA. The alterations may be deletions, insertions, or substitutions of one or more nucleotide residues. An alteration may be a mutation, a wild-type sequence, or a polymorphism. Moreover, in some embodiments of the invention nucleic acids include sequences that allow for their presence to be readily detected or assayed. In certain embodiments, a nucleic acid contains a screenable or selectable marker.

It is contemplated that RAD51 enhancers may be employed in certain embodiments in the following methods: correction of mutations, induction of specific mutations, insertion of genes under the control of specific promoters, insertion of promoters to alter regulation of genes, creation of specific chromosome deletions and insertions, creation of specific translocations and inversions, increasing the expression of particular gene products, eliminating the expression of particular gene products, introduction of foreign coding regions to endow cells with novel functions, introduction of foreign coding regions to test the function of those regions in a foreign cell including complementation analysis, construction of fusion proteins that facilitate detection and purification of such proteins with or without their binding partners, construction of combinations of chromosome features to facilitate detection and measurement of biological processes such as transcription, replication, homologous recombination, and DNA-end-joining.

In certain specific embodiments, methods include "ends-in" DNA vector constructs that result in integration of vector circles into the chromosome after linearization in a region of homology. In other embodiments, methods involve "ends-out" linear constructs that promote "transplacement" of foreign sequences into chromosomes by recombination of homologous sequences at both ends of the linear construct. Methods discussed above can target a chromosome (previously unaltered or altered by gene targeting) It is also contemplated that these methods may allow targeting of an artificial chromosome or episome.

It is contemplated that nucleic acids may be introduced into cells (also known as transfection or transformation) by any method, many of which are well known to those of skill in the art, including (but not limited to), electroporation, chemical transformation (calcium phosphate), lipid transformation, particle bombardment, and microinjection.

In embodiments of the invention, methods may also involve determining whether recombination with all or part of the introduced nucleic acid molecule or sequence has occurred. In specific embodiments, this involves assaying the cells to determine whether the nucleic acid has been incorporated into the cell's nucleic acid.

Methods of the invention can be implemented as treatment for patients with cancer. The cancer may be any cancer treatable by administration of a compound described herein. In certain embodiments, a cancer may be treatable using a combination treatment involving a conventional DNA damaging agent with a RAD51 inhibitor. In some instances, the RAD51 inhibitor may be what allows a cancer to be treated with the DNA damaging agent. Methods of the invention can be implemented with any cancer that may be treated with a DNA damaging agent. For example, the cancer may be breast, prostate, ovarian, brain, melanoma, colorectal, liver, lymphoma, lung, oral, head, neck, spleen, lymph node, small intestine, large intestine, blood cells, stomach, pancreatic, endometrium, testicle, skin, esophagus, bone marrow, blood, cervical, bladder, Ewing's sarcoma, thyroid, a glioma, and/or gastrointestinal. The invention is applicable to other cancers discussed herein, including pre-cancers.

In embodiments of the invention, a cancer patient may have been treated with or will be treated with a DNA damaging agent. In related embodiments, a subject may have been exposed to a DNA damaging agent (as a harmful agent and not as part of a treatment) or be at risk for such exposure. It is contemplated that in some embodiments of the invention, the DNA damaging agent is an alkylating agent, nitrosourea, anti-metabolite, plant alkaloid, plant extract, or radioisotope. In specific embodiments, the DNA damaging agent is actinomycin, amsacrine, anthracyclines, bleomycin, busulfan, camptothecin, carboplatin, chlorambucil, cisplatin, cyclophosphamide, cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide or etoposide (VP16). Any other DNA damaging agent discussed herein may be implemented in methods of the invention. In certain embodiments, the DNA damaging agent is radiation.

Methods of the invention may involve multiple administrations of one or more compounds, compositions, and/or agents. In certain embodiments, cells or a subject are provided with a DNA damaging agent, a RAD51 modulator (RAD51 enhancer or inhibitor), and/or a nucleic acid 1, 2, 3, 4, 5, 6, 7, 8, 9, or 10 times or more (or any range derivable therein). It is contemplated that compounds, compositions, and/or agents may be formulated in a pharmaceutically acceptable formulation in certain embodiments of the invention.

Moreover, in methods of the invention the order in which things are provided to cells or a subject may vary. In some embodiments, a RAD51 modulator (RAD51 enhancer and/or RAD51 inhibitor) is provided prior to a nucleic acid being provided to a cell or subject. In other embodiments, a RAD51 modulator (RAD51 enhancer and/or RAD51 inhibitor) is provided simultaneously with a nucleic acid or after the nucleic acid is provided. It is contemplated that a RAD51 modulator (RAD51 enhancer and/or RAD51 inhibitor) may be provided to a cell or subject within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 33, 34, 35, 36, 37, 38, 39, 40, 41, 42, 43, 44, 45, 46, 47, 48 hours and/or 1, 2, 3, 4, 5, 6, or 7 days (or any range derivable therein) of the cell or subject being provided with a DNA damaging agent or an exogenous nucleic acid, and vice versa. In certain embodiments, a RAD51 modulator (RAD51 enhancer and/or RAD51 inhibitor) is provided before, during, and/or after a DNA damaging agent or an exogenous nucleic acid are provided. In specific embodiments, a RAD51 modulator (RAD51 enhancer and/or RAD51 inhibitor) is provided before, during, and/or after gene therapy is provided.

Methods of the invention can involve conferring a therapeutic benefit on a subject. A therapeutic benefit may arise, for example, as a result of alteration of expression of a particular gene or genes by the nucleic acid. Alteration of expression of a particular gene or genes may be inhibition or augmentation of expression of a particular gene. In particular embodiments of the present invention, the therapeutic nucleic acid encodes one or more proteins or polypeptides that can be applied in the treatment or prevention of a disease or health-related condition in a subject.

A "disease" is defined as a pathological condition of a body part, an organ, or a system resulting from any cause, such as infection, genetic defect, or environmental stress. A "health-related condition" is defined herein to refer to a condition of a body part, an organ, or a system that may not be pathological, but for which treatment is sought. Examples include conditions for which cosmetic therapy is sought, such as skin wrinkling, skin blemishes, and the like. The disease can be any disease, and non-limiting examples include hyperproliferative diseases such as cancer and premalignant lesions, wounds, and infections.

"Prevention" and "preventing" are used according to their ordinary and plain meaning to mean "acting before" or such an act. In the context of a particular disease or health-related condition, those terms refer to administration or application of an agent, drug, or remedy to a subject or performance of a procedure or modality on a subject for the purpose of blocking the onset of a disease or health-related condition.

The present invention also concerns screening methods for identifying or characterizing RAD51 modulators. In some embodiments there are high-throughput methods for screening RAD51 modulators comprising: a) combining a RAD51 protein with at least one test compound and fluorescently-labeled oligonucleotides under conditions to promote filament formation to form a filament formation composition; b) measuring the level of fluorescence polarization (FP). In certain embodiments, a human RAD51 protein is used. Additionally, some embodiments will involve a multi-well plate.

In some screening methods, a filament formation composition may contain or contain at least 0.1, 0.2, 0.3, 0.4, 0.5, 0.6, 0.7, 0.8, 0.9, 1.0, 2.0, 3.0, 4.0, 5.0 µM or more (or any range derivable therein) of RAD51 protein. In particular embodiments, RAD51 protein is purified.

Other conditions of the screening method can include a composition that comprises calcium ions. It is contemplated that in some embodiments the concentration of calcium ions in the composition is about, at least about, or at most about 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 10, 20, 30, 40, 50, 60, 70, 80, 90, 100 µM or more (or any range derivable therein).

The present invention also concerns kits and compositions having a RAD51 enhancer and a nucleic acid to be introduced into a cell. These kits are expected to facilitate homologous recombination between the nucleic acid and endogenous DNA.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIG. 2A, top: Schematic of protein filament formation monitored in vitro using a fluorescence polarization assay. FIG. 2A, bottom: Purified RAD51 protein (wild type or mutant F86E) were serially diluted. RecA (New England Biolabs) was used as a positive control. Proteins were added to a 5'terminal fluorescein conjugated oligonucleotide (45 bases of dT) at a 1 µM nucleotide concentration. The mixture was incubated at 37° C. for 30 minutes in 384-well plates containing a reaction buffer (30 mM Tris/acetate pH 7.5, 10 mM $Mg^{2+}$/acetate, 2 mM ATP, 0.1 mM DTT, 0.5 µM BSA). Fluorescence polarization was measured with a plate reader (filters: excitation=485 nm, emission=510 nm). FIG. 2B, top: Varying concentrations of 5'terminal fluorescein conjugated oligonucleotide were used to determine the threshold RAD51 concentration. FIG. 2B, bottom: Varying the buffer conditions shows that RAD51 filament formation is even more efficient in the presence of calcium ions.

FIGS. 9A-9K. Structures of various RAD51 inhibitors of the present invention.

DESCRIPTION OF ILLUSTRATIVE EMBODIMENTS

Figure 1:
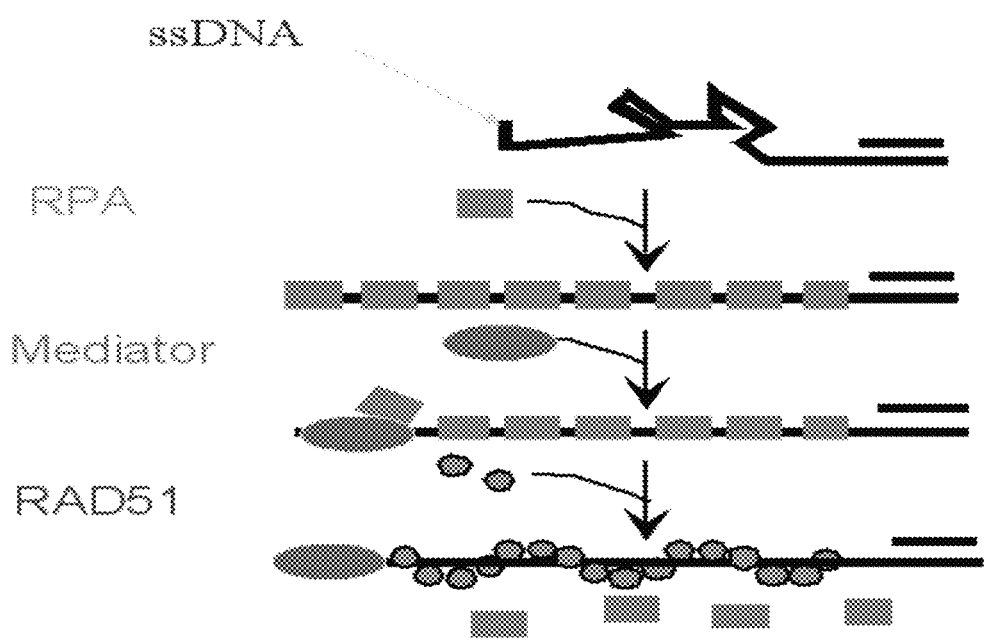
FIG. 1. Proposed mechanism for homologous recombinational DNA repair.

The present invention overcomes the deficiencies of the prior art by providing compounds that modulate the activity of a protein involved in homologous recombinational (HR) DNA repair, RAD51. As discussed above, HR DNA repair confers cellular resistance to ionizing radiation and certain DNA damaging agents. Pharmacologic manipulation of HR levels may be used to modulate this resistance. RAD51 is the central protein involved in the initiation of HR. Drugs that reduce RAD51 function could potentially be used to inhibit HR in cancer cells, thereby overcoming the resistance of malignant tumors to common oncologic therapies. Conversely, RAD51 enhancing agents could serve to transiently increase HR and/or bypass the dependence of HR on RAD51 mediator proteins. Such agents could potentially elevate cellular resistance to DNA damaging agents, thereby increasing cell survival and potentially reducing mutagenesis. This type of agent could be used to protect normal tissues in patients receiving oncologic therapies. Such agents also could serve as personal protection in the event of a nuclear disaster or a 'dirty bomb.'

A targeted approach that focuses on HR is particularly appealing, since several studies have suggested that HR inhibition preferentially sensitizes tumor cells relative to normal cells (Russell et al., 2003; Ito et al., 2005). In one such study, Gleevec-mediated inhibition of RAD51 expression resulted in an elevated radio-sensitivity for glioma cancer cell lines, but had no significant effect on normal human fibroblasts (Russell et al., 2003). Similarly, Ito et. al. blocked RAD51 expression with siRNA techniques in various human cancer cell lines. The sensitivity to cisplatin was enhanced in all of the human cancer cell lines tested, but not in normal human fibroblasts (Ito et al., 2005). Therefore, a strategy for pharmacologic inhibition of HR holds promise for improving the therapeutic ratios of existing oncology treatments.

A. RAD51 Protein

RAD51 filament formation is a well accepted critical step in the initiation of HR repair. Biochemical studies have shown that RAD51 protein assembles into filaments readily on sites of single stranded DNA (ssDNA). In vitro filament formation is magnesium and ATP dependent, and requires a concentration of RAD51 protein of approximately 250 nM. This reaction also demonstrates cooperativity, such that a threshold level of RAD51 binding to ssDNA will stimulate further filament formation ((Zaitseva et al., 1999; Shinohara et al., 1992). One mechanism by which cells can up-regulate filament formation is over-expression of RAD51 protein. RAD51 is over-expressed in a number of human cancer cell lines (Raderschall et al., 2002; Russell et al., 2003; Hansen et al., 2003) and human tumors (Maacke et al., 2000a; Maacke et al., 2000b; Han et al., 2002; Henning and Sturzbecher, 2003; Yoshikawa et al., 2000; Qiao et al., 2005). Fluorescence in situ hybridization (FISH) experiments have shown that the RAD51 gene is not amplified. Other experiments have demonstrated that RAD51 protein half-life is normal in tumor cells. Taken together, this suggests that the increased protein levels result from transcriptional up-regulation (Raderschall et al., 2002). There are also data to suggest that RAD51 over-expression can compensate for loss of RAD51 paralog proteins, thus by-passing the need for a mediator protein that would have otherwise been rate limiting (Takata et al., 2001). RAD51 over-expression is particularly dramatic in the case of pancreatic cancer. Han et. al. (2002) performed a cDNA microarray analysis comparing pancreatic cancer cells lines to normal pancreatic cells; RAD51 was among the 30 most over-expressed genes in this analysis. This result was confirmed with an immunohistochemical (IHC) analysis showing strong RAD51 staining in 71.8% of malignant pancreatic tumors in humans (Han et al., 2002). A similar study of 47 human pancreatic tumor tissue specimens showed RAD51 overexpression in 66% of tumors (Maacke et al., 2000b). In fact, RAD51 overexpression is so great that 7% of pancreatic cancer patients generate auto-antibodies to RAD51, which can be detected in their sera (Maacke et al., 2002). A functional analysis using a system of inducible RAD51 overexpression in pancreatic cells directly showed that overexpression confers resistance to DSB's (Maacke et al., 2000b). A growing body of literature agrees with this finding, suggesting that high RAD51 protein expression levels can modulate the resistance of cancer cells to IR (ionizing radiation) and some chemotherapeutic drugs.

B. Homologous Recombination and BRCA1 Mutations

The breast cancer susceptibility gene BRCA2 plays an important role in HR (Moynahan et al., 2001). It has been speculated that BRCA2 protein either chaperones RAD51 monomers, that it serves as mediator for RAD51 filament assembly at sites of DNA damage, and/or that it acts to stabilize existing filaments. A recent report suggested that RAD51 directly interacts with a C-terminal region of BRCA2 protein (Esashi et al., 2005). RAD51 is also known to directly bind six of the eight conserved BRC repeats within human BRCA2 (Chen et al., 1998; Wong et al., 1997). Crystal structure data have been generated using a fusion protein containing BRC4 covalently linked to the C-terminal core domain of RAD51. This and other studies have demonstrated that BRC repeats share a conserved motif that is thought to mimic a primary interface used in RAD51 polymerization (Shin et al., 2003; Pellegrini et al., 2002). Various BRC peptides have been shown capable of blocking self-association by RAD51 monomers, inhibiting RAD51 filament formation, and sensitizing cells to DNA damage (Chen et al., 1999; Davies et al., 2001; Yuan et al., 1999). For example Chen et. al. reported that conditional expression of wild-type BRC4 resulted in hypersensitivity to irradiation and an inability to form radiation-induced RAD51 foci in breast cancer cells (Chen et al., 1999).

Preliminary tumor studies by the present inventors focused on HR by modulating the RAD51 paralog protein XRCC3. Using xenograft tumors grown in nude mice, cisplatin treatment was found to produce regression and cure of HR-deficient xenograft tumors using a treatment schedule that has little effect of HR-competent tumors. Similarly, the HR-deficient tumors were sensitive to relatively low doses of ionizing radiation, compared to HR-competent tumors. Other clinical studies suggest that, like XRCC3-deficient tumors, HR-deficient human tumors (due to BRCA1-mutation) are especially susceptible to DNA damaging chemotherapeutic agents (Porter et al., 1994; Rubin et al., 1996). Tanaka and colleagues found that in a group ovarian cancer patients receiving ciplatin treatment, those defective for BRCA1 had a five-year survival of 79% while patients in the control group had a five-year survival of only 30% (Alda et al., 1998). Similarly, Marcus et al. (1996) found that BRCA1-defective women with breast cancer had relatively favorable outcomes, despite having tumors with higher grade and higher S-phase fraction. Thus, deficiencies of HR may sensitize tumor cells to some chemotherapy drugs and IR, providing evidence that pharmacologic inhibitors of HR are likely to improve the clinical efficacy of cancer treatments.

C. Cancer and DNA Damaging Agents

In certain embodiments, the invention is applicable to the treatment of cancer insofar as such treatments may involve DNA damaging agents.

Cancer cells that may be treated by methods and compositions of the invention also include cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepideimoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma;

embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The term "DNA damaging agent" refers to any agent that directly or indirectly damages DNA for which homologous recombination could repair the damage. Specific examples of DNA-damaging agents include alkylating agents, nitrosoureas, anti-metabolites, plant alkaloids, plant extracts and radioisotopes. Specific examples of agents also include DNA-damaging drugs, for example, 5-fluorouracil (5-FU), capecitabine, S-1 (Tegafur, 5-chloro-2,4-dihydroxypyridine and oxonic acid), 5-ethynyluracil, arabinosyl cytosine (ara-C), 5-azacytidine (5-AC), 2',2'-difluoro-2'-deoxycytidine (dFdC), purine antimetabolites (mercaptopurine, azathiopurine, thioguanine), gemcitabine hydrochlorine (Gemzar), pentostatin, allopurinol, 2-fluoro-arabinosyl-adenine (2F-ara-A), hydroxyurea, sulfur mustard (bischloroetyhylsulfide), mechlorethamine, melphalan, chlorambucil, cyclophosphamide, ifosfamide, thiotepa, AZQ, mitomycin C, dianhydrogalactitol, dibromoducitol, alkyl sulfonate (busulfan), nitrosoureas (BCNU, CCNU, 4-methyl CCNU or ACNU), procarbazine, decarbazine, rebeccamycin, anthracyclins such as doxorubicin (adriamycin; ADR), daunorubicin (Cerubicine), idarubicin (Idamycin) and epirubicin (Ellence), anthracyclin analogs such as mitoxantrone, actinimycin D, non-intercalating topoisomerase inhibitors such as epipodophyllotoxins (etoposide or VP 16, teniposide or VM-26), podophylotoxin, bleomycin (Bleo), pepleomycin, compounds that form adducts with nucleic acid including platinum derivatives, e.g., cisplatin (CDDP), trans analog of cisplatin, carboplatin, iproplatin, tetraplatin and oxaliplatin, as well as camptothecin, topotecan, irinotecan (CPT-11), and SN-38. Specific examples of nucleic acid damaging treatments include radiation e.g., ultraviolet (UV), infrared (IR), or α-, β-, or γ-radiation, as well as environmental shock, e.g., hyperthermia. One of skill in the art can identify and use other DNA-damaging agents and treatments.

D. Chemical Definitions

As used herein, a "small molecule" refers to an organic compound that is either synthesized via conventional organic chemistry methods (e.g., in a laboratory) or found in nature. Typically, a small molecule is characterized in that it contains several carbon-carbon bonds, and has a molecular weight of less than about 1500 grams/mole. In certain embodiments, small molecules are less than about 1000 grams/mole. In certain embodiments, small molecules are less than about 550 grams/mole. In certain embodiments, small molecules are between about 200 and about 550 grams/mole. In certain embodiments, small molecules exclude peptides (e.g., compounds comprising 2 or more amino acids joined by a peptidyl bond). In certain embodiments, small molecules exclude nucleic acids.

As used herein, the term "amino" means —NH$_2$; the ter, "nitro" means —NO$_2$; the term "halo" or "halogen" designates —F, —Cl, —Br or —I; the term "mercapto" means —SH; the term "cyano" means —CN; the term "azido" means —N$_3$; the term "silyl" means —SiH$_3$, and the term "hydroxy" means —OH. In certain embodiments, a halogen may be —Br or —I.

As used herein, a "monovalent anion" refers to anions of a −1 charge. Such anions are well-known to those of skill in the art. Non-limiting examples of monovalent anions include halides (e.g., F$^-$, Cl$^-$, Br$^-$ and I$^-$), NO$_2^-$, NO$_3^-$, hydroxide (OH$^-$) and azide (N$_3^-$).

As used herein, the structure ====== indicates that the bond may be a single bond or a double bond. Those of skill in the chemical arts understand that in certain circumstances, a double bond between two particular atoms is chemically feasible and in certain circumstances, a double bond is not. The present invention therefore contemplates that a double bond may be formed only when chemically feasible.

The term "alkyl" includes straight-chain alkyl, branched-chain alkyl, cycloalkyl (alicyclic), cyclic alkyl, heteroatom-unsubstituted alkyl, heteroatom-substituted alkyl, heteroatom-unsubstituted $C_n$-alkyl, and heteroatom-substituted $C_n$-alkyl. In certain embodiments, lower alkyls are contemplated. The term "lower alkyl" refers to alkyls of 1-6 carbon atoms (that is, 1, 2, 3, 4, 5 or 6 carbon atoms). The term "heteroatom-unsubstituted $C_n$-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted $C_1$-$C_{10}$-alkyl has 1 to 10 carbon atoms. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, and cyclohexyl, are all non-limiting examples of heteroatom-unsubstituted alkyl groups. The term "heteroatom-substituted $C_n$-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkyl has 1 to 10 carbon atoms. The following groups are all non-limiting examples of heteroatom-substituted alkyl groups: trifluoromethyl, —CH$_2$F, —CH$_2$Cl, —CH$_2$Br, —CH$_2$OH, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, CH$_2$CH$_2$OC(O)CH$_3$, —CH$_2$CH$_2$NHCO$_2$C(CH$_3$)$_3$, and —CH$_2$Si(CH$_3$)$_3$.

The term "alkenyl" includes straight-chain alkenyl, branched-chain alkenyl, cycloalkenyl, cyclic alkenyl, heteroatom-unsubstituted alkenyl, heteroatom-substituted alkenyl, heteroatom-unsubstituted $C_n$-alkenyl, and heteroatom-substituted $C_n$-alkenyl. In certain embodiments, lower alkenyls are contemplated. The term "lower alkenyl" refers to alkenyls of 1-6 carbon atoms (that is, 1, 2, 3, 4, 5 or 6 carbon atoms). The term "heteroatom-unsubstituted $C_n$-alkenyl" refers to a radical, having a linear or branched, cyclic or acyclic structure, further having at least one nonaromatic carbon-carbon double bond, but no carbon-carbon triple bonds, a total of n carbon atoms, three or more hydrogen atoms, and no heteroatoms. For example, a heteroatom-unsubstituted $C_2$-$C_{10}$-alkenyl has 2 to 10 carbon atoms. Heteroatom-unsubstituted alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "heteroatom-substituted $C_n$-alkenyl" refers to a radical, having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkenyl has 2 to 10 carbon atoms. The groups, —CH=CHF, —CH=CHCl and —CH=CHBr, are non-limiting examples of heteroatom-substituted alkenyl groups.

The term "aryl" includes heteroatom-unsubstituted aryl, heteroatom-substituted aryl, heteroatom-unsubstituted $C_n$-aryl, heteroatom-substituted $C_n$-aryl, heteroaryl, heterocyclic aryl groups, carbocyclic aryl groups, biaryl groups, and single-valent radicals derived from polycyclic fused hydrocarbons (PAHs). The term "heteroatom-unsubstituted $C_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted $C_6$-$C_{10}$-aryl has 6 to 10 carbon atoms. Non-limiting examples of heteroatom-unsubstituted aryl groups include phenyl (Ph), methylphenyl, (dimethyl)phenyl, —C$_6$H$_4$CH$_2$CH$_3$, —C$_6$H$_4$CH$_2$CH$_2$CH$_3$, —C$_6$H$_4$CH(CH$_3$)$_2$, —C$_6$H$_4$CH(CH$_2$)$_2$, —C$_6$H$_3$(CH$_3$)CH$_2$CH$_3$, C$_6$H$_4$CH—CH$_2$, C$_6$H$_4$CH—CHCH$_3$, —C$_6$H$_4$C≡CH, —C$_6$H$_4$C≡CCH$_3$, naphthyl, and the radical derived from biphenyl. The team "heteroatom-substituted $C_n$-aryl" refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted $C_1$-$C_{10}$-heteroaryl has 1 to 10 carbon atoms. Non-limiting examples of heteroatom-substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$OC(O)CH$_3$, —C$_6$H$_4$NH$_2$, —C$_6$H$_4$NHCH$_3$, —C$_6$H$_4$N(CH$_3$)$_2$, —C$_6$H$_4$CH$_2$OH, —C$_6$H$_4$CH$_2$OC(O)CH$_3$, —C$_6$H$_4$CH$_2$NH$_2$, —C$_6$H$_4$CF$_3$, —C$_6$H$_4$CN, —C$_6$H$_4$CHO, —C$_6$H$_4$CHO, —C$_6$H$_4$C(O)CH$_3$, —C$_6$H$_4$C(O)C$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, —C$_6$H$_4$CON(CH$_3$)$_2$, furanyl, thienyl, pyridyl, pyrrolyl, pyrimidyl, pyrazinyl, quinolyl, indolyl, and imidazoyl. In certain embodiments, heteroatom-substituted aryl groups are contemplated. In certain embodiments, heteroatom-unsubstituted aryl groups are contemplate. In certain embodiments, an aryl group may be mono-, di-, tri-, tetra- or penta-substituted with one or more heteroatom-containing substitutents.

The term "aralkyl" includes heteroatom-unsubstituted aralkyl, heteroatom-substituted aralkyl, heteroatom-unsubstituted $C_n$-aralkyl, heteroatom-substituted $C_n$-aralkyl, heteroaralkyl, and heterocyclic aralkyl groups. In certain embodiments, lower aralkyls are contemplated. The term "lower aralkyl" refers to aralkyls of 7-12 carbon atoms (that is, 7, 8, 9, 10, 11 or 12 carbon atoms). The teen "heteroatom-unsubstituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted $C_7$-$C_{10}$-aralkyl has 7 to 10 carbon atoms. Non-limiting examples of heteroatom-unsubstituted aralkyls are: phenylmethyl (benzyl, Bn) and phenylethyl. The term "heteroatom-substituted $C_n$-aralkyl" refers to a radical, having a single saturated carbon atom as the point of attachment, further having a total of n carbon atoms, 0, 1, or more than one hydrogen atom, and at least one heteroatom, wherein at least one of the carbon atoms is incorporated an aromatic ring structures, further wherein each heteroatom is independently selected from the group consisting of N, O, F, Cl, Br, I, Si, P, and S. For example, a heteroatom-substituted $C_2$-$C_{10}$-heteroaralkyl has 2 to 10 carbon atoms.

The term "acyl" includes straight-chain acyl, branched-chain acyl, cycloacyl, cyclic acyl, heteroatom-unsubstituted acyl, heteroatom-substituted acyl, heteroatom-unsubstituted $C_n$-acyl, heteroatom-substituted $C_n$-acyl, alkylcarbonyl, alkoxycarbonyl and aminocarbonyl groups. In certain embodiments, lower acyls are contemplated. The term "lower acyl" refers to acyls of 1-6 carbon atoms (that is, 1, 2, 3, 4, 5 or 6 carbon atoms). The term "heteroatom-unsubstituted $C_n$-acyl" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted $C_1$-$C_{10}$-acyl has 1 to 10 carbon atoms. The groups, —CHO, —C(O)CH$_3$, —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, and —COC$_6$H$_3$(CH$_3$)$_2$, are non-limiting examples of heteroatom-unsubstituted acyl groups. The term "heteroatom-substituted $C_n$-acyl" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom, in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-acyl has 1 to 10 carbon atoms. The groups, —C(O)CH$_2$CF$_3$, —CO$_2$H, —CO$_2$, CO$_2$CH$_3$, —CO$_2$CH$_2$CH$_3$, —CO$_2$CH$_2$CH$_2$CH$_3$, —CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, and —CONHCH$_2$CF$_3$, are non-limiting examples of heteroatom-substituted acyl groups.

The term "alkoxy" includes straight-chain alkoxy, branched-chain alkoxy, cycloalkoxy, cyclic alkoxy, heteroatom-unsubstituted alkoxy, heteroatom-substituted alkoxy, heteroatom-unsubstituted $C_n$-alkoxy, and heteroatom-substituted $C_n$-alkoxy. In certain embodiments, lower alkoxys are contemplated. The term "lower alkoxy" refers to alkoxys of 1-6 carbon atoms (that is, 1, 2, 3, 4, 5 or 6 carbon atoms). The term "heteroatom-unsubstituted $C_n$-alkoxy" refers to a group, having the structure —OR, in which R is a heteroatom-unsubstituted $C_n$-alkyl, as that term is defined above. Heteroatom-unsubstituted alkoxy groups include: —OCH$_3$, —OCH$_2$CH$_3$, —OCH$_2$CH$_2$CH$_3$, —OCH(CH$_3$)$_2$, and —OCH(CH$_2$)$_2$. The term "heteroatom-substituted $C_n$-alkoxy" refers to a group, having the structure —OR, in which R is a heteroatom-substituted $C_n$-alkyl, as that term is defined above. For example, —OCH$_2$CF$_3$ is a heteroatom-substituted alkoxy group.

The term "alkenyloxy" includes straight-chain alkenyloxy, branched-chain alkenyloxy, cycloalkenyloxy, cyclic alkenyloxy, heteroatom-unsubstituted alkenyloxy, heteroatom-substituted alkenyloxy, heteroatom-unsubstituted $C_n$-alkenyloxy, and heteroatom-substituted $C_n$-alkenyloxy. The term "heteroatom-unsubstituted $C_n$-alkenyloxy" refers to a group, having the structure —OR, in which R is a heteroatom-unsubstituted $C_n$-alkenyl, as that term is defined above. The term "heteroatom-substituted $C_n$-alkenyloxy" refers to a group, having the structure —OR, in which R is a heteroatom-substituted $C_n$-alkenyl, as that term is defined above.

The term "alkynyloxy" includes straight-chain alkynyloxy, branched-chain alkynyloxy, cycloalkynyloxy, cyclic alkynyloxy, heteroatom-unsubstituted alkynyloxy, heteroatom-substituted alkynyloxy, heteroatom-unsubstituted $C_n$-alkynyloxy, and heteroatom-substituted $C_n$-alkynyloxy. The term "heteroatom-unsubstituted $C_n$-alkynyloxy" refers to a group, having the structure —OR, in which R is a heteroatom-unsubstituted $C_n$-alkynyl, as that term is defined above. The term "heteroatom-substituted $C_n$-alkynyloxy" refers to a group, having the structure —OR, in which R is a heteroatom-substituted $C_n$-alkynyl, as that term is defined above.

The term "aryloxy" includes heteroatom-unsubstituted aryloxy, heteroatom-substituted aryloxy, heteroatom-unsubstituted $C_n$-aryloxy, heteroatom-substituted $C_n$-aryloxy, heteroaryloxy, and heterocyclic aryloxy groups. The term "heteroatom-unsubstituted $C_n$-aryloxy" refers to a group, having the structure —OAr, in which Ar is a heteroatom-unsubstituted $C_n$-aryl, as that term is defined above. A non-limiting example of a heteroatom-unsubstituted aryloxy group is —OC$_6$H$_5$. The term "heteroatom-substituted $C_n$-aryloxy" refers to a group, having the structure —OAr, in which Ar is a heteroatom-substituted $C_n$-aryl, as that term is defined above.

The term "aralkyloxy" includes heteroatom-unsubstituted aralkyloxy, heteroatom-substituted aralkyloxy, heteroatom-unsubstituted $C_n$-aralkyloxy, heteroatom-substituted $C_n$-aralkyloxy, heteroaralkyloxy, and heterocyclic aralkyloxy groups. The term "heteroatom-unsubstituted $C_n$-aralkyloxy" refers to a group, having the structure —OAr, in which Ar is a heteroatom-unsubstituted $C_n$-aralkyl, as that term is defined above. The term "heteroatom-substituted $C_n$-aralkyloxy" refers to a group, having the structure —OAr, in which Ar is a heteroatom-substituted $C_n$-aralkyl, as that term is defined above.

The term "acyloxy" includes straight-chain acyloxy, branched-chain acyloxy, cycloacyloxy, cyclic acyloxy, heteroatom-unsubstituted acyloxy, heteroatom-substituted acyloxy, heteroatom-unsubstituted $C_n$-acyloxy, heteroatom-substituted $C_n$-acyloxy, alkylcarbonyloxy, arylcarbonyloxy, alkoxycarbonyloxy, aryloxycarbonyloxy, and carboxylate groups. The term "heteroatom-unsubstituted $C_n$-acyloxy" refers to a group, having the structure —OAc, in which Ac is a heteroatom-unsubstituted $C_n$-acyl, as that term is defined above. For example, —OC(O)CH$_3$ is a non-limiting example of a heteroatom-unsubstituted acyloxy group. The term "heteroatom-substituted $C_n$-acyloxy" refers to a group, having the structure —OAc, in which Ac is a heteroatom-substituted $C_n$-acyl, as that term is defined above. For example, —OC(O)OCH$_3$ and —OC(O)NHCH$_3$ are non-limiting examples of heteroatom-unsubstituted acyloxy groups.

The term "alkylamino" includes straight-chain alkylamino, branched-chain alkylamino, cycloalkylamino, cyclic alkylamino, heteroatom-unsubstituted alkylamino, heteroatom-substituted alkylamino, heteroatom-unsubstituted $C_n$-alkylamino, and heteroatom-substituted $C_n$-alkylamino. The term "heteroatom-unsubstituted $C_n$-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted $C_1$-$C_{10}$-alkylamino has 1 to 10 carbon atoms. The term "heteroatom-unsubstituted $C_n$-alkylamino" includes groups, having the structure —NHR, in which R is a heteroatom-unsubstituted $C_n$-alkyl, as that term is defined above. A heteroatom-unsubstituted alkylamino group would include —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —N(CH$_3$)$_2$, —N(CH$_3$)CH$_2$CH$_3$, —N(CH$_2$CH$_3$)$_2$, N-pyrrolidinyl, and N-piperidinyl. The term "heteroatom-substituted $C_n$-alkylamino" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_1$-$C_{10}$-alkylamino has 1 to 10 carbon atoms. The term "heteroatom-substituted $C_n$-alkylamino" includes groups, having the structure —NHR, in which R is a heteroatom-substituted $C_n$-alkyl, as that term is defined above.

The term "alkenylamino" includes straight-chain alkenylamino, branched-chain alkenylamino, cycloalkenylamino, cyclic alkenylamino, heteroatom-unsubstituted alkenylamino, heteroatom-substituted alkenyl amino, heteroatom-unsubstituted $C_n$-alkenylamino, heteroatom-substituted $C_n$-alkenylamino, dialkenylamino, and alkyl(alkenyl)amino groups. The term "heteroatom-unsubstituted $C_n$-alkenylamino" refers to a radical, having a single nitrogen atom as the point of attachment, further having one or two carbon atoms attached to the nitrogen atom, further having a linear or branched, cyclic or acyclic structure, containing at least one nonaromatic carbon-carbon double bond, a total of n carbon atoms, 4 or more hydrogen atoms, a total of one nitrogen atom, and no additional heteroatoms. For example, a heteroatom-unsubstituted $C_2$-$C_{10}$alkenylamino has 2 to 10 carbon atoms. The term "heteroatom-unsubstituted $C_n$-alkenylamino" includes groups, having the structure —NHR, in which R is a heteroatom-unsubstituted $C_n$-alkenyl, as that term is defined above. The term "heteroatom-substituted $C_n$-alkenylamino" refers to a radical, having a single nitrogen atom as the point of attachment and at least one nonaromatic carbon-carbon double bond, but no carbon-carbon triple bonds, further having one or two carbon atoms attached to the nitrogen atom, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkenylamino has 2 to 10 carbon atoms. The term "heteroatom-substituted $C_n$-alkenylamino" includes groups, having the structure —NHR, in which R is a heteroatom-substituted $C_n$-alkenyl, as that term is defined above.

The term "alkynylamino" includes straight-chain alkynylamino, branched-chain alkynylamino, cycloalkynylamino, cyclic alkynyl amino, heteroatom-unsubstituted alkynylamino, heteroatom-substituted alkynylamino, heteroatom-unsubstituted $C_n$-alkynylamino, heteroatom-substituted $C_n$-alkynylamino, dialkynylamino, alkyl(alkynyl)amino, and alkenyl(alkynyl)amino groups. The term "heteroatom-unsubstituted $C_n$-alkynylamino" refers to a radical, having a single nitrogen atom as the point of attachment, further having one or two carbon atoms attached to the nitrogen atom, further having a linear or branched, cyclic or acyclic structure, containing at least one carbon-carbon triple bond, a total of n carbon atoms, at least one hydrogen atoms, a total of one nitrogen atom, and no additional heteroatoms. For example, a heteroatom-unsubstituted $C_2$-$C_{10}$-alkynylamino has 2 to 10 carbon atoms. The tem). "heteroatom-unsubstituted $C_n$-alkynylamino" includes groups, having the structure —NHR, in which R is a heteroatom-unsubstituted $C_n$-alkynyl, as that term is defined above. The term "heteroatom-substituted $C_n$-alkynylamino" refers to a radical, having a single nitrogen atom as the point of attachment, further having one or two carbon atoms attached to the nitrogen atom, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkynylamino has 2 to 10 carbon atoms. The term "heteroatom-substituted $C_n$-alkynylamino" includes groups, having the structure —NHR, in which R is a heteroatom-substituted $C_n$-alkynyl, as that term is defined above.

The term "arylamino" includes heteroatom-unsubstituted arylamino, heteroatom-substituted arylamino, heteroatom-unsubstituted $C_n$-arylamino, heteroatom-substituted $C_n$-arylamino, heteroarylamino, heterocyclic arylamino, and alkyl(aryl)amino groups. The term "heteroatom-unsubstituted $C_n$-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, a heteroatom-unsubstituted $C_6$-$C_{10}$-arylamino has 6 to 10 carbon atoms. The term "heteroatom-unsubstituted $C_n$-arylamino" includes groups, having the structure —NHR, in which R is a heteroatom-unsubstituted $C_n$-aryl, as that term is defined above. The term "heteroatom-substituted $C_n$-arylamino" refers to a radical, having a single nitrogen atom as the point of attachment, further having a total of n carbon atoms, at least one hydrogen atom, at least one additional heteroatoms, that is, in addition to the nitrogen atom at the point of attachment, wherein at least one of the carbon atoms is incorporated into one or more aromatic ring structures, further wherein each additional heteroatom is independently selected from the group consisting of N, O, F, Cl, Br, I, Si, P, and S. For example, a heteroatom-substituted $C_6$-$C_{10}$-arylamino has 6 to 10 carbon atoms. The term "heteroatom-substituted $C_n$-arylamino" includes groups, having the structure —NHR, in which R is a heteroatom-substituted $C_n$-aryl, as that term is defined above.

The term "aralkylamino" includes heteroatom-unsubstituted aralkylamino, heteroatom-substituted aralkylamino, heteroatom-unsubstituted $C_n$-aralkylamino, heteroatom-substituted $C_n$-aralkylamino, heteroaralkylamino, heterocyclic aralkylamino groups, and diaralkylamino groups. The term "heteroatom-unsubstituted $C_n$-aralkylamino" refers to a radical, having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, a heteroatom-unsubstituted $C_7$-$C_{10}$-aralkylamino has 7 to 10 carbon atoms. The term "heteroatom-unsubstituted $C_n$-aralkylamino" includes groups, having the structure —NHR, in which R is a heteroatom-unsubstituted $C_n$-aralkyl, as that term is defined above. The term "heteroatom-substituted $C_n$-aralkylamino" refers to a radical, having a single nitrogen atom as the point of attachment, further having at least one or two saturated carbon atoms attached to the nitrogen atom, further having a total of n carbon atoms, 0, 1, or more than one hydrogen atom, at least one additional heteroatom, that is, in addition to the nitrogen atom at the point of attachment, wherein at least one of the carbon atom incorporated into an aromatic ring, further wherein each heteroatom is independently selected from the group consisting of N, O, F, Cl, Br, I, Si, P, and S. For example, a heteroatom-substituted $C_7$-$C_{10}$-aralkylamino has 7 to 10 carbon atoms. The term "heteroatom-substituted $C_n$-aralkylamino" includes groups, having the structure —NHR, in which R is a heteroatom-substituted $C_n$-aralkyl, as that term is defined above.

The term "amido" includes straight-chain amido, branched-chain amido, cycloamido, cyclic amido, heteroatom-unsubstituted amido, heteroatom-substituted amido, heteroatom-unsubstituted $C_n$-amido, heteroatom-substituted $C_n$-amido, alkylcarbonylamino, arylcarbonylamino, alkoxycarbonylamino, aryloxycarbonylamino, acylamino, alkylaminocarbonylamino, arylaminocarbonylamino, and ureido groups. The term "heteroatom-unsubstituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted $C_1$-$C_{10}$-amido has 1 to 10 carbon atoms. The term "heteroatom-unsubstituted $C_n$-amido" includes groups, having the structure —NHR, in which R is a heteroatom-unsubstituted $C_n$-acyl, as that term is defined above. The group, —NHC(O)CH$_3$, is a non-limiting example of a heteroatom-unsubstituted amido group. The term "heteroatom-substituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-amido has 1 to 10 carbon atoms. The term "heteroatom-substituted $C_n$-amido" includes groups, having the structure —NHR, in which R is a heteroatom-unsubstituted $C_n$-acyl, as that term is defined above. The group, —NHCO$_2$CH$_3$, is a non-limiting example of a heteroatom-substituted amido group.

The term "alkylthio" includes straight-chain alkylthio, branched-chain alkylthio, cycloalkylthio, cyclic alkylthio, heteroatom-unsubstituted alkylthio, heteroatom-substituted alkylthio, heteroatom-unsubstituted $C_n$-alkylthio, and heteroatom-substituted $C_n$-alkylthio. The term "heteroatom-unsubstituted $C_n$-alkylthio" refers to a group, having the structure —SR, in which R is a heteroatom-unsubstituted $C_n$-alkyl, as that term is defined above. The group, —SCH$_3$, is an example of a heteroatom-unsubstituted alkylthio group. The term "heteroatom-substituted $C_n$-alkylthio" refers to a group, having the structure —SR, in which R is a heteroatom-substituted $C_n$-alkyl, as that term is defined above.

The term "alkenylthio" includes straight-chain alkenylthio, branched-chain alkenylthio, cycloalkenylthio, cyclic alkenylthio, heteroatom-unsubstituted alkenylthio, heteroatom-substituted alkenylthio, heteroatom-unsubstituted $C_n$-alkenylthio, and heteroatom-substituted $C_n$-alkenylthio. The term "heteroatom-unsubstituted $C_n$-alkenylthio" refers to a group, having the structure —SR, in which R is a heteroatom-unsubstituted $C_n$-alkenyl, as that term is defined above. The term "heteroatom-substituted $C_n$-alkenylthio" refers to a group, having the structure —SR, in which R is a heteroatom-substituted $C_n$-alkenyl, as that term is defined above.

The term "alkynylthio" includes straight-chain alkynylthio, branched-chain alkynylthio, cycloalkynylthio, cyclic alkynylthio, heteroatom-unsubstituted alkynylthio, heteroatom-substituted alkynylthio, heteroatom-unsubstituted $C_n$-alkynylthio, and heteroatom-substituted $C_n$-alkynylthio. The term "heteroatom-unsubstituted $C_n$-alkynylthio" refers to a group, having the structure —SR, in which R is a heteroatom-unsubstituted $C_n$-alkynyl, as that term is defined above. The term "heteroatom-substituted $C_n$-alkynylthio" refers to a group, having the structure —SR, in which R is a heteroatom-substituted $C_n$-alkynyl, as that team is defined above.

The term "arylthio" includes heteroatom-unsubstituted arylthio, heteroatom-substituted arylthio, heteroatom-unsubstituted $C_n$-arylthio, heteroatom-substituted $C_n$-arylthio, heteroarylthio, and heterocyclic arylthio groups. The term "heteroatom-unsubstituted $C_n$-arylthio" refers to a group, having the structure —SAr, in which Ar is a heteroatom-unsubstituted $C_n$-aryl, as that term is defined above. The group, —SC$_6$H$_5$, is an example of a heteroatom-unsubstituted arylthio group. The term "heteroatom-substituted $C_n$-arylthio" refers to a group, having the structure —SAr, in which Ar is a heteroatom-substituted $C_n$-aryl, as that term is defined above.

The term "aralkylthio" includes heteroatom-unsubstituted aralkylthio, heteroatom-substituted aralkylthio, heteroatom-unsubstituted $C_n$-aralkylthio, heteroatom-substituted aralkylthio, heteroaralkylthio, and heterocyclic aralkylthio groups. The term "heteroatom-unsubstituted $C_n$-aralkylthio" refers to a group, having the structure —SAr, in which Ar is a heteroatom-unsubstituted $C_n$-aralkyl, as that term is defined above. The group, —SCH$_2$C$_6$H$_5$, is an example of a heteroatom-unsubstituted aralkyl group. The term "heteroatom-substituted $C_n$-aralkylthio" refers to a group, having the structure —SAr, in which Ar is a heteroatom-substituted $C_n$-aralkyl, as that term is defined above.

The term "acylthio" includes straight-chain acylthio, branched-chain acylthio, cycloacylthio, cyclic acylthio, heteroatom-unsubstituted acylthio, heteroatom-substituted acylthio, heteroatom-unsubstituted $C_n$-acylthio, heteroatom-substituted $C_n$-acylthio, alkylcarbonyloxy, aryloxycarbonyloxy, alkoxycarbonyloxy, aryloxycarbonyloxy, and carboxylate groups. The term "heteroatom-unsubstituted $C_n$-acylthio" refers to a group, having the structure —SAc, in which Ac is a heteroatom-unsubstituted $C_n$-acyl, as that term is defined above. The group, —SCOCH$_3$, is an example of a heteroatom-unsubstituted acylthio group. The term "heteroatom-substituted $C_n$-acylthio" refers to a group, having the structure —SAc, in which Ac is a heteroatom-substituted $C_n$-acyl, as that term is defined above.

The term "alkylsilyl" includes straight-chain alkylsilyl, branched-chain alkylsilyl, cycloalkylsilyl, cyclic alkylsilyl, heteroatom-unsubstituted alkylsilyl, heteroatom-substituted alkylsilyl, heteroatom-unsubstituted $C_n$-alkylsilyl, and heteroatom-substituted $C_n$-alkylsilyl. The term "heteroatom-unsubstituted $C_n$-alkylsilyl" refers to a radical, having a single silicon atom as the point of attachment, further having one, two, or three saturated carbon atoms attached to the silicon atom, further having a linear or branched, cyclic or acyclic structure, containing a total of n carbon atoms, all of which are nonaromatic, 5 or more hydrogen atoms, a total of 1 silicon atom, and no additional heteroatoms. For example, a heteroatom-unsubstituted $C_1$-$C_{10}$-alkylsilyl has 1 to 10 carbon atoms. An alkylsilyl group includes dialkylamino groups. The groups, —Si(CH$_3$)$_3$ and —Si(CH$_3$)$_2$C(CH$_3$)$_3$, are non-limiting examples of heteroatom-unsubstituted alkylsilyl groups. The term "heteroatom-substituted $C_n$-alkylsilyl" refers to a radical, having a single silicon atom as the point of attachment, further having at least one, two, or three saturated carbon atoms attached to the silicon atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the silicon atom at the point of attachment, wherein each additional heteroatom is independently selected from the group consisting of N, O, F, Cl, Br, I, Si, P, and S. For example, a heteroatom-substituted $C_1$-$C_{10}$-alkylsilyl has 1 to 10 carbon atoms.

The term "phosphonate" includes straight-chain phosphonate, branched-chain phosphonate, cyclophosphonate, cyclic phosphonate, heteroatom-unsubstituted phosphonate, heteroatom-substituted phosphonate, heteroatom-unsubstituted $C_n$-phosphonate, and heteroatom-substituted $C_n$-phosphonate. The term "heteroatom-unsubstituted $C_n$-phosphonate" refers to a radical, having a single phosphorous atom as the point of attachment, further having a linear or branched, cyclic or acyclic structure, further having a total of n carbon atoms, 2 or more hydrogen atoms, a total of three oxygen atom, and no additional heteroatoms. The three oxygen atoms are directly attached to the phosphorous atom, with one of these oxygen atoms doubly bonded to the phosphorous atom. For example, a heteroatom-unsubstituted $C_0$-$C_{10}$-phosphonate has 0 to 10 carbon atoms. The groups, —P(O)(OH)$_2$, —P(O)(OH)OCH$_3$, —P(O)(OH)OCH$_2$CH$_3$, —P(O)(OCH$_3$)$_2$, and —P(O)(OH)(OC$_6$H$_5$) are non-limiting examples of heteroatom-unsubstituted phosphonate groups. The term "heteroatom-substituted $C_n$-phosphonate" refers to a radical, having a single phosphorous atom as the point of attachment, further having a linear or branched, cyclic or acyclic structure, further having a total of n carbon atoms, 2 or more hydrogen atoms, three or more oxygen atoms, three of which are directly attached to the phosphorous atom, with one of these three oxygen atoms doubly bonded to the phosphorous atom, and further having at least one additional heteroatom in addition to the three oxygen atoms, wherein each additional heteroatom is independently selected from the group consisting of N, O, F, Cl, Br, I, Si, P, and S. For example, a heteroatom-unsubstituted $C_0$-$C_{10}$-phosphonate has 0 to 10 carbon atoms.

The term "phosphinate" includes straight-chain phosphinate, branched-chain phosphinate, cyclophosphinate, cyclic phosphinate, heteroatom-unsubstituted phosphinate, heteroatom-substituted phosphinate, heteroatom-unsubstituted $C_n$-phosphinate, and heteroatom-substituted $C_n$-phosphinate. The term "heteroatom-unsubstituted $C_n$-phosphinate" refers to a radical, having a single phosphorous atom as the point of attachment, further having a linear or branched, cyclic or acyclic structure, further having a total of n carbon atoms, 2 or more hydrogen atoms, a total of two oxygen atom, and no additional heteroatoms. The two oxygen atoms are directly attached to the phosphorous atom, with one of these oxygen atoms doubly bonded to the phosphorous atom. For example, a heteroatom-unsubstituted $C_0$-$C_{10}$-phosphinate has 0 to 10 carbon atoms. The groups, —P(O)(OH)H, —P(O)(OH)$CH_3$, —P(O)(OH)$CH_2CH_3$, —P(O)(O$CH_3$)$CH_3$, and —P(O)(O$C_6H_5$)H are non-limiting examples of heteroatom-unsubstituted phosphinate groups. The term "heteroatom-substituted $C_n$-phosphinate" refers to a radical, having a single phosphorous atom as the point of attachment, further having a linear or branched, cyclic or acyclic structure, further having a total of n carbon atoms, 2 or more hydrogen atoms, two or more oxygen atoms, two of which are directly attached to the phosphorous atom, with one of these two oxygen atoms doubly bonded to the phosphorous atom, and further having at least one additional heteroatom in addition to the two oxygen atoms, wherein each additional heteroatom is independently selected from the group consisting of N, O, F, Cl, Br, I, Si, P, and S. For example, a heteroatom-unsubstituted $C_0$-$C_{10}$-phosphinate has 0 to 10 carbon atoms.

Any apparently unfulfilled valency is to be understood to be properly filled by hydrogen atom(s). For example, a compound with a substituent of —O or —N is to be understood to be —OH or —$NH_2$, respectively.

Any genus, subgenus, or specific compound discussed herein is specifically contemplated as being excluded from any embodiment described herein.

Compounds described herein may be prepared synthetically using conventional organic chemistry methods known to those of skill in the art and/or are commercially available (e.g., ChemBridge Co., San Diego, Calif.).

The claimed invention is also intended to encompass salts of any of the compounds of the present invention. The term "salt(s)" as used herein, is understood as being acidic and/or basic salts formed with inorganic and/or organic acids and bases. Zwitterions (internal or inner salts) are understood as being included within the term "salt(s)" as used herein, as are quaternary ammonium salts such as alkylammonium salts. Nontoxic, pharmaceutically acceptable salts are preferred, although other salts may be useful, as for example in isolation or purification steps during synthesis. Salts include, but are not limited to, sodium, lithium, potassium, amines, tartrates, citrates, hydrohalides, phosphates and the like. A salt may be a pharmaceutically acceptable salt, for example. Thus, pharmaceutically acceptable salts of compounds of the present invention are contemplated.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

Derivatives of compounds of the present invention are also contemplated. In certain aspects, "derivative" refers to a chemically modified compound that still retains the desired effects of the compound prior to the chemical modification. Such derivatives may have the addition, removal, or substitution of one or more chemical moieties on the parent molecule. Non-limiting examples of the types modifications that can be made to the compounds and structures disclosed herein include the addition or removal of lower alkanes such as methyl, ethyl, propyl, or substituted lower alkanes such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, heteroatoms such as N, S, or O can be substituted into the structure instead of a carbon atom.

Compounds employed in methods of the invention may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S- or the R-configuration, as defined by the IUPAC 1974 Recommendations. Compounds may be of the D- or L-form, for example. It is well known in the art how to prepare and isolate such optically active forms. For example, mixtures of stereoisomers may be separated by standard techniques including, but not limited to, resolution of racemic form, normal, reverse-phase, and chiral chromatography, preferential salt formation, recrystallization, and the like, or by chiral synthesis either from chiral starting materials or by deliberate synthesis of target chiral centers.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

As noted above, compounds of the present invention may exist in prodrug form. As used herein, "prodrug" is intended to include any covalently bonded carriers which release the active parent drug or compounds that are metabolized in vivo to an active drug or other compounds employed in the methods of the invention in vivo when such prodrug is administered to a subject. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a subject, cleaves to form a free hydroxyl, free amino, or carboxylic acid, respectively. Other examples include, but are not limited to, acetate, formate, and benzoate derivatives of alcohol and amine functional groups; and alkyl, carbocyclic, aryl, and alkylaryl esters such as methyl, ethyl, propyl, isopropyl, butyl, isobutyl, sec-butyl, tert-butyl, cyclopropyl, phenyl, benzyl, and phenethyl esters, and the like.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, Selection and Use* (2002), which is incorporated herein by reference.

E. Nucleic Acids

The present invention concerns polynucleotides and nucleic acids that can be used to alter the nucleic acid sequence of endogenous DNA through homologous recombination. These polynucleotides or nucleic acid molecules may be isolated and/or purified from cells or a cell-extract in embodiments of the invention.

Exogenous nucleic acids that may be used in the invention include, but are not limited to, nucleic acids of the following lengths or at least the following lengths: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 10100, 10200, 10300, 10400, 10500, 10600, 10700, 10800, 10900, 11000, 11100, 11200, 11300, 11400, 11500, 11600, 11700, 11800, 11900, 12000 or more nucleotides, nucleosides, or base pairs.

"Isolated substantially away from other coding sequences" means that the gene of interest forms part of the coding region of the nucleic acid segment, and that the segment does not contain large portions of naturally-occurring coding nucleic acid, such as large chromosomal fragments or other functional genes or cDNA coding regions. Of course, this refers to the nucleic acid segment as originally isolated, and does not exclude genes or coding regions later added to the segment by human manipulation.

In particular embodiments, the invention concerns isolated DNA segments and recombinant vectors incorporating DNA sequences that contain sequences that will be incorporated into a host cell's DNA through homologous recombination.

In particular embodiments, the invention concerns isolated nucleic acid segments and recombinant vectors incorporating DNA sequences that are to be reflected in the host cell's genome through homologous recombination.

Vectors of the present invention are designed, primarily, to transform cells with a desired sequence that can lead to the introduction or deletion of all or part of that sequence. In some embodiments, this may involve a sequence under the control of a eukaryotic promoter (i.e., constitutive, inducible, repressible, tissue specific). Also, the vectors may contain a selectable marker if, for no other reason, to facilitate their manipulation in vitro. However, selectable markers may play an important role in producing recombinant cells.

Tables 1 and 2, below, list a variety of regulatory signals for use according to the present invention.

TABLE 1

| Inducible Elements | | |
|---|---|---|
| Element | Inducer | References |
| MT II | Phorbol Ester (TPA) Heavy metals | Palmiter et al., 1982; Haslinger and Karin, 1985; Searle et al., 1985; Stuart et al., 1985; Imagawa et al., 1987; Karin et al., 1987; Angel et al., 1987b; McNeall et al., 1989 |
| MMTV (mouse mammary tumor virus) | Glucocorticoids | Huang et al., 1981; Lee et al., 1981; Majors and Varmus, 1983; Lee et al., 1984; Ponta et al., 1985 |
| β-Interferon | poly(rI)x poly(rc) | Tavernier et al., 1983 |
| Adenovirus 5 E2 | Ela | Imperiale and Nevins, 1984 |
| Collagenase | Phorbol Ester (TPA) | Angel et al., 1987a |
| Stromelysin | Phorbol Ester (TPA) | Angel et al., 1987b |
| SV40 | Phorbol Ester (TFA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | Ela, SV40 Large T Antigen | Taylor et al., 1989; Taylor and Kingston, 1990a, b |
| Proliferin | Phorbol Ester-TPA | Mordacq and Linzer, 1989 |
| Tumor Necrosis Factor | MA | Hensel et al., 1989 |
| Thyroid Stimulating Hormone α Gene | Thyroid Hormone | Chatterjee et al., 1989 |

TABLE 2

| Other Promoter/Enhancer Elements | |
|---|---|
| Promoter/Enhancer | References |
| Immunoglobulin Heavy Chain | Banerji et al., 1983; Gilles et al., 1983; Grosschedl and Baltimore, 1985; Atchison and Perry, 1986, 1987; Imler et al., 1987; Neuberger et al., 1988; Kiledjian et al., 1988; |
| Immunoglobulin Light Chain | Queen and Baltimore, 1983; Picard and Schaffner, 1985 |
| T-Cell Receptor | Luria et al., 1987, Winoto and Baltimore, 1989; Redondo et al., 1990 |
| HLA DQ α and DQ β | Sullivan and Peterlin, 1987 |
| β-Interferon | Goodbourn et al., 1986; Fujita et al., 1987; Goodbourn and Maniatis, 1985 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Drα | Sherman et al., 1989 |
| β-Actin | Kawamoto et al., 1988; Ng et al.; 1989 |
| Muscle Creatine Kinase | Jaynes et al., 1988; Horlick and Benfield, 1989; Johnson et al., 1989a |
| Prealbumin (Transthyretin) | Costa et al., 1988 |
| Elastase I | Omitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987; Tronche et al., 1989, 1990 |
| α-Fetoprotein | Godbout et al., 1988; Campere and Tilghman, 1989 |
| γ-Globin | Bodine and Ley, 1987; Perez-Stable and Constantini, 1990 |
| β-Globin | Trudel and Constantini, 1987 |
| c-fos | Cohen et al., 1987 |
| c-HA-ras | Treisman, 1985; Deschamps et al., 1985 |
| Insulin | Edlund et al., 1985 |
| Neural Cell Adhesion Molecule (NCAM) | Hirsh et al., 1990 |
| $a_1$ Antitrypain | Latimer et al., 1990 |
| H2B (TH2B) Histone | Hwang et al., 1990 |
| Mouse or Type I Collagen | Rippe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |

TABLE 2-continued

Other Promoter/Enhancer Elements

| Promoter/Enhancer | References |
| --- | --- |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987 Schaffner et al., 1988 |
| Polyoma | Swartzendruber and Lehman, 1975; Vasseur et al., 1980; Katinka et al., 1980, 1981; Tyndell et al., 1981; Dandolo et al., 1983; Hen et al., 1986; Campbell and Villarreal, 1988 |
| Retroviruses | Kriegler and Botchan, 1983; Kriegler et al., 1984a, b; Bosze et al., 1986; Miksicek et al., 1986; Celander and Haseltine, 1987; Thiesen et al., 1988; Celander et al., 1988; Chol et al., 1996; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987, Stephens and Hentschel, 1987 |
| Hepatitis B Virus | Bulla and Siddiqui, 1988; Jameel and Siddiqui, 1986; Shaul and Ben-Levy, 1987; Spandau and Lee, 1988 |
| Human Immunodeficiency Virus | Muesing et al., 1987; Hauber and Cullen, 1988; Jakobovits et al., 1988; Feng and Holland, 1988; Takebe et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

The promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation.

The term "promoter" will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between elements is flexible, so that promoter function is preserved when elements are inverted or moved relative to one another. In the tk promoter, the spacing between elements can be increased to 50 bp apart before activity begins to decline. Depending on the promoter, it appears that individual elements can function either co-operatively or independently to activate transcription.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities.

Promoters and enhancers have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way.

In some embodiments, the promoter for use in the present invention is the cytomegalovirus (CMV) immediate early (IE) promoter. This promoter is commercially available from Invitrogen in the vector pcDNAIII, which is some for use in the present invention. Also contemplated as useful in the present invention are the dectin-1 and dectin-2 promoters. Below are a list of additional viral promoters, cellular promoters/enhancers and inducible promoters/enhancers that could be used in combination with the present invention. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

Another signal that may prove useful is a polyadenylation signal. Such signals may be obtained from the human growth hormone (hGH) gene, the bovine growth hormone (BGH) gene, or SV40.

The use of internal ribosome binding sites (IRES) elements are used to create multigene, or polycistronic, messages. IRES elements are able to bypass the ribosome scanning model of 5-methylated cap-dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

In any event, it will be understood that promoters are DNA elements which when positioned functionally upstream of a gene leads to the expression of that gene. Most transgene constructs of the present invention are functionally positioned downstream of a promoter element.

Compositions and methods of the invention are provided for administering the compositions of the invention to a patient.

Nucleic acids may also be comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., (2001) and Ausubel et al., 1996, both incorporated herein by reference. In addition to encoding a modified polypeptide such as modified gelonin, a vector may encode non-modified polypeptide sequences such as a tag or targeting molecule. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage. A targeting molecule is one that directs the modified polypeptide to a particular organ, tissue, cell, or other location in a subject's body.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

Protamine may also be used to form a complex with an expression construct. Such complexes may then be formulated with the lipid compositions described above for administration to a cell. Protamines are small highly basic nucleoproteins associated with DNA. Their use in the delivery of nucleic acids is described in U.S. Pat. No. 5,187,260, which is incorporated by reference.

The following are methods of recombinant gene delivery to a given host cell and are thus considered consistent with the present invention.

1. Methods of Gene Transfer

Suitable methods for nucleic acid delivery to effect expression of compositions of the present invention are believed to include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

2. Knockout Animals

The generation of an animal model lacking a particular genetic sequence is considered part of the invention. The lack of genetic sequences may provoke various types of pathophysiological disturbances in a knockout animal. One method of inhibiting the endogenous expression of a gene in an animal is to disrupt the gene in germline cells and produce offspring from these cells. This method is generally known as knockout technology. U.S. Pat. No. 5,616,491, incorporated herein by reference in its entirety, generally describes the techniques involved in the preparation of knockout mice, and in particular describes mice having a suppressed level of expression of the gene encoding CD28 on T cells, and mice wherein the expression of the gene encoding CD45 is suppressed on B cells. Pfeffer et al. (1993) describe mice in which the gene encoding the tumor necrosis factor receptor p55 has been suppressed. The mice showed a decreased response to tumor necrosis factor signaling. Fung-Leung et al. (1991a; 1991b) describe knockout mice lacking expression of the gene encoding CD8. These mice were found to have a decreased level of cytotoxic T cell response to various antigens and to certain viral pathogens such as lymphocytic choriomeningitis virus.

The term "knockout" refers to a partial or complete suppression of the expression of at least a portion of a protein encoded by an endogenous DNA sequence in a cell. The term "knockout construct" refers to a nucleic acid sequence that is designed to decrease or suppress expression of a protein encoded by endogenous DNA sequences in a cell. The nucleic acid sequence used as the knockout construct is typically comprised of: (1) DNA from some portion of the gene (exon sequence, intron sequence, and/or promoter sequence) to be suppressed; and (2) a marker sequence used to detect the presence of the knockout construct in the cell. The knockout construct is inserted into a cell, and integrates with the genomic DNA of the cell in such a position so as to prevent or interrupt transcription of the native DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA).

The knockout construct nucleic acid sequence may comprise 1) a full or partial sequence of one or more exons and/or introns of the gene to be suppressed, 2) a full or partial promoter sequence of the gene to be suppressed, or 3) combinations thereof. Typically, the knockout construct is inserted into an embryonic stem cell (ES cell) and is integrated into the ES cell genomic DNA, usually by the process of homologous recombination. This ES cell is then injected into, and integrates with, the developing embryo.

Furthermore, knock-out mice having any phenotype that resembles a disease state may be used to screen or test therapeutic drugs that slow, modify, or cure conditions. As is known to the skilled artisan, a conditional knockout, wherein the gene is disrupted under certain conditions, is frequently used.

3. Transgenic Animals

It is further contemplated that transgenic animals are part of the present invention. A transgenic animal of the present invention may involve an animal created using methods of the invention.

In a general aspect, a transgenic animal is produced by the integration of a given transgene into the genome in a manner that permits the expression of the transgene, or by disrupting the wild-type gene, leading to a knockout of the wild-type gene. Methods for producing transgenic animals are generally described by Wagner and Hoppe (U.S. Pat. No. 4,873,191; which is incorporated herein by reference), Brinster et al. (1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

U.S. Pat. No. 5,639,457 is also incorporated herein by reference to supplement the present teaching regarding transgenic pig and rabbit production. U.S. Pat. Nos. 5,175,384; 5,175,385; 5,530,179, 5,625,125, 5,612,486 and 5,565,186 are also each incorporated herein by reference to similarly supplement the present teaching regarding transgenic mouse and rat production. Transgenic animals may be crossed with other transgenic animals or knockout animals to evaluate phenotype based on compound alterations in the genome.

F. Pharmaceutical Formulations and Administration Thereof

1. Pharmaceutical Formulations and Routes of Administration

Pharmaceutical compositions of the present invention comprise an effective amount of one or more candidate substance or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The compounds of the invention may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, systemically, subcutaneously, subconjunctival, intravesicularlly, mucosally, intrapericardially, intraumbilically, intraocularally, orally, locally, via inhalation (e.g., aerosol inhalation), via injection, via infusion, via continuous infusion, via localized perfusion bathing target cells directly, via a catheter, via a lavage, in cremes, in lipid compositions (e.g., liposomes), or by other method or any combination of the foregoing as would be known to one of ordinary skill in the art (see, for example, Remington's Pharmaceutical Sciences, 1990).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of a compound of the present invention. In other embodiments, the compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

The candidate substance may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine, or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. In certain embodiments, carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Additional formulations which are suitable for other modes of administration include suppositories. Suppositories are solid dosage forms of various weights and shapes, usually medicated, for insertion into the rectum, vagina, or urethra. After insertion, suppositories soften, melt or dissolve in the cavity fluids. In general, for suppositories, traditional carriers may include, for example, polyalkylene glycols, triglycerides, or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin, or combinations thereof.

2. Combination Therapy

In some embodiments, it is contemplated that the RAD51 modulators of the invention may be used in conjunction with DNA damaging agents as part of a treatment regimen. This process may involve contacting the cell(s) with the agents at the same time or within a period of time wherein separate administration of the agents produces a desired therapeutic benefit. This may be achieved by contacting the cell, tissue or organism with a single composition or pharmacological formulation that includes two or more agents, or by contacting the cell with two or more distinct compositions or formulations, wherein one composition includes one agent and the other includes another.

The compounds of the present invention may precede, be co-current with and/or follow the other agents by intervals ranging from minutes to weeks. In embodiments where the agents are applied separately to a cell, tissue or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the candidate substance. In other aspects, one or more DNA damaging agents may be administered or provided within 1 minute, 5 minutes, 10 minutes, 20 minutes, 30 minutes, 45 minutes, 60 minutes, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 1 week, 2 weeks, 3 weeks, 4 weeks, 5 weeks, 6 weeks, 7 weeks, or 8 weeks or more, and any range derivable therein, prior to and/or after administering the RAD51 modulator.

Various combination regimens of the agents may be employed. Non-limiting examples of such combinations are shown below, wherein a compound of the present invention is "A" and a second agent, such as a DNA damaging agent, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

In some embodiments, more than one course of therapy may be employed. It is contemplated that multiple courses may be implemented. In certain embodiments, a patient may have previously undergone radiation or chemotherapy for a cancer that turns out to be chemotherapy- or radiation-resistant. Alternatively, a patient may have a recurring cancer that is to be treated with a DNA damaging agent.

G. Organisms and Cell Source

Cells that may be used in many methods of the invention can be from a variety of sources. Embodiments include the use of mammalian cells, such as cells from monkeys, chimpanzees, rabbits, mice, rats, ferrets, dogs, pigs, humans, and cows. Alternatively, the cells may be from fruit flies, yeast, or *e. coli*, which are all model systems for evaluating homologous recombination.

Methods of the invention can involve cells, tissues, or organs involving the heart, lung, kidney, liver, bone marrow, pancreas, skin, bone, vein, artery, cornea, blood, small intestine, large intestine, brain, spinal cord, smooth muscle, skeletal muscle, ovary, testis, uterus, and umbilical cord.

Moreover, methods can be employed in cells of the following type: platelet, myelocyte, erythrocyte, lymphocyte, adipocyte, fibroblast, epithelial cell, endothelial cell, smooth muscle cell, skeletal muscle cell, endocrine cell, glial cell, neuron, secretory cell, barrier function cell, contractile cell, absorptive cell, mucosal cell, limbus cell (from cornea), stem cell (totipotent, pluripotent or multipotent), unfertilized or fertilized oocyte, or sperm.

Moreover, methods can be implemented with or in plants or parts of plants, including fruit, flowers, leaves, stems, seeds, cuttings. Plants can be agricultural, medicinal, or decorative.

H. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Etheno DNA-Based Assay for RAD51 Filament Formation

RAD51 filament formation is a well accepted critical step in the initiation of HR repair. Biochemical assays have been developed to measure RAD51 protein assembly on sites of single stranded DNA (ssDNA) in vitro. Most studies have used etheno DNA (also called epsilon DNA) as the substrate in this assay. Etheno DNA is formed in a chemical reaction that has been recognized since the early 1970's (Secrist et al., 1972; Barrio et al., 1972). In this reaction, single stranded DNA (commonly phage DNA or an oligonucleotide) is incubated with choroacetaldehyde in a low pH solution. The chemical intermediates in this reaction are matured by further incubation at elevated temperatures (Krzyzosiak et al., 1981). This generates a chemical modification of the cytidine and adenosine bases, resulting in fluorescent ethenocytidine and ethenoadenosine derivatives.

Alternatively, oligonucleotides can be directly synthesized in the etheno form (typically poly-etheno dA). Numerous studies over the past 25 years have reported that the fluorescent signal emitted by etheno DNA is increased when bound by proteins. The level to which proteins bind etheno DNA can be quantitatively measured by fluorescence spectrophotometry. When saturated with an excess of a DNA-binding protein, the fluorescence above baseline increases approximately 2-4 fold. This technique has been used widely to characterize the conditions and kinetics for a variety of DNA-interacting proteins and compounds (Zaitseva et al., 1999; Menetski and Kowalczykowski, 1985; Sugiyama et al., 1997). The inventors have used this technique to confirm the activity of purified RAD51 protein and lack thereof in the RAD51 (F86E) mutant.

Example 2

Fluorescence Polarization Assay for RAD51 Filament Formation

Figure 2A:
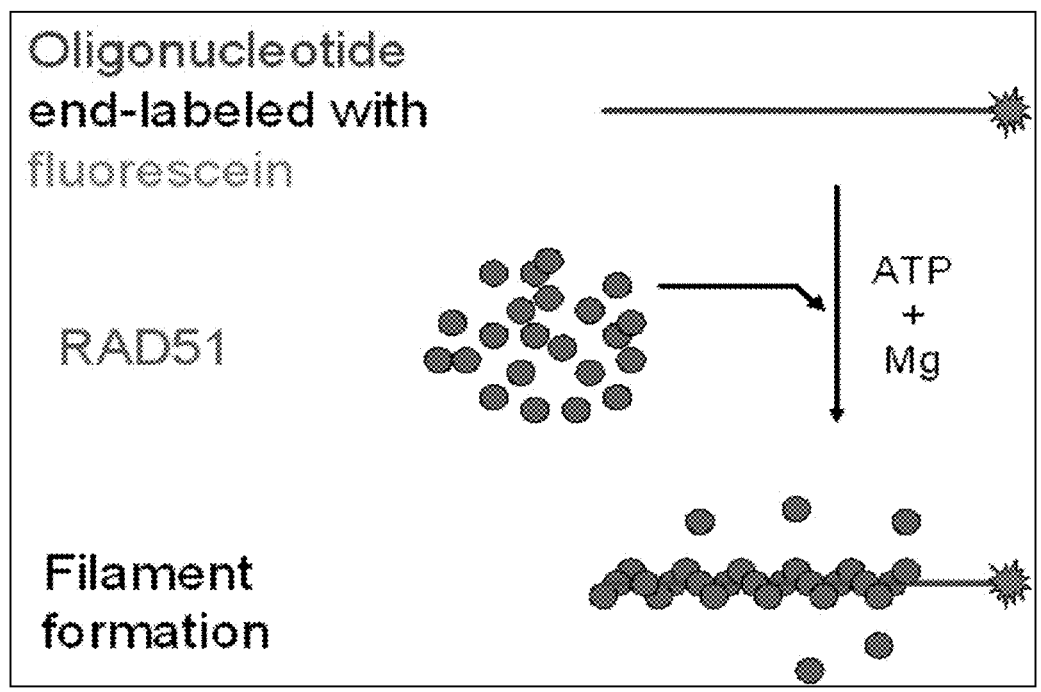
FIGS. 2A-2B.
Figure 2A:
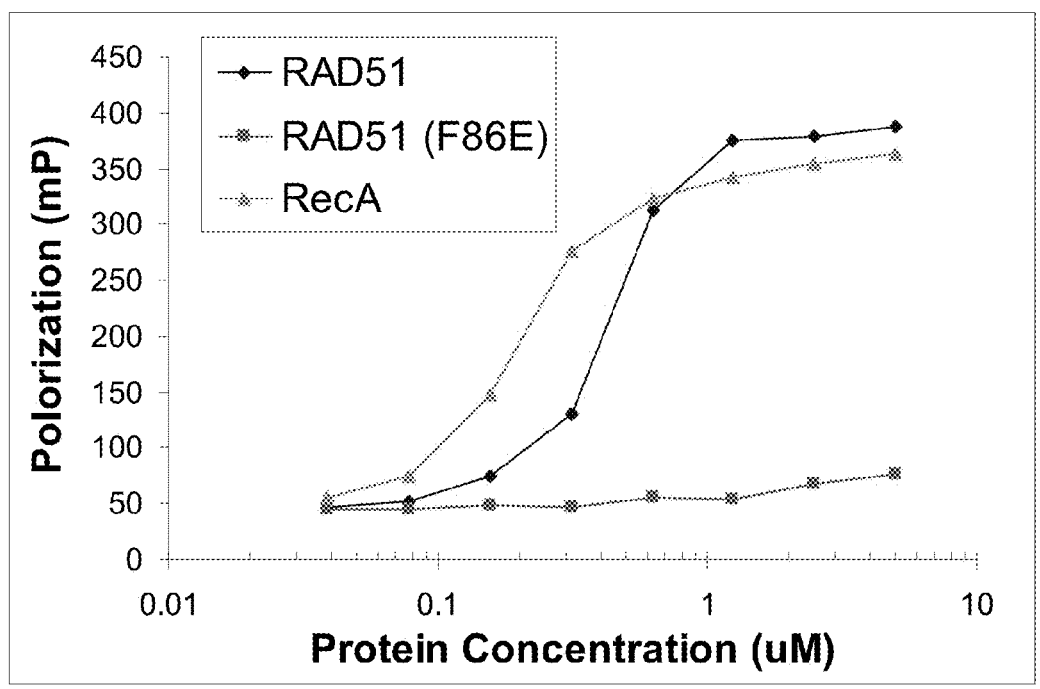
Figure 2B:
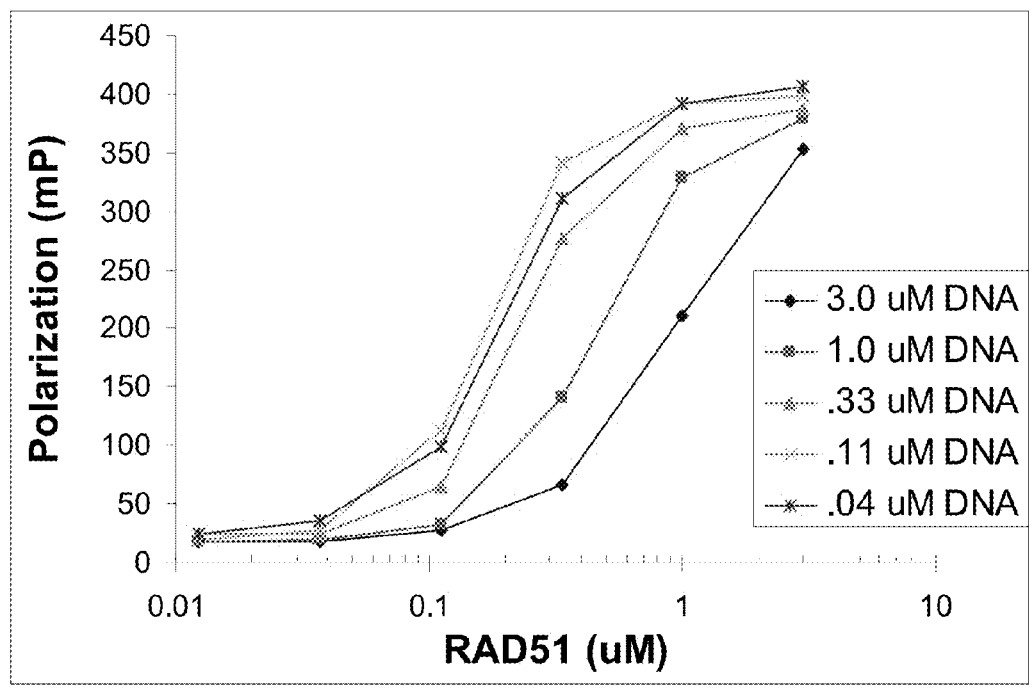
Figure 2B:
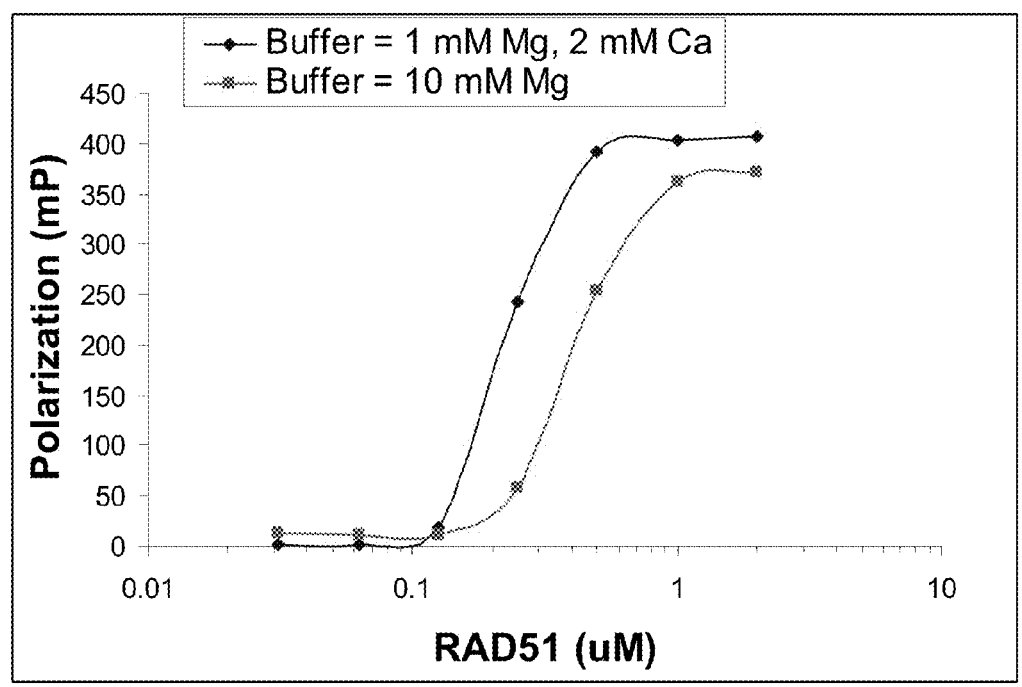

RAD51 filament formation can also be studied using oligonucleotides that are end-labeled with a fluorescent tag. Binding of proteins to this substrate DNA can be detected as an increase in anisotropy (or polarization) of the fluorescent tag. This method has been used to monitor the DNA-binding activity of yeast RAD51 (Kim et al., 2001) and RecA (Wittung et al., 1997; Ellouze et al., 1999), which is the eukaryotic homolog of RAD51. In this example, this method was modified so that very small sample volumes (30 µl) can be monitored in a high-throughput scale, using 384-well plates and a fluorescent plate reader. A comparison of the two methods shows essentially identical results in term of RAD51 binding. However, the fluorescence polarization assay is less expensive, faster, and it generates results with superior signal to background ratios (FIGS. 2A-2B). By varying the amount of substrate DNA, a threshold of approximately 0.1 µM RAD51 protein is required for in vitro filament formation in this system. Furthermore, RAD51 filament formation in this assay is more efficient and/or more stable in buffers containing calcium ions. This is consistent with a prior report showing that calcium stimulates yeast RAD51 in this fluorescence polarization assay, and renders filaments more stable in high salt buffers (Kim et al., 2001). Another report showed that calcium inhibits ATP hydrolysis by human RAD51, resulting in stabilization of filaments and stimulation of strand exchange activity (Bugreev and Mazin, 2004).

Example 3

Figure 3:
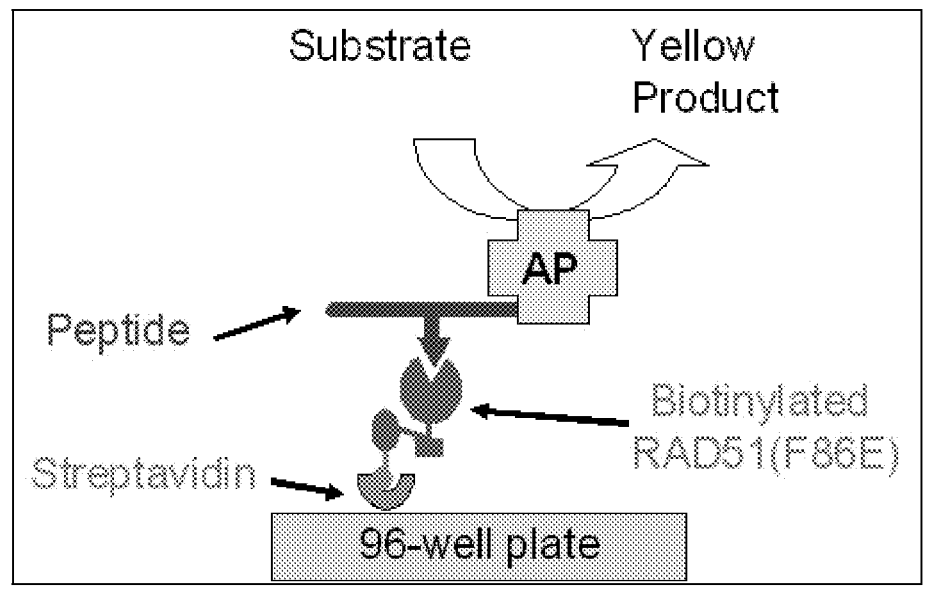
FIG. 3. (Top) Schematic of AP-peptide fusion assay using RAD51(F86E) as the protein bait. (Bottom) Wells were coated with various bait proteins (biotinylated RAD51, biotinylated RAD51(F86E), or nothing). Binding affinities of two AP-peptide fusions were compared.
Figure 3:
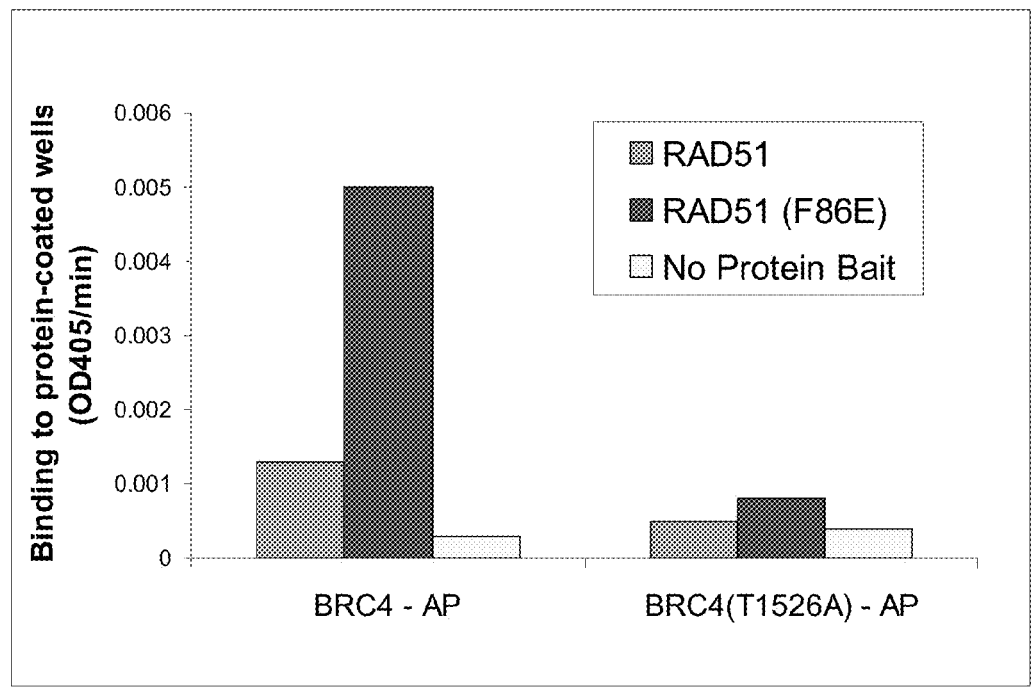

Peptide-Alkaline Phosphatase (AP) Fusion-Based Assay for Detection of RAD51-Protein Interactions An assay to quantitatively measure protein-protein interactions using a peptide-alkaline phosphatase (AP) fusion system was developed (Han et al., 2004). In this system, oligonucleotide duplexes encoding peptide sequences are cloned into an AP expression plasmid (pEZ707, gift of Dr. Brian Kay). The plasmids are transformed into BL21(DE3) bacteria, expressed, and purified. Streptavidin-coated plates (96-well format) are coated with a biotinylated bait protein. The binding of peptide-AP fusion proteins to bait-coated wells are quantified with a plate reader following incubation with an alkaline phosphatase substrate (FIG. 3, left). This system allows for a large number of peptide sequences to be rapidly screened.

Example 4

Assay for Measuring Interactions Between RAD51 and BRC4

A fusion protein was prepared, such that full-length BRC4 (BRCA2 residues 1511-1579) was linked to the N-terminus of alkaline phosphatase. This 69 amino acid wild-type polypeptide exhibited binding to RAD51-coated wells and minimal interaction with uncoated wells (FIG. 3, right). The binding was about 4-fold stronger to RAD51(F86E) coated wells, relative to wild-type RAD51 coated wells. This F86E mutation is known to impair RAD51's ability to self-associate (Pellegrini et al., 2002; Yu et al., 2003); consequently the RAD51(F86E) protein probably serves as a better 'bait' in this assay because it is composed primarily of protein monomers. A mutant BRC4-AP fusion was also prepared containing an alanine substitution at a residue corresponding to tyrosine-1526 of BRCA2. This BRC4(T1526A) mutant showed markedly reduced binding, relative to wild type BRC4. This result is consistent with previous studies that examined analogous T to A mutations in BRC repeats using other types of assays (Chen et al., 1999; Davies et al., 2001).

Example 5

Determination of the Minimal Length of BRC4 Sufficient for Binding to RAD51

As discussed previously, the conditional expression of BRC4 polypeptide in a breast cancer cell line results in a hypersensitivity to DNA damage (Chen et al., 1999). One possible consideration is for inhibiting HR with a BRC4-based peptide that can be synthetically prepared and directly delivered from tissue culture media into cells. An expected problem with this plan relates to the relatively large size of BRC4 (69 amino acids), which could present challenges in terms of large-scale synthetic peptide preparation. However, studies focusing on other BRC repeats have shown that the entire polypeptide may not always be required for RAD51 binding (Chen et al., 1999; Chen et al., 1998; Wong et al., 1997).

Figure 4:
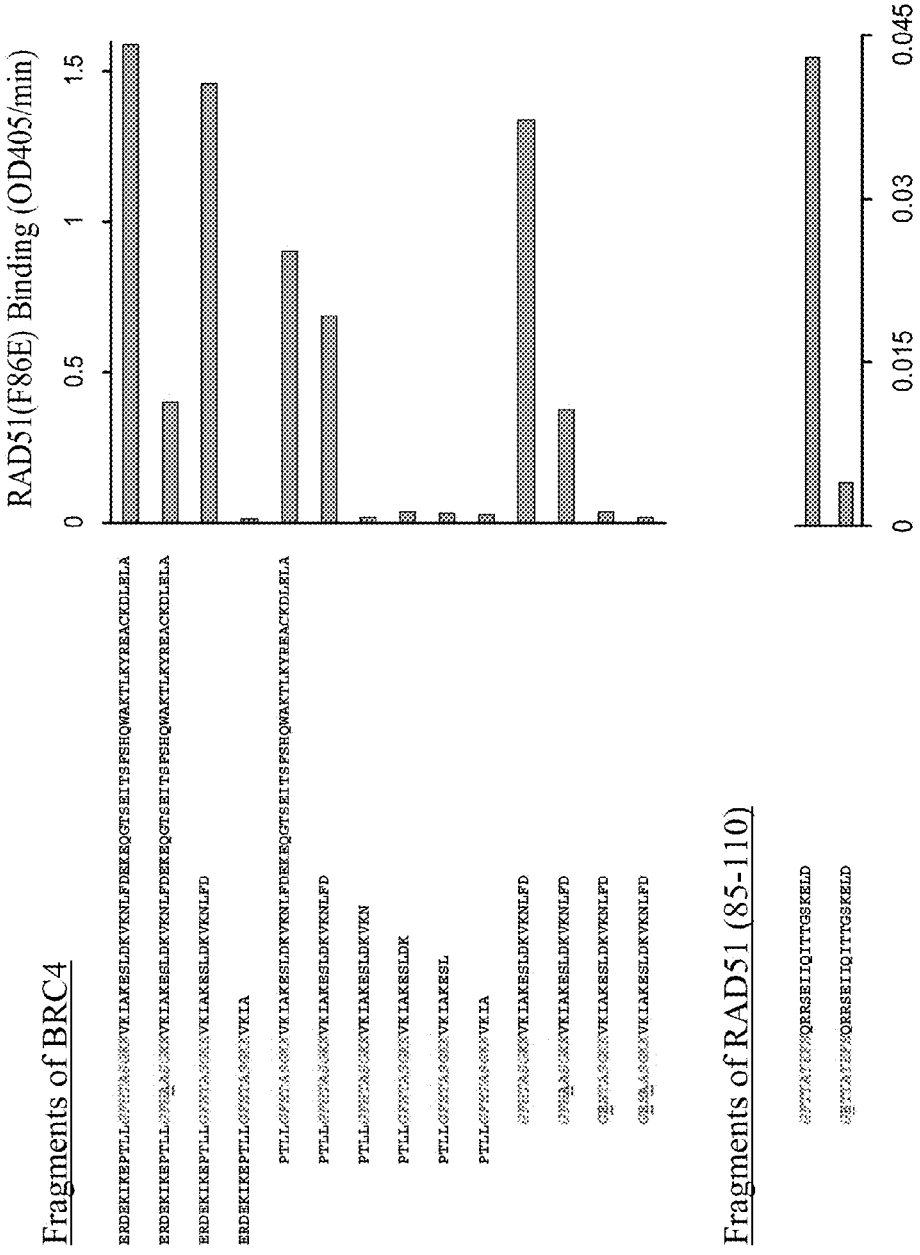
FIG. 4. Using an AP-peptide fusion strategy, stepwise truncations of the BRC4 peptide were performed to determine the minimal length sufficient for binding to RAD51(F86E). The predicted interaction sequence is displayed in green italics. A corresponding RAD51 peptide was generated. Point mutations are displayed in red underlined text, including the T1526A and F1524E substitutions in BRC4 and the F86E substitution in the RAD51 fragment (SEQ ID NOS:1-16).

For this reason, the AP-fusions system was used to determine the minimal length of BRC4 sufficient for binding to RAD51. Several AP-fusion proteins were prepared such that residues were truncated from either side of BRC4 in a stepwise manner (FIG. 4). These were tested for the ability to bind RAD51(F83E) coated wells. These results demonstrate that C-terminal truncations beyond the aspartic acid residue (corresponding to amino acid 1547 of BRCA2) markedly reduce binding; while smaller C-terminal truncations had no significant impact on binding. Similarly, up to 12 residues could be truncated from the N-terminus of BRC4 without impacting binding. N-terminal truncations were not attempted beyond the glycine (corresponding to amino acid 1523 of BRCA2), since this region contains the conserved oligomerization motif. Thus the minimal length sufficient for binding was determined to be amino acids 1523-1547 of BRCA2.

An alanine substitution at a residue corresponding to tyrosine-1526 of BRCA2 resulted in markedly reduced binding of this minimal peptide, consistent with the mutagenesis results in full length BRC4. An F1524E substitution in BRC4 resulted in even greater loss of RAD51 binding. A peptide fragment of RAD51 (residues 85-110) corresponding to the minimal BRC4 peptide was prepared in the AP fusion system. This peptide had considerably less binding to full length RAD51(F86E), relative to the minimal BRC4 peptide. Similar to the BRC4 result, an analogous mutation (F86E) in the RAD51 fragment reduced binding to full-length RAD51 (F86E).

Example 6

Identification of RAD51 Enhancers

The assay of Example 2 was used to serve in the screen of a small-molecule chemical library for compounds that stimulate RAD51 filament formation. For the screen conditions that resulted in 50% saturation of the FP endpoint were selected. Multiple positive (+RAD51) and negative (RAD51) controls were tested, and these readings were tested using the statistical method described by Zhang et al. (1999), which evaluates the suitability of an HT assay. The assay as described has a Z-factor of 0.82, validating it as an excellent assay for HT screening.

Figure 5:
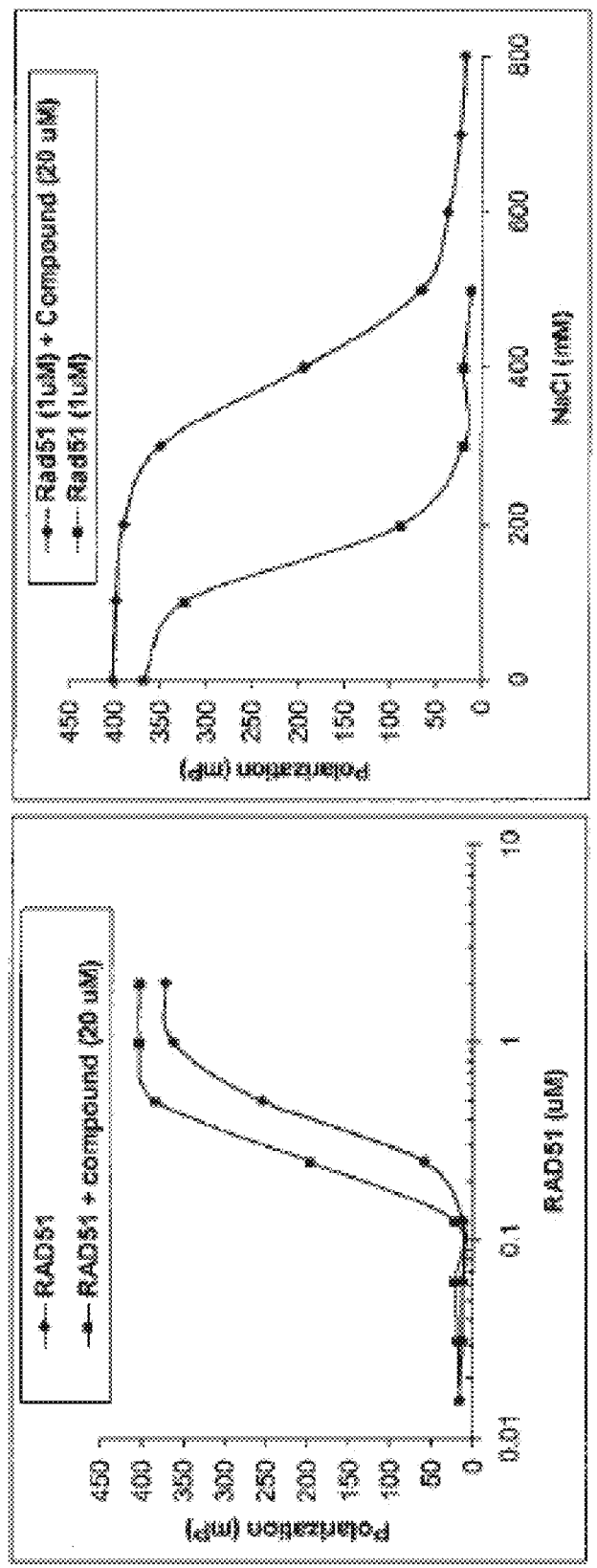
FIG. 5. (Left) RAD51-enhancery compound 45488 (also called compound 5253121, or RS-1) (at 20 µM) enhances filament formation. (Right) The compound stabilizes RAD51 filaments in the presence of high salt concentrations.

A naïve 10,000 compound library of small molecules (Chembridge DIVERSet collection) was screened. A 'mixed compound' screening strategy was used, wherein each reaction tested a mixture of 8 compounds. When filament stimulation was achieved for any given compound mixture, the 8 compounds from that mixture were individually tested using the same compound concentration. This identified 3 small molecule compounds that stimulate RAD51 filament formation by at least 50% (FIGS. 8A-8E, compounds 45488 (also called compound 5253121), 43783 and 41936). Further study of the most the active compound (45488) (also called compound 5253121) confirmed that it enhances RAD51 filament formation, and that it protects these filaments from buffers containing high salt concentrations (which typically destabilize RAD51 filaments). Imaging with electron microscopy has confirmed that the increases in measured FP are, in fact, due to compound-stimulated filaments with long track lengths (FIG. 5). These experiments have been repeated with RecA protein (the bacterial ortholog of RAD51) and demonstrated no stimulation of filament formation, suggesting the compound effect is specific to RAD51.

Figure 6:
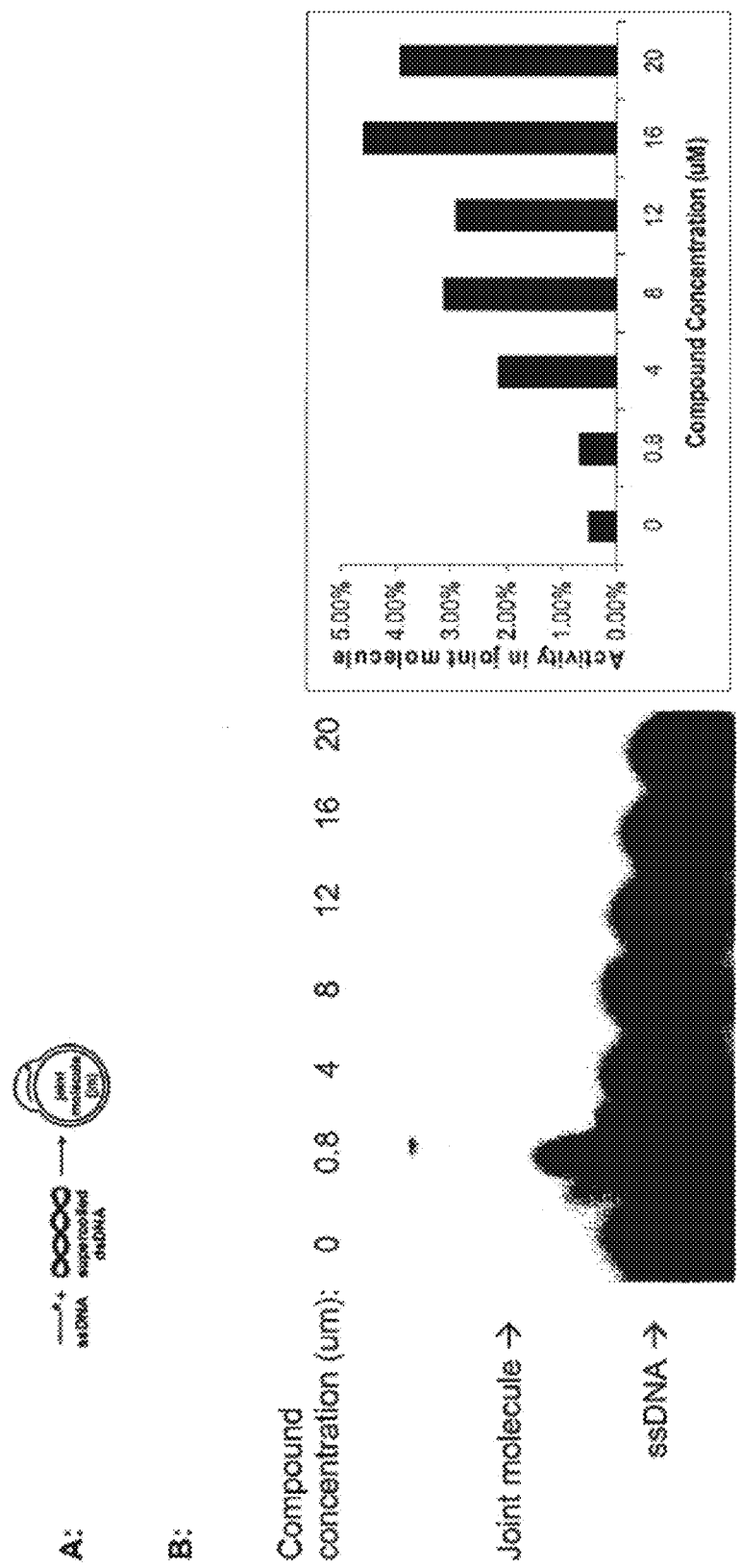
FIGS. 6A-6B. Schematic of the strand invasion (D-loop) assay. (B) The D-loop assay was performed using 0.8 µM RAD51 in a buffer that does not support joint molecule formation (1 mM ATP, 1 mM MgOAc). Addition of the compound (45488, also called compound 5253121, or RS-1) lead to a concentration dependent increase in joint molecule formation (gel on left, quantification on right).

This compound was also tested using an assay that tests strand invasion, a later step in HR (FIG. 6A). Briefly, 15 µl reaction volumes included a DNA strand exchange protein (0.8 µM) that was pre-incubated for 5 min at 37° C. with 1 µM (nucleotide concentration) $^{32}$P-labeled oligonucleotide in a reaction buffer containing 20 mM Hepes (pH 7.5), 1 mM DTT, 2 mM nucleotide cofactor, and 1 mM $MgCl_2$, and various concentrations of RS-1. For experimental buffer conditions that included calcium, 1 mM $CaCl_2$ was present in addition to (in the case of hRAD51) or in the place of (in the case of RecA and scRAD51) the 1 mM $MgCl_2$. Conditions with scRAD51 additionally contained 110 nM scRAD54. Following this initial binding reaction, 10 µl of 19.75 µM (base pair concentration) supercoiled homolog-containing target plasmid DNA (pRS306) was next added along with sufficient magnesium acetate to give a final concentration of 10 mM. DNA substrates were allowed form a homology dependent association (or 'D-loop'), and reactions were stopped with SDS and proteinase K. The resulting DNA was separated on 1.3% agarose gels, transferred onto nitrocellulose membranes, analyzed by phosphorimaging, and quantified with ImageJ 1.37v software (NIH).

These experiments demonstrated that the compound is capable of stimulating DNA strand invasion activity of RAD51 (FIG. 6B). These experiments were repeated using other recombinase proteins (bacterial RecA and yeast DMC1) in the place of human RAD51. The compound had no effect on RecA and demonstrated some inhibition of DMC1. This further supports the inventor's belief that the compound's enhancery effect is RAD51 specific.

An additional 20 compounds were identified in the Cambridge library that shared varying degrees of structural similarity to compound 45488 (also called compound 5253121). These are also shown in FIGS. 8A-8E.

Example 7

Cell Survival Study Using a RAD51 Enhancer

Normal Diploid Fibroblasts

Figure 7A:
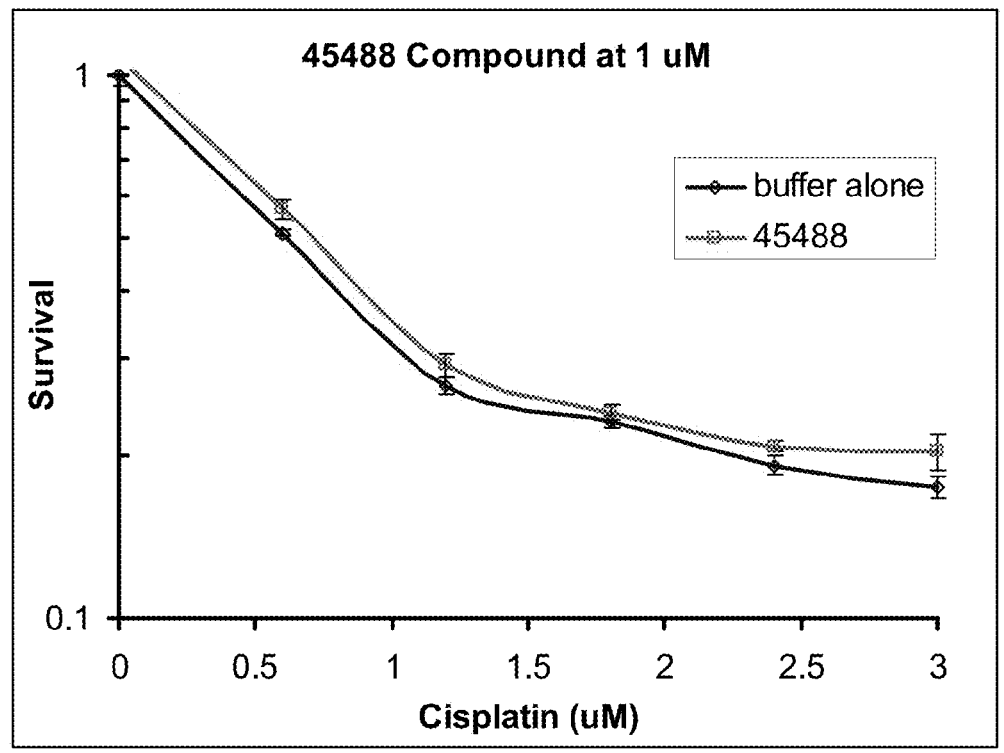
FIGS. 7A-7C. Cell survival study using a RAD51 enhancer (45488) (also called compound 5253121, or RS-1) at various concentrations and normal diploid fibroblasts.
Figure 7A:
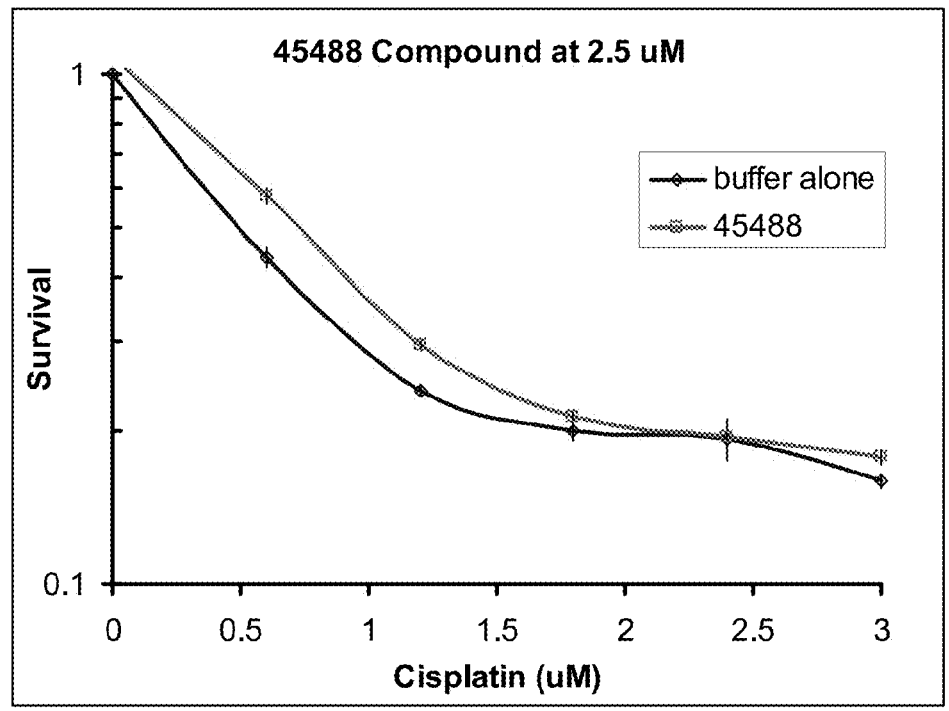
Figure 7B:
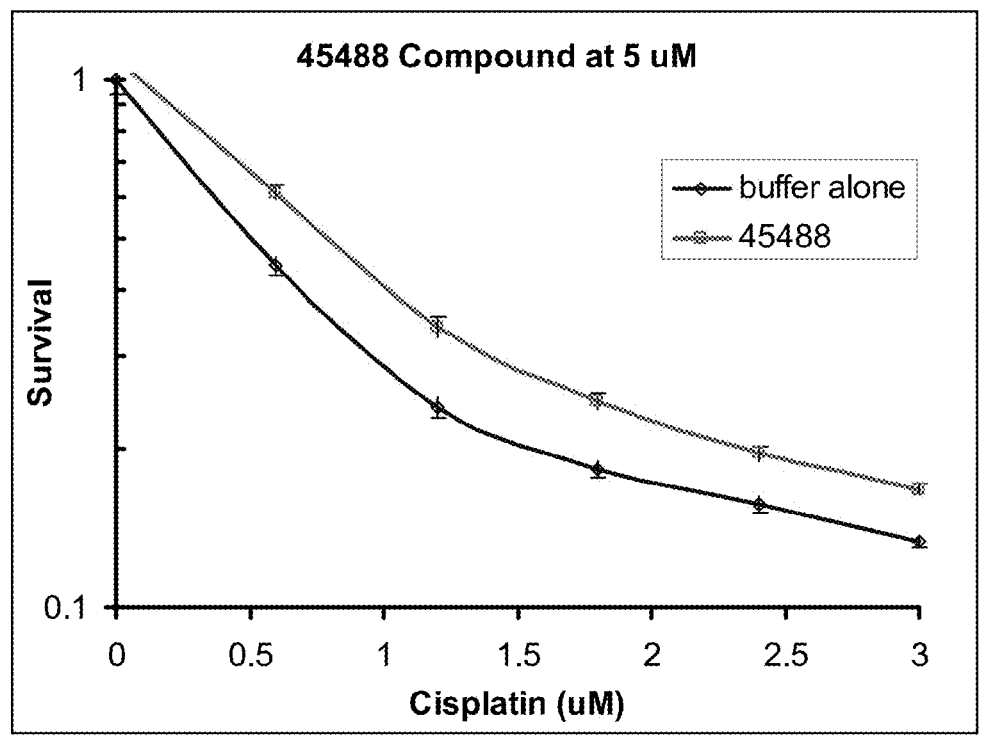
Figure 7C:
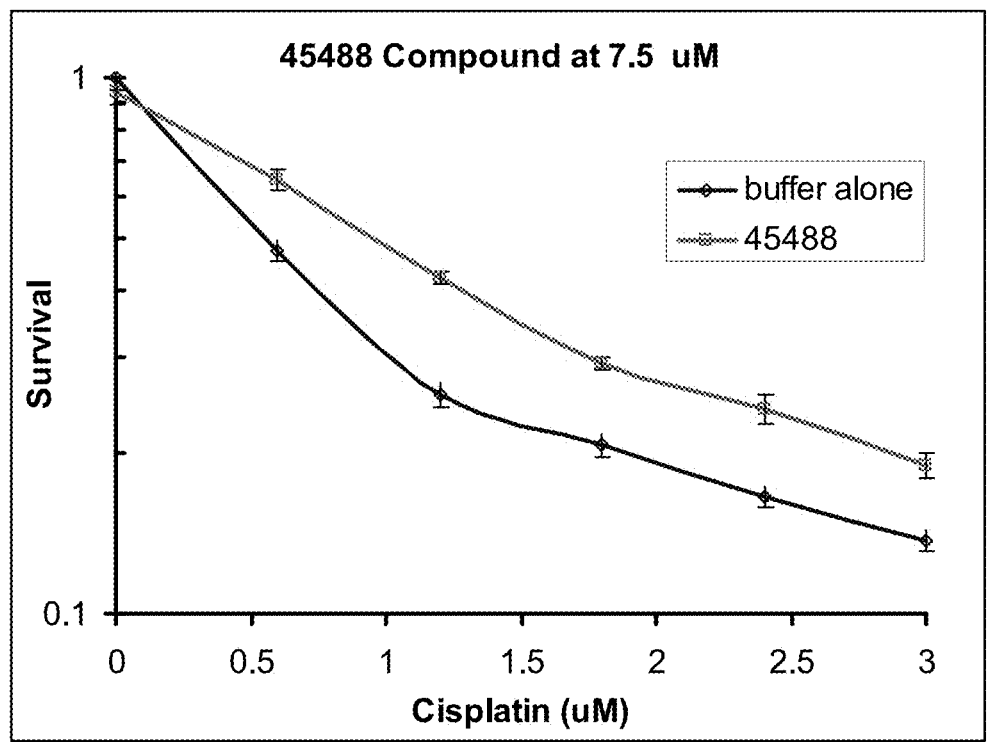
Figure 7C:
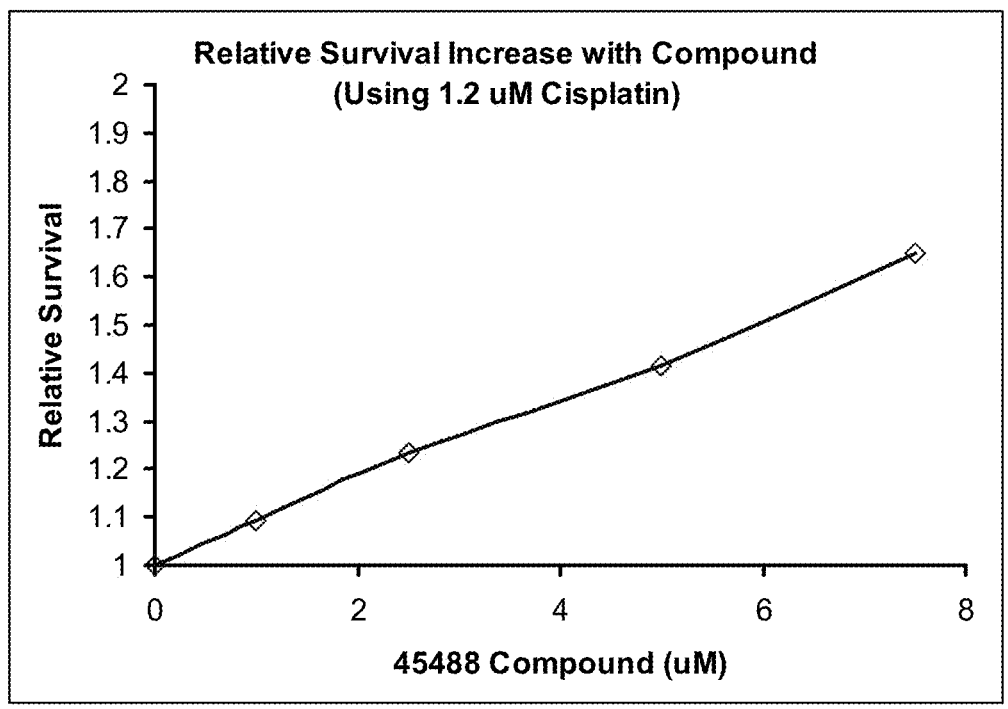
Figure 8A:
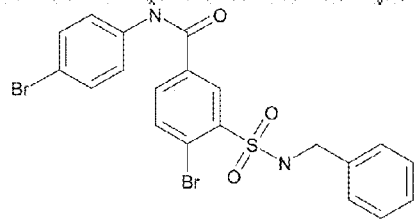
FIGS. 8A-8E. Structures of various RAD51 enhancers of the present invention.
Figure 8A:
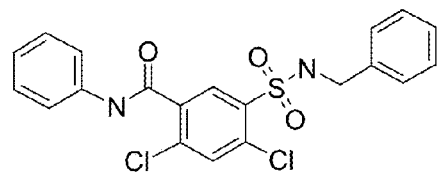
Figure 8A:
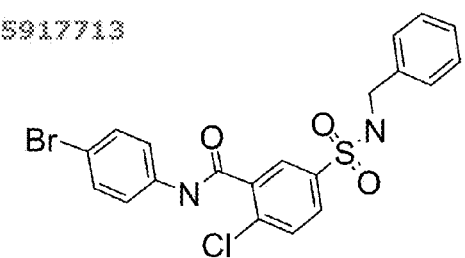
Figure 8A:
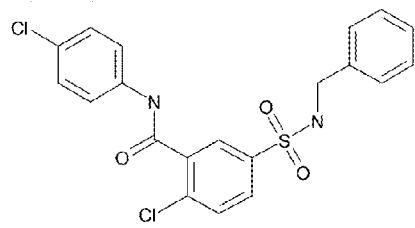
Figure 8A:
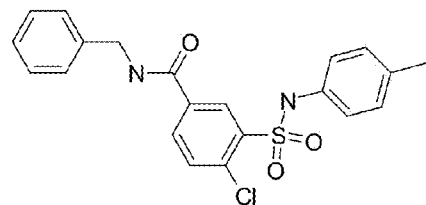
Figure 8A:
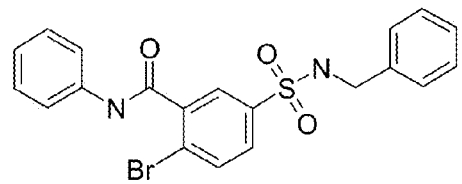
Figure 8A:
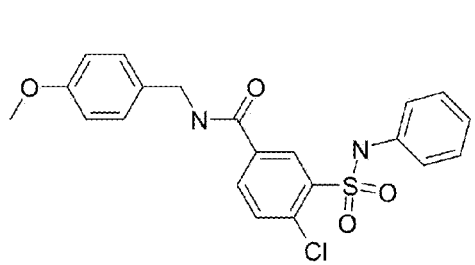
Figure 8B:
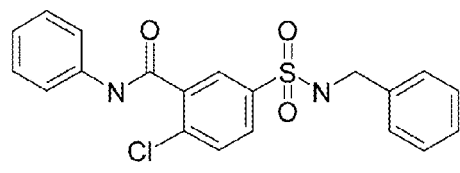
Figure 8B:
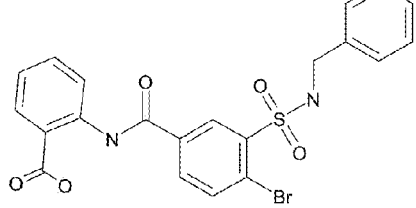
Figure 8B:
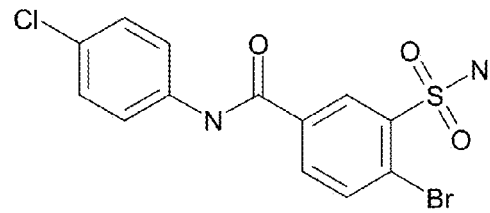
Figure 8B:
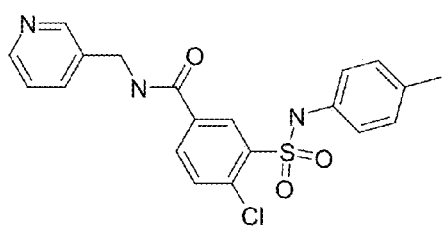
Figure 8B:
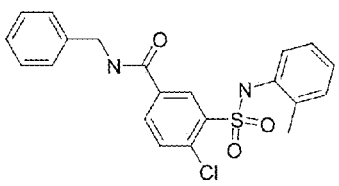
Figure 8B:
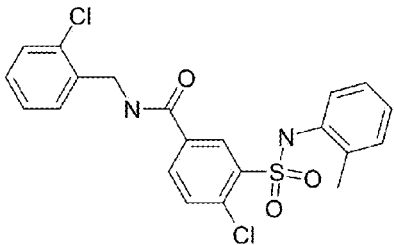
Figure 8B:
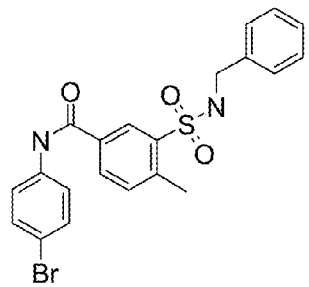
Figure 8B:
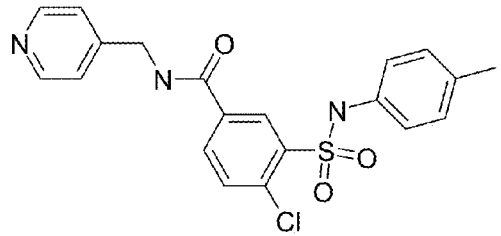
Figure 8C:
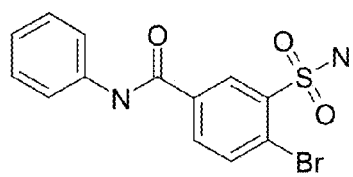
Figure 8C:
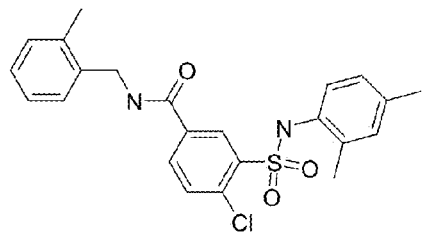
Figure 8C:
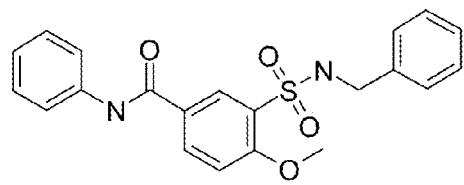
Figure 8C:
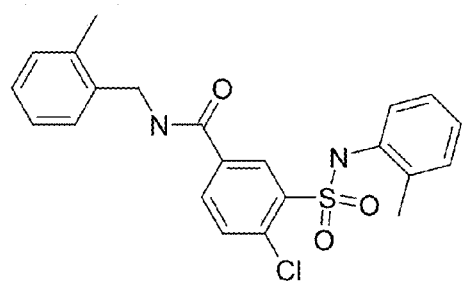
Figure 8C:
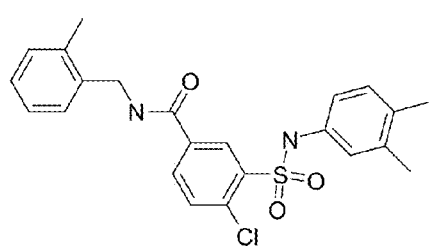
Figure 8C:
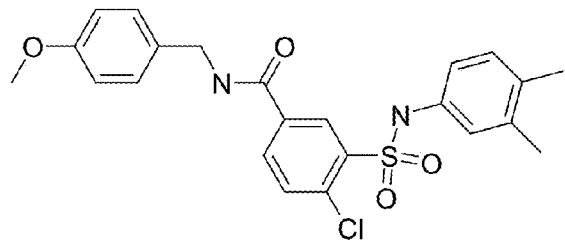
Figure 8D:
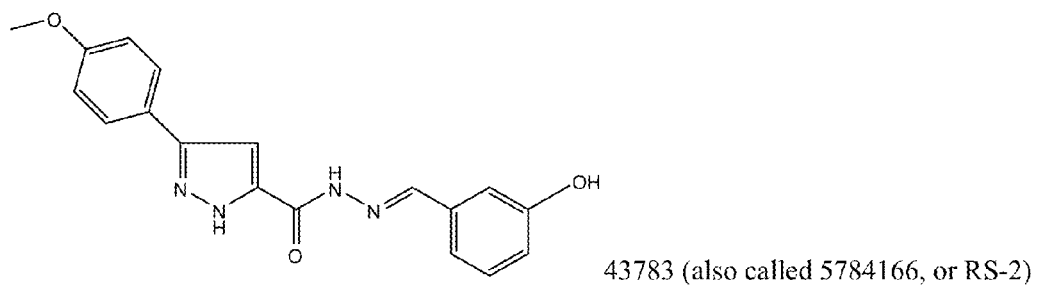
Figure 8D:
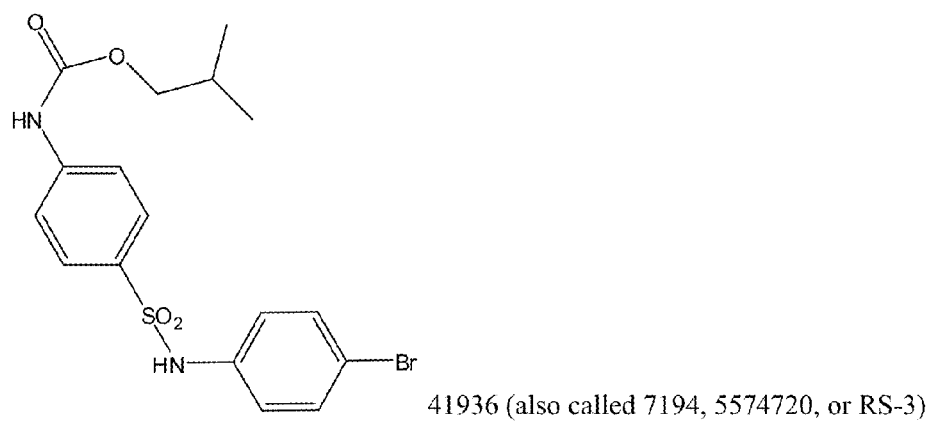
Figure 8D:
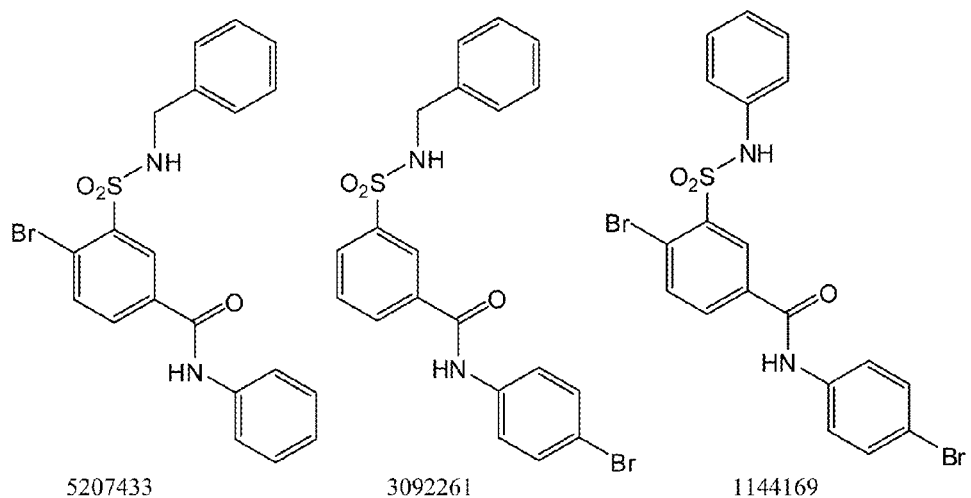
Figure 8E:
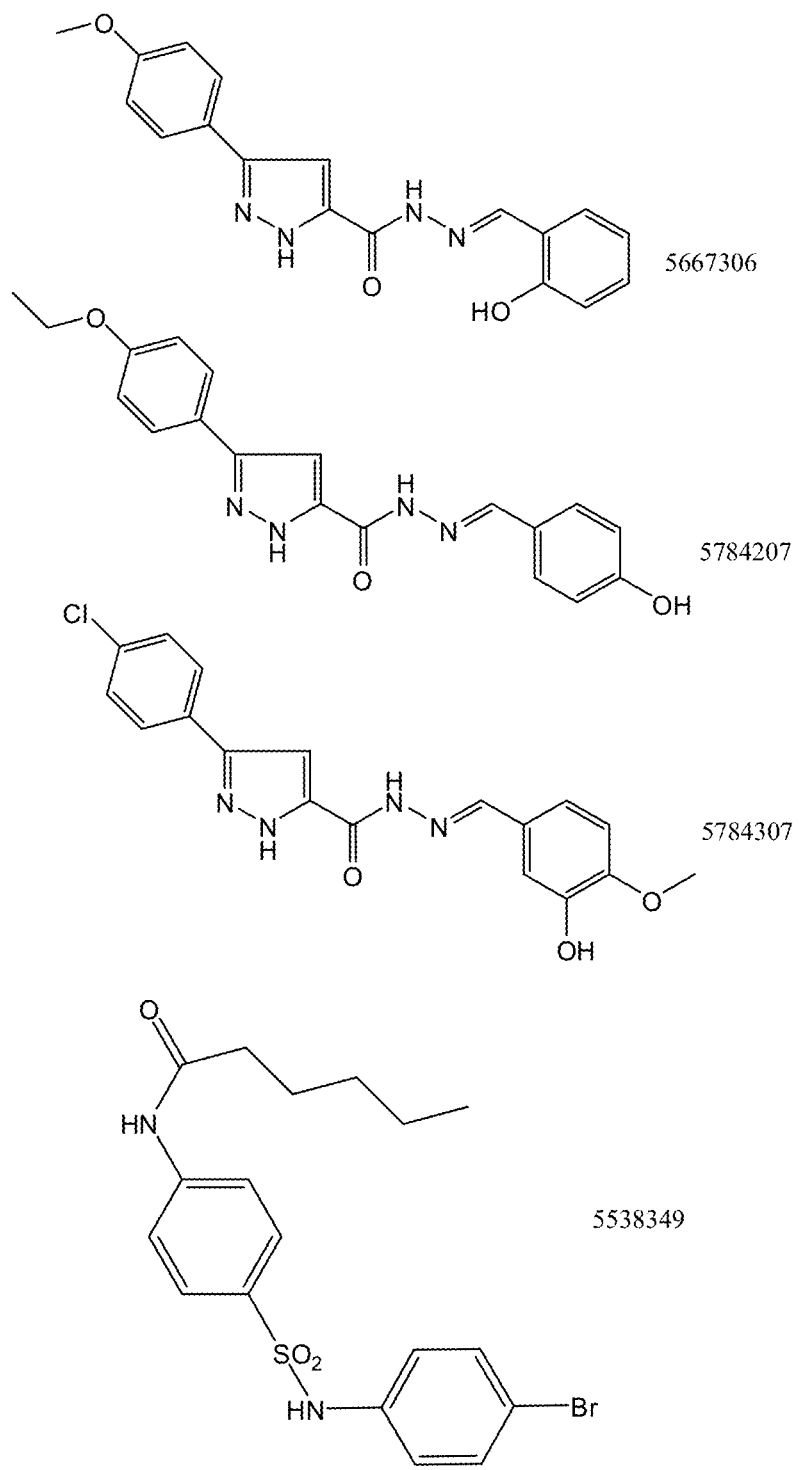

Normal diploid fibroblasts were plated in 96-well format (900 cells/well) and were incubated for 24 hrs with various doses of cisplatin and 45488 compound (also called compound 5253121) (administered simultaneously). Drugs were then removed and replaced with normal media. Cells were allowed to grow for 6 days, and were then fixed and stained with sulforhodamine B (SRB). The amount of surviving cells was quantified as a function of OD(564) with a plate reader (FIGS. 7A-7C). Each data point represents the mean of 6 repeat wells, and error bars represent the standard error of the mean (SEM).

Example 8

Fluorescence Polarization Assay Using RAD51 Enhancers

Figure 10:
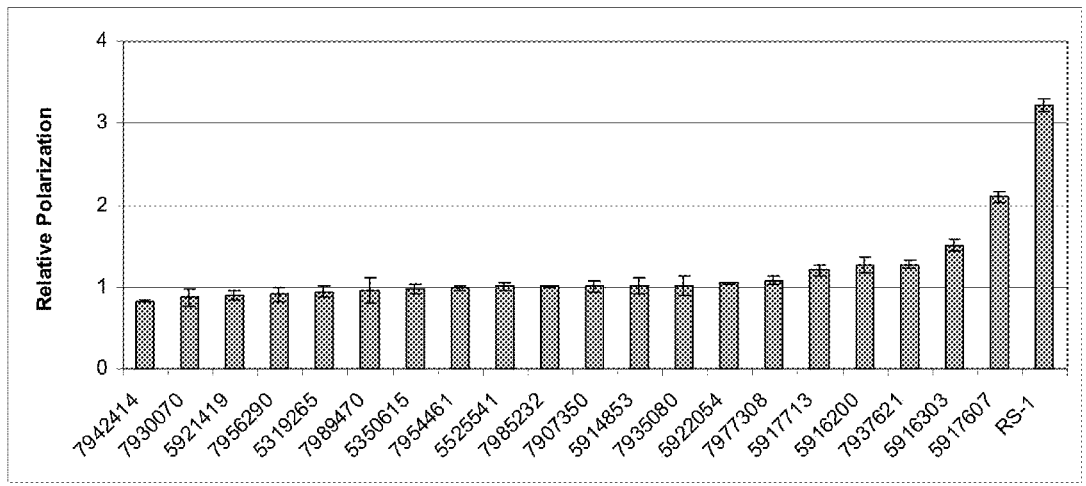
FIG. 10. Fluorescence polarization was evaluated for a number of compounds to identify RAD51 enhancers.
Figure 11:
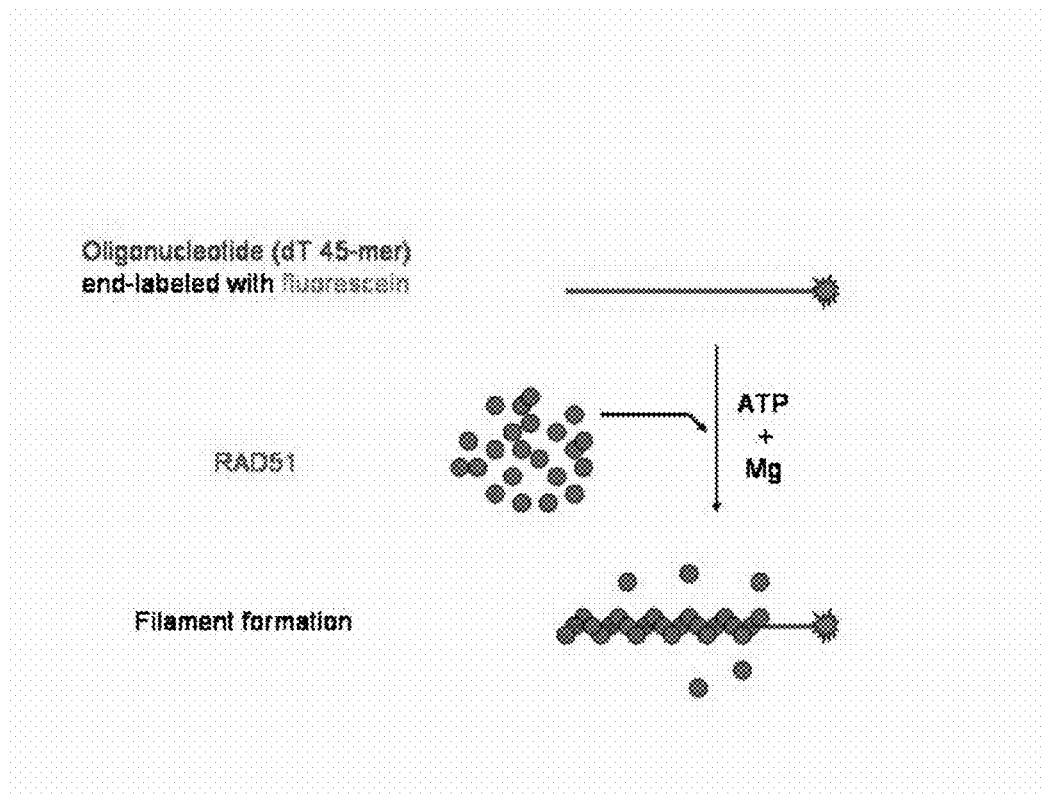
FIG. 11. Fluorescence polarization, which is an assay for filament formation, was evaluated using different concentrations of RAD51 protein.
Figure 11:
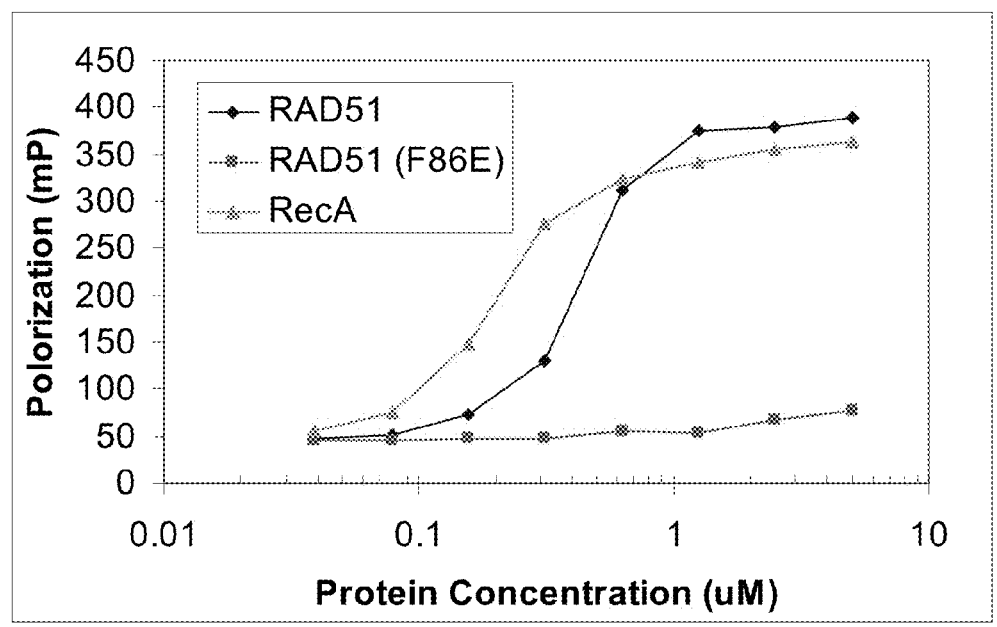

The compounds shown in FIGS. 8A-8E were tested using the assay of Example 2. The results are shown in FIG. 10.

Example 9

Identification of RAD51 Inhibitors

The assay of Example 2 was used to serve in the screen of a small-molecule chemical library for compounds that inhibit RAD51 filament formation. The assay performed well in black polystyrene 384-well plates. FP readings were very reproducible with reaction volumes in the 10-100 µl range, and 100 µl was typically used. The HT screen used small molecules from the ChemBridge library collections (10,000 compound DIVERSet collection). Compounds are stored at 0.5 mg/ml concentrations; the molecular weights vary so the average compound stock concentration is 14.7 mM. The assay was optimized such that the positive control FP reading was ~50% of maximal reaction saturation; the RAD51 protein concentration was 0.3 uM and the fluorescein-labeled DNA is at 0.1 uM (nucleotide concentration). At these concentrations the positive (+RAD51) and negative (−RAD51) controls were tested in 50 independent wells each. The average FP readings for positive control and negative control are 344 mP (SD=13.4) and 27 mP (SD=5.3), respectively. These readings were tested using the statistical method described by Zhang et al, which evaluates the suitability of an HT assay (Zhang et al., 1999). The performance of the assay as described has a Z-factor of 0.82, suggesting that it is an excellent assay for the proposed HT screen.

Figure 9A:
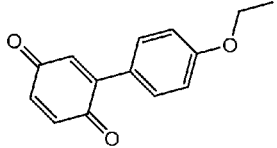
Figure 9A:
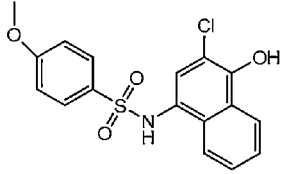
Figure 9A:
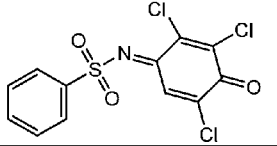
Figure 9A:
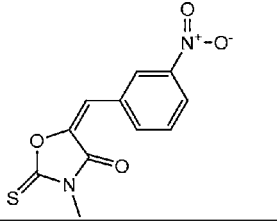
Figure 9A:
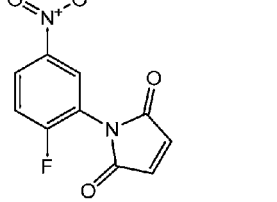
Figure 9A:
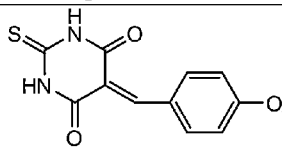
Figure 9A:
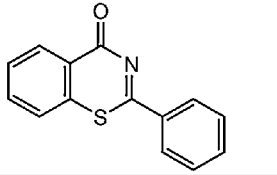
Figure 9B:
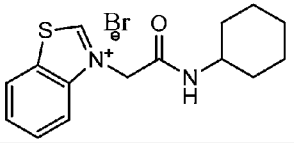
Figure 9B:
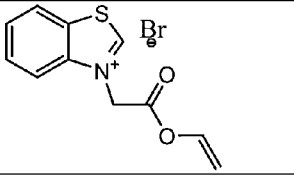
Figure 9B:
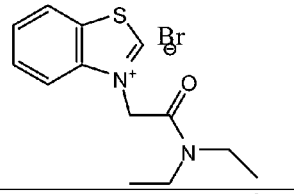
Figure 9B:
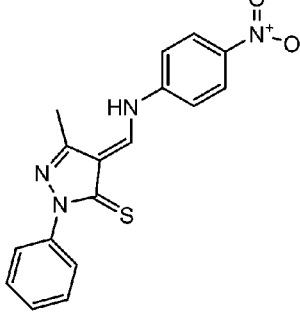
Figure 9B:
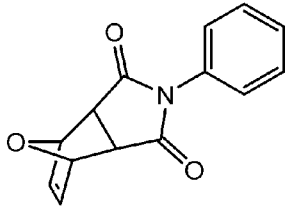
Figure 9B:
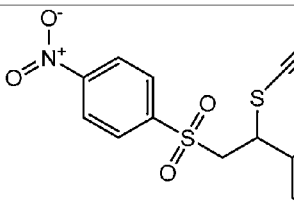
Figure 9C:
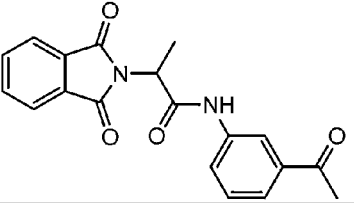
Figure 9C:
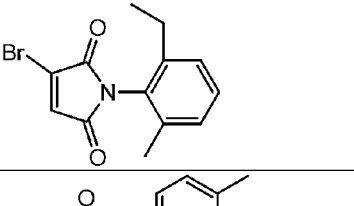
Figure 9C:
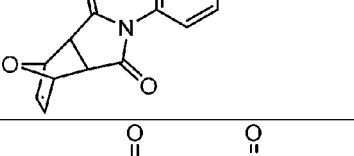
Figure 9C:
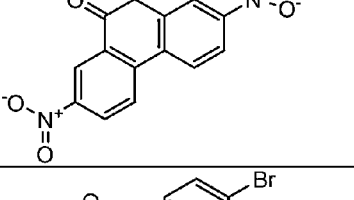
Figure 9C:
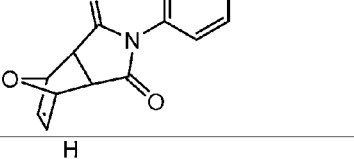
Figure 9C:
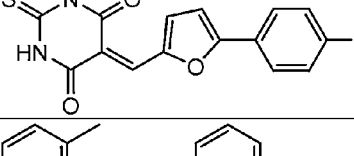
Figure 9C:
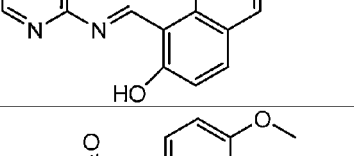
Figure 9C:
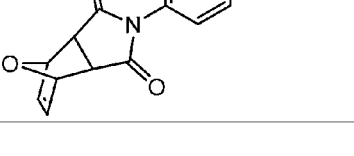
Figure 9E:
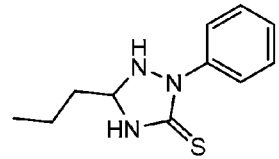
Figure 9E:
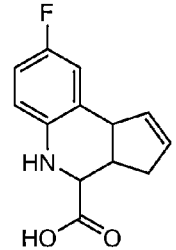
Figure 9E:
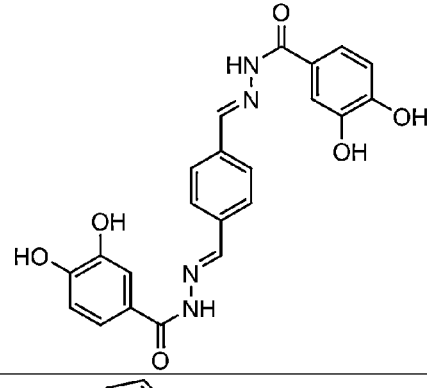
Figure 9E:
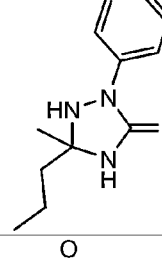
Figure 9E:
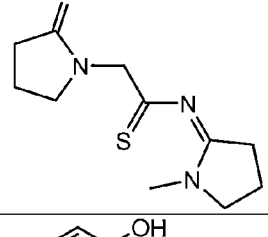
Figure 9E:
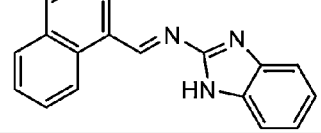

The inventors used a 'mixed compound' screening strategy, so each well in the test plate contained a mixture of 8 compounds. This strategy has the advantage of higher throughput than single-compound screening; it is based on the low statistical probability that any one well will contain both an inhibitory and a enhancery compound, rendering their effects undetectable. Plates of compound mixtures were prepared such that starting compound concentrations would be 6.25 µg/ml in each reaction (average of 18.3 µM). The compounds were manually added to RAD51 protein in reaction buffer with a multi-channel pipettor, and the mixture was pre-incubated at room temperature for 5 minutes. The DNA substrate is then added, plates are incubated for 30 minutes at 37°, and FP is measured. FP data points from each test well were normalized in two ways: 1) to the corresponding positive control for each plate; 2) to the median compound FP value for each plate. When filament inhibition was achieved with a compound mixture, the 8 compounds from that mixture were individually tested. This screen identified 3 compounds that enhance filament formation by at least 50%. It also identified 72 compounds with at least 55% inhibition of filament formation in the standard buffer containing 10 mM $Mg^{2+}$ (FIG. 9A-9S). These 72 compounds were re-tested in a buffer containing 1 mM $Mg^{2+}$ and 2 mM $Ca^{2+}$. Reactions in this more stringent buffer condition identified 28 of the 72 that were capable of inhibiting filament formation by 60% or more (Table 3):

TABLE 3

| Plate location | % Inhibition |
| --- | --- |
| 412 10 3 | 65.5139 |
| 460 6 2 | 69.88384 |
| 448 6 2 | 72.28592 |
| 470 5 4 | 73.69906 |
| 487 8 5 | 74.4119 |
| 497 6 8 | 76.83156 |
| 487 8 7 | 78.70403 |
| 534 9 8 | 86.57293 |
| 487 8 6 | 89.31386 |
| 487 11 4 | 89.63514 |
| 474 11 4 | 89.97149 |
| 524 5 8 | 92.53421 |
| 474 5 5 | 93.80428 |
| 469 6 7 | 94.15568 |
| 461 4 7 | 94.31381 |
| 509 8 6 | 95.112 |
| 474 11 2 | 95.49854 |
| 448 6 7 | 95.50858 |
| 520 7 2 | 96.116 |
| 520 5 1 | 96.27915 |
| 520 9 8 | 96.47493 |
| 497 3 5 | 97.00204 |
| 467 6 2 | 97.23045 |
| 472 8 3 | 97.26559 |
| 452 6 8 | 97.35595 |
| 452 6 4 | 98.13154 |
| 498 7 2 | 98.64861 |
| 476 9 3 | 99.02762 |

Example 10

Secondary Screen to Detect the Subset Capable of Blocking RAD51-RAD51 Protein Monomer Association or RAD51-BRC4 Association The 72 inhibitory compounds discussed in Example 9 were subjected to a secondary in vitro screen to identify a sub-set of compounds which function by interrupting RAD51-RAD51 protein monomer association or RAD51-BRC4 association. As discussed earlier, BRC peptides share a conserved motif that is thought to mimic the primary interface used in RAD51 monomer-monomer interactions (Shin et al., 2003; Pellegrini et al., 2002). The minimal BRC4 peptide length sufficient for this interaction has been identified (Example 5) and this peptide has been prepared in fusion to alkaline phosphatase. This BRC4-AP fusion protein binds specifically to polystyrene wells coated with RAD51 (F86E). Note that BRC4 peptide may be preferable over RAD51-based peptides in this assay, because BRC4's binding is stronger than RAD51 fragments in this assay. This was also performed using an AP fusion containing the RAD51 (85-110) fragment shown in FIG. 4.

Each well of a streptavidin-coated 96-well polystyrene plate was incubated with 2.5 µg biotinylated RAD51 (F86E) protein in PBS. Unbound protein was aspirated, and wells blocked with 5% dried milk in PBS. Each peptide-AP fusion protein was diluted in PBS, and 80 µl of each was incubated in a protein-coated well for 60 minutes. Non-binding AP-fusion proteins were aspirated, and wells were washed 3 times with PBS. The levels of well-bound fusion protein were determined by adding 50 µl p-Nitrophenyl Phosphate (PNPP) substrate to each well and incubating at room temperature. Kinetic values of OD405 were measured with a Synergy HT plate reader (Bio-Tek Instruments, Winooski, Vt.), and were normalized to the specific activity of the particular AP-peptide fusion. The 72 inhibitory compounds were tested for the ability to inhibit BRC4-AP binding to RAD51(F86E), resulting in 12 compounds that inhibit binding by at least 30% (Table 4). The 72 compounds were also tested for the ability to inhibit RAD51(85-110)-AP binding to RAD51(F86E), resulting in 6 compounds that inhibit binding by at least 30% (Table 5).

TABLE 4

| Plate location | % inhibition |
| --- | --- |
| 474 11 4 | 40.59041 |
| 486 11 4 | 70.1107 |
| 497 3 5 | 64.20664 |
| 514 7 1 | 46.49446 |
| 522 10 8 | 74.53875 |
| 505 7 6 | 34.68635 |

TABLE 5

| Plate location | % inhibition |
| --- | --- |
| 415 3 5 | 47.99216 |
| 426 5 7 | 43.095 |
| 439 5 3 | 62.2578 |
| 460 6 2 | 38.62369 |
| 474 11 4 | 35.42989 |
| 497 3 5 | 69.92292 |
| 514 7 1 | 46.71464 |
| 518 3 2 | 48.63092 |
| 506 10 7 | 33.46908 |
| 451 2 3 | 51.53983 |
| 505 7 6 | 33.72359 |
| 535 7 1 | 72.91932 |

Example 11

Clonogenic Survival Study Using a RAD51 Enhancer in the Presence of Radiation Single chicken lymphocyte DT40 cells were irradiated. Thirty minutes later, they were incubated with compound 45488 (also called compound 5253121) for 24 hours. Single cells were then plated (100, 1000, or 10000) in 6-well plates in media. Because DT40 cells are not adherent to plastic surfaces, the media included methylcellulose to provide viscosity. After 7-10 days, the resulting colonies are counted, and survival is reported as a colony-forming ability relative to un-irradiated cells.

Figure 12:
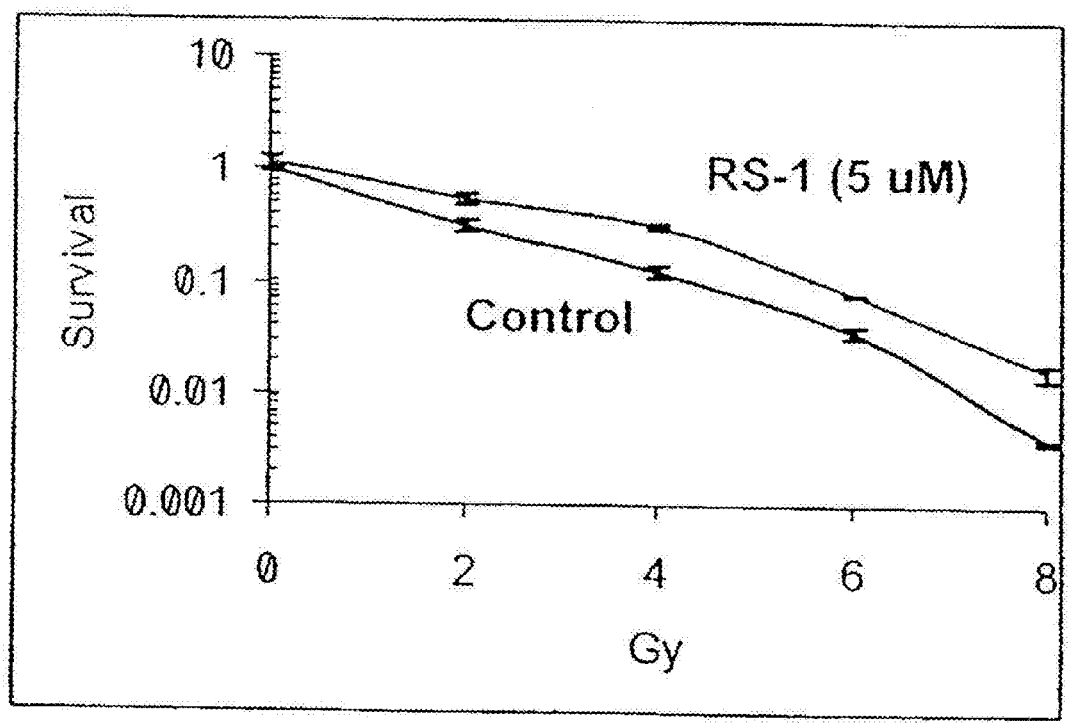
FIG. 12. Clonogenic survival study using a RAD51 enhancer (45488) (also called compound 5253121, or RS-1) in the presence of radiation at various concentrations and chicken DT40 cells.
Figure 13A:
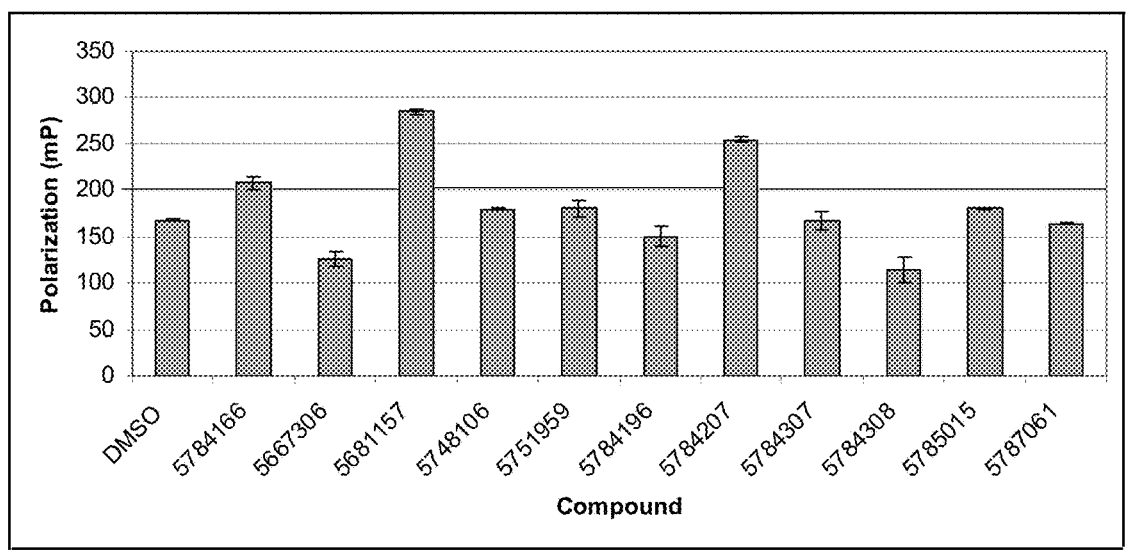
FIGS. 13A-13E. Fluorescence polarization evaluated for a number of compounds to identify RAD51 enhancers.
Figure 13B:
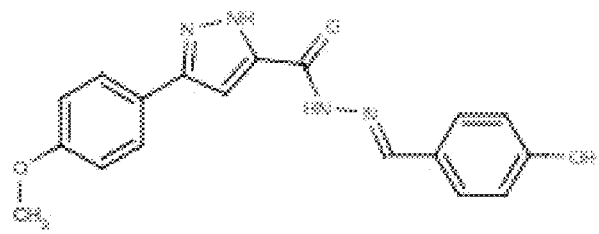
Figure 13B:
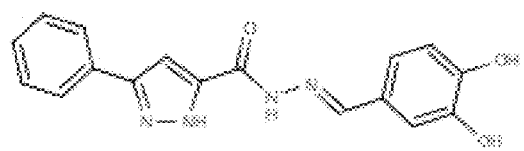
Figure 13B:
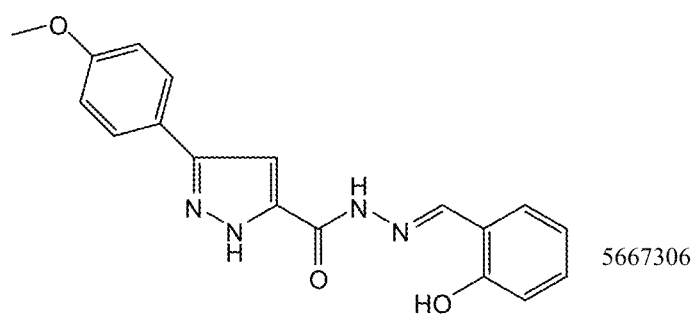
Figure 13C:
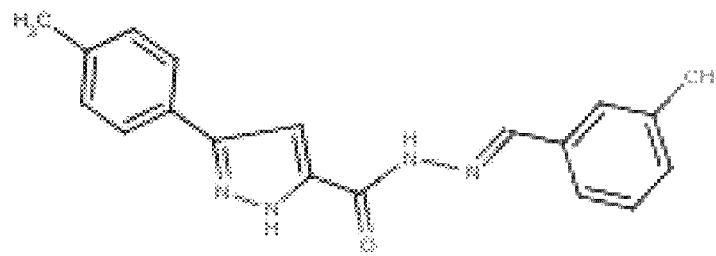
Figure 13C:
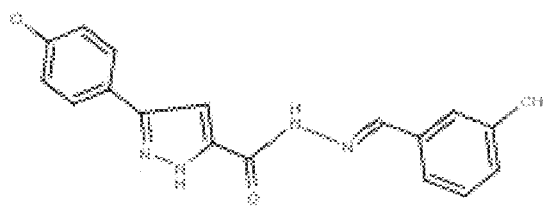
Figure 13C:
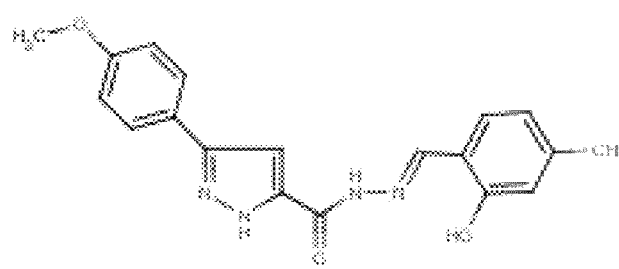
Figure 13D:
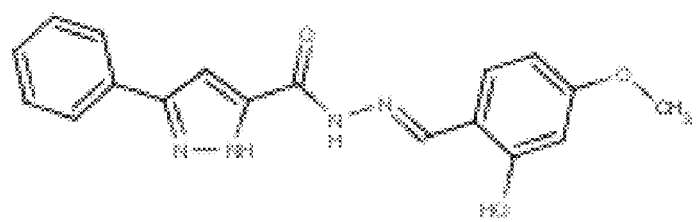
Figure 13D:
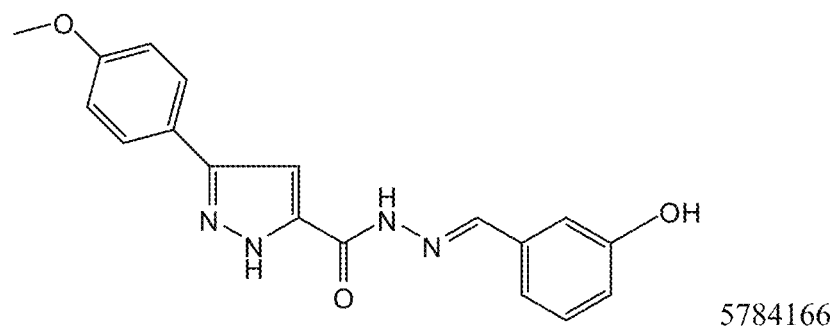
Figure 13D:
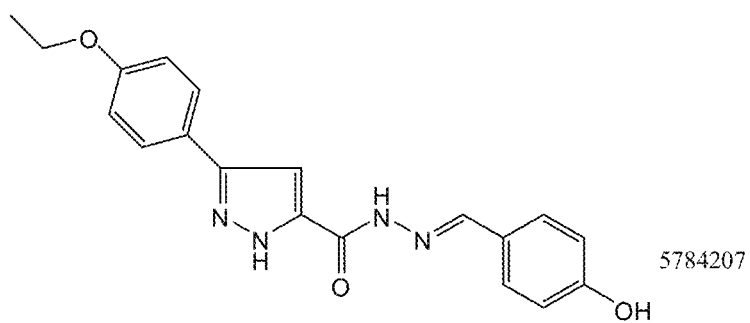
Figure 13E:
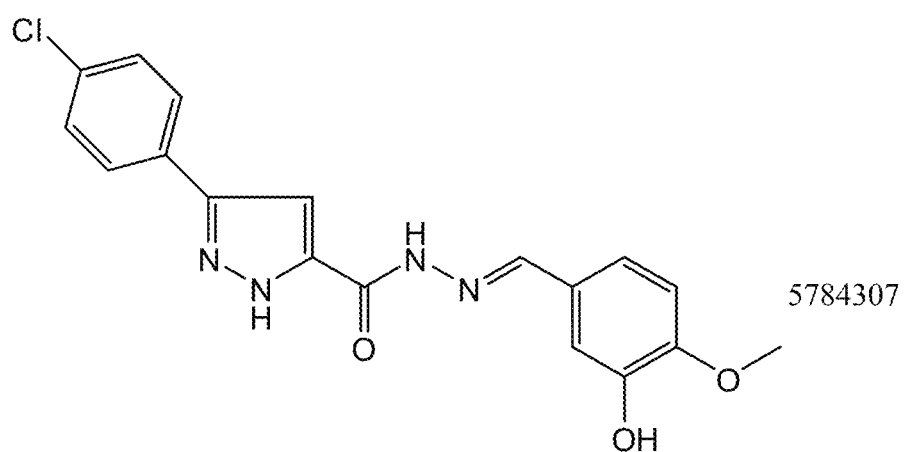
Figure 13E:
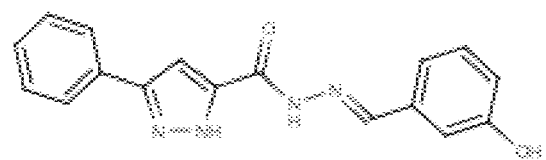
Figure 14A:
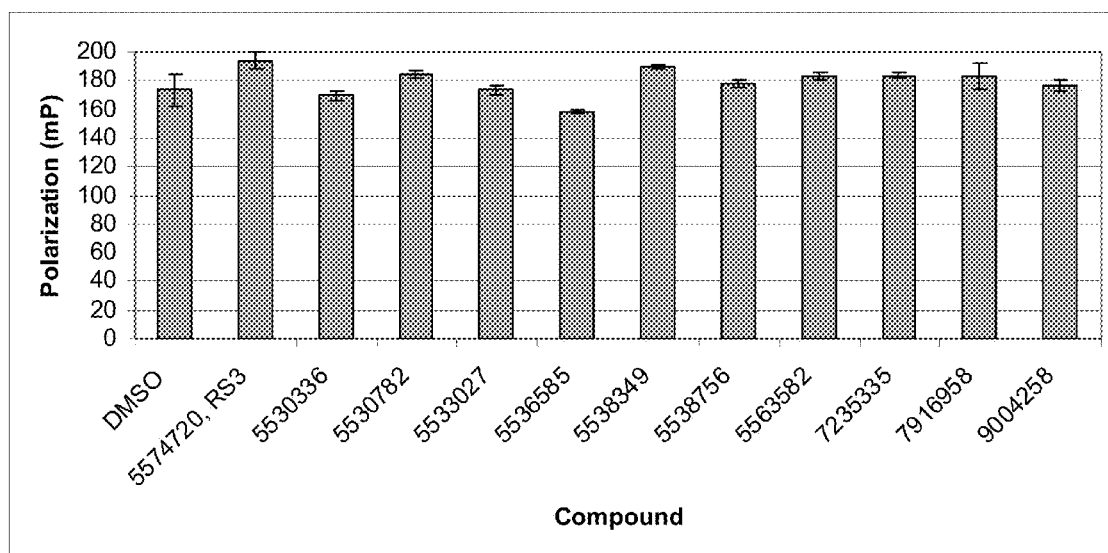
FIGS. 14A-14C. Fluorescence polarization evaluated for a number of compounds to identify RAD51 enhancers.
Figure 14B:
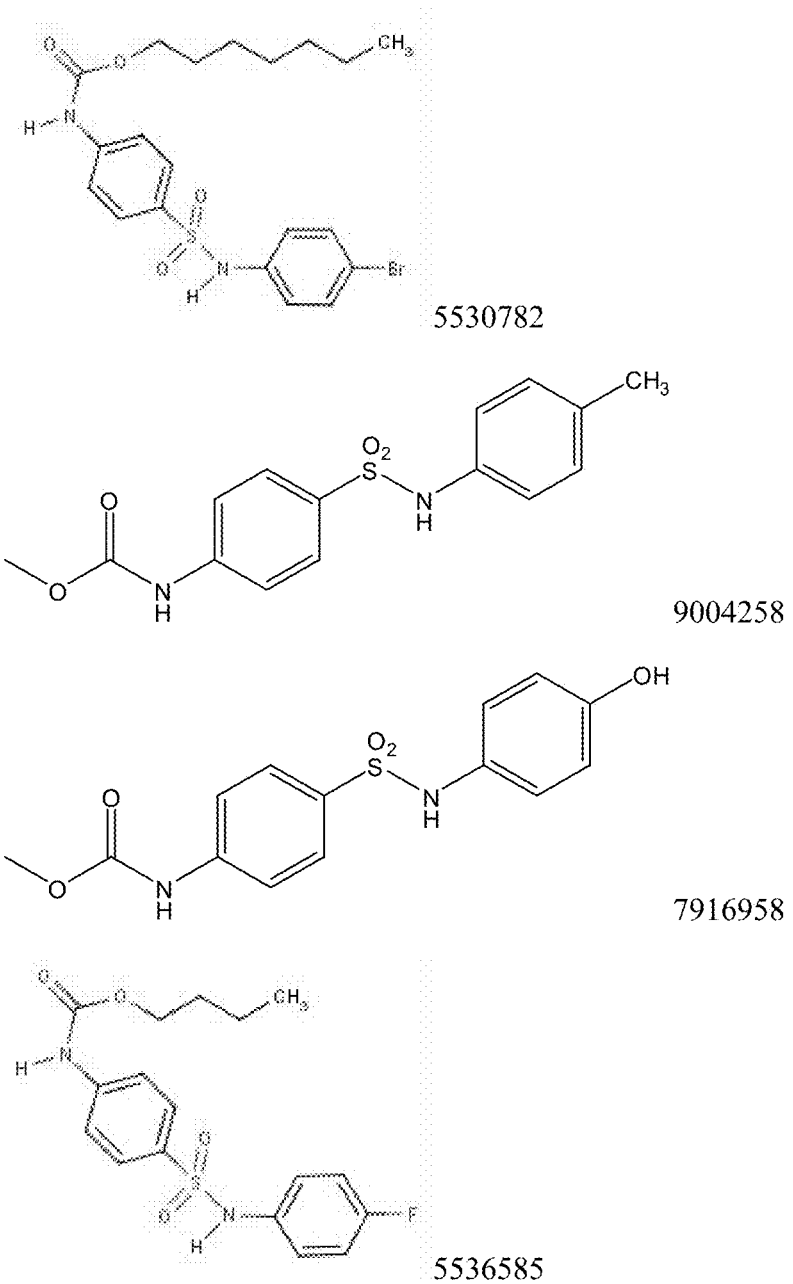
Figure 14C:
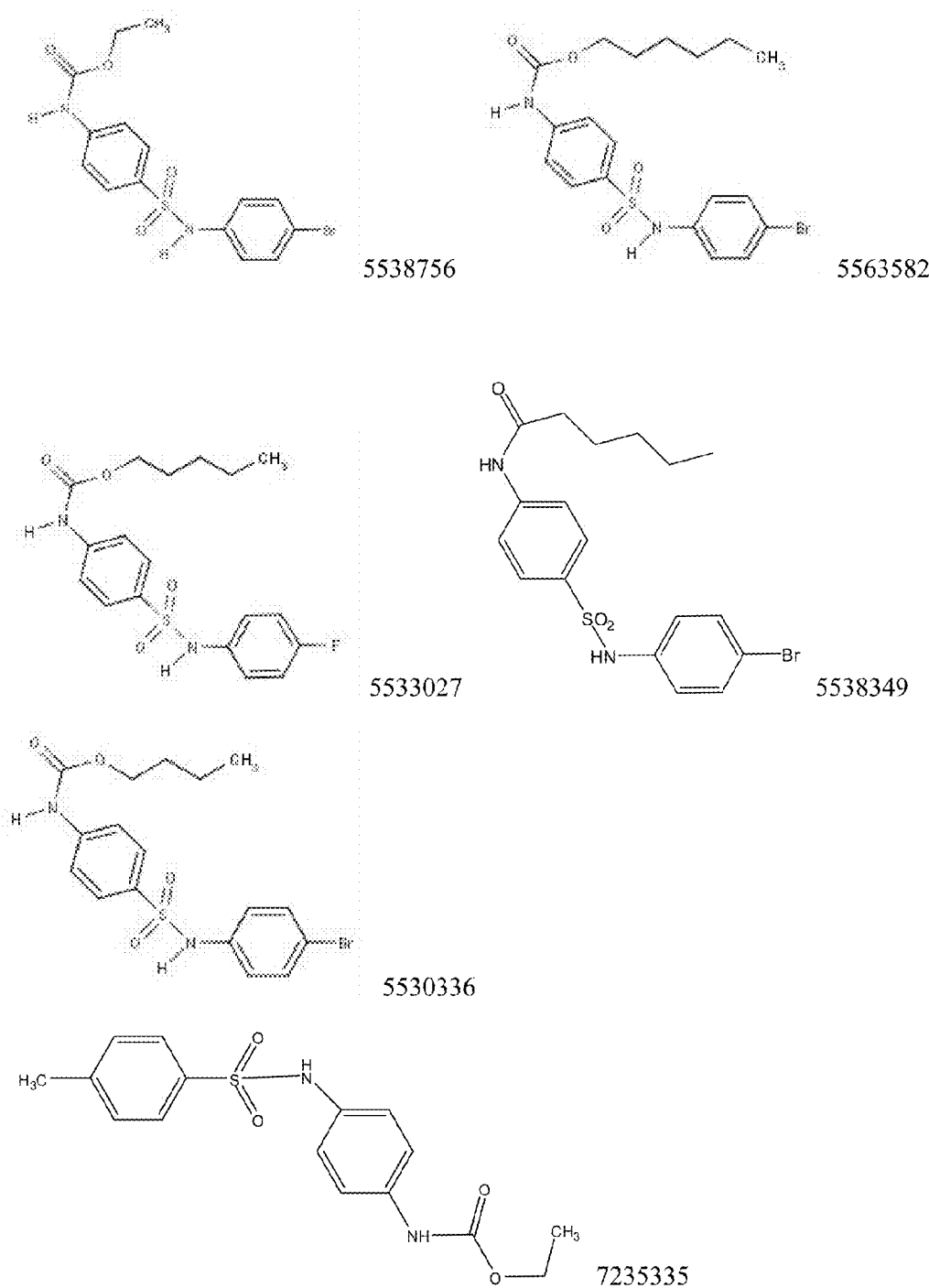

The results, seen in FIG. 12, demonstrate that compound 45488 protects the cells from radiation damage. The compound appears to act as a mitigator of radiation damage (as opposed to a simple protector), because the compound was added to cells about 30 minutes after irradiation of the cells.

Future experiments will entail RAD51 enhancer/radiation clonogenic survival assays in mutant DT40 cells that are deficient in proteins that mediate RAD51 filament assembly at double-strand breaks. If a greater effect of the RAD51 enhancer is observed in these cells (relative to wild type cells), this will provide evidence that the RAD51 enhancer helps cells bypass the requirement of assembly mediators.

Example 12

HR Analysis Using a GFP Recombination Report System

Figure 15A:
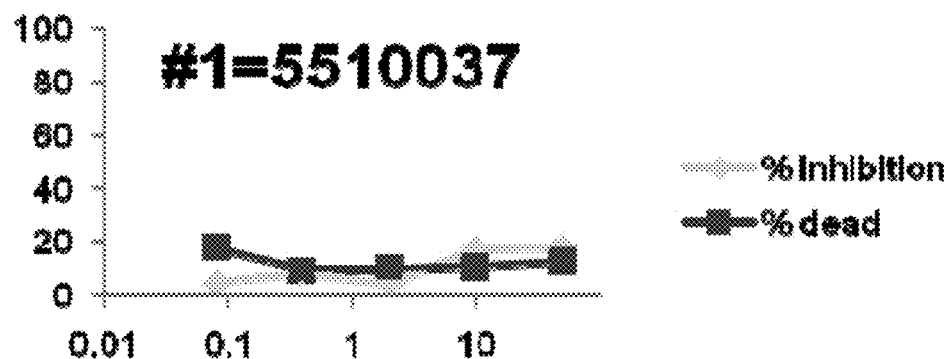
FIGS. 15A-15C. Results of direct repeat GFP recombination reporter system assays as performed with certain RAD51 inhibitors.
Figure 15A:
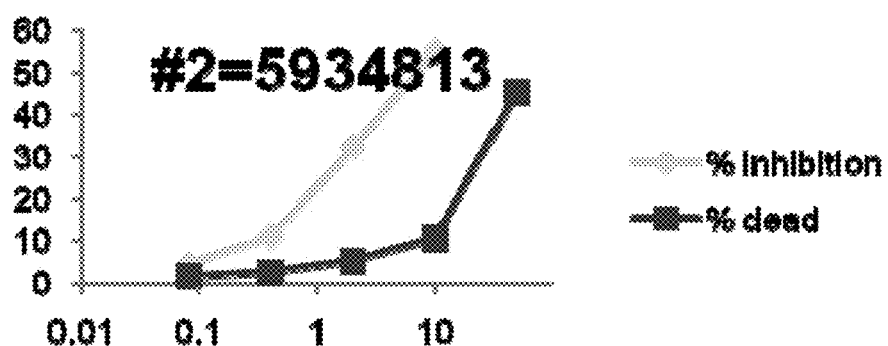
Figure 15A:
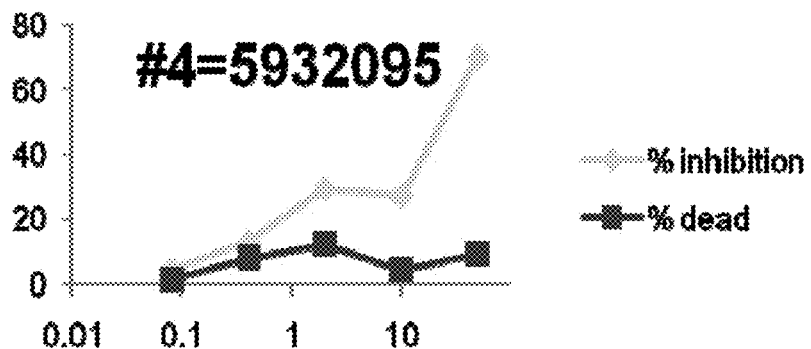
Figure 15B:
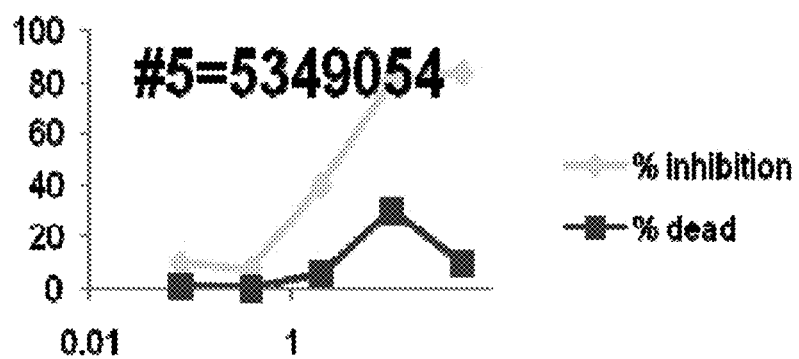
Figure 15B:
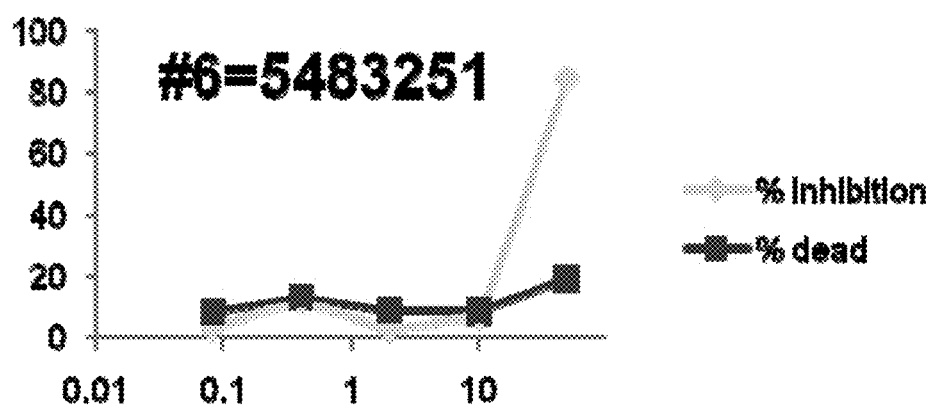
Figure 15B:
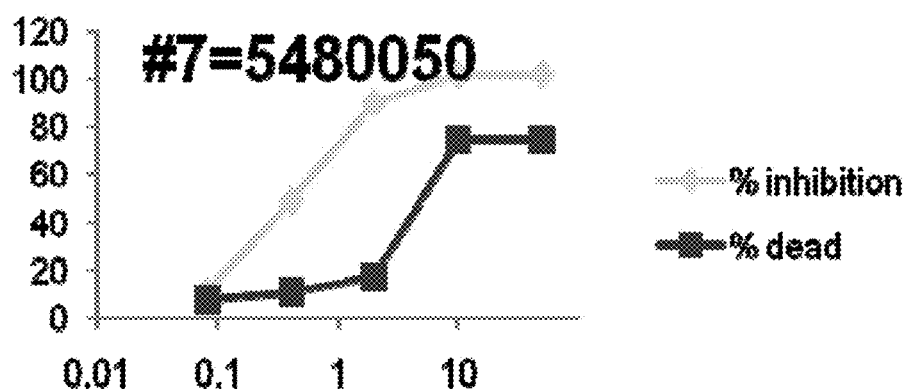
Figure 15C:
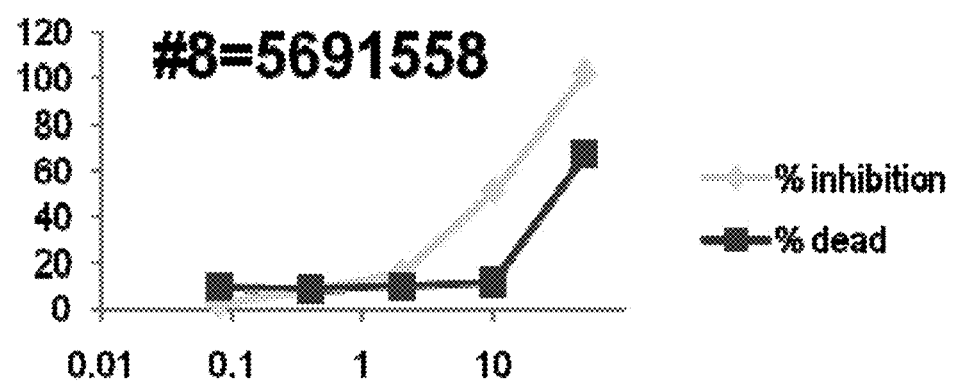
Figure 15C:
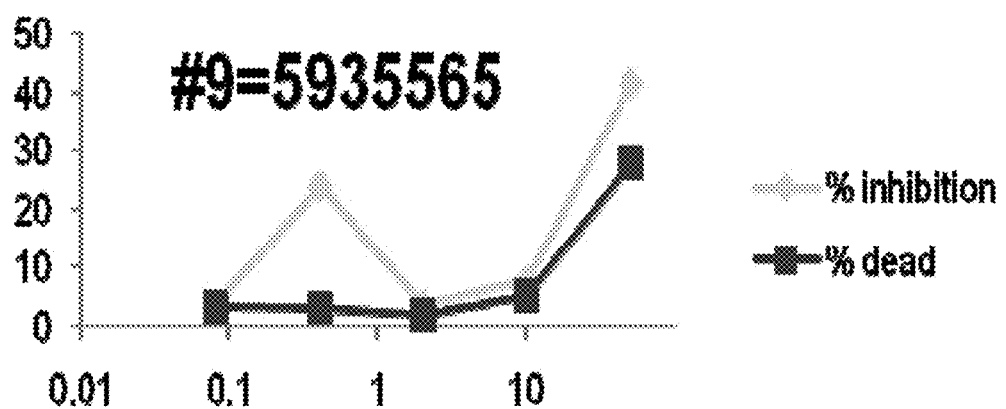
Figure 16:
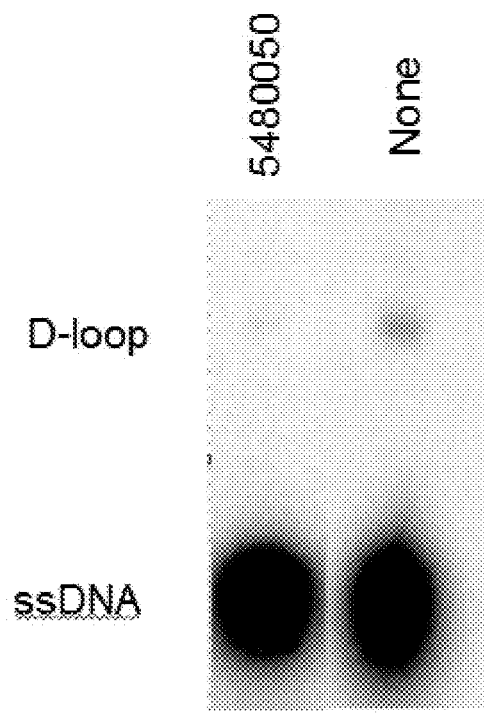
FIG. 16. D-loop assay using an RAD51 inhibitor.

Assay for HR using GFP-based reporter construct: This assay was performed as previously described, with some modifications. Esashi et al., 2005 (incorporated herein by reference in its entirety). U2OS cells containing a single chromosomal copy of the DR-GFP reporter (gift of Maria Jasin, Memorial Sloan Kettering Cancer Center) were transfected with an I-SceI expression vector (pCBASce), which was also a gift of Maria Jasin. Cells were subsequently incubated in media containing candidate compounds (20 µM unless otherwise indicated) for 24 hours, followed by an additional 24 hour incubation in normal media. The percentage of GFP-expressing cells were determined via flow cytometry. Dead cells were excluded by staining with 7-aminoactinomycin D. Results may be seen regarding certain RAD51 inhibitors in FIGS. 15A-15C.

All of the methods and apparatuses disclosed and claimed herein can be made and executed without undue experimentation in light of the present disclosure. While the compositions and methods of this invention have been described in terms of preferred embodiments, it will be apparent to those of skill in the art that variations may be applied to the methods and apparatuses and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,684,611
U.S. Pat. No. 4,873,191
U.S. Pat. No. 4,952,500
U.S. Pat. No. 5,175,384
U.S. Pat. No. 5,175,385
U.S. Pat. No. 5,187,260
U.S. Pat. No. 5,302,523
U.S. Pat. No. 5,322,783
U.S. Pat. No. 5,384,253,
U.S. Pat. No. 5,464,765
U.S. Pat. No. 5,530,179
U.S. Pat. No. 5,538,877
U.S. Pat. No. 5,538,880
U.S. Pat. No. 5,550,318
U.S. Pat. No. 5,563,055
U.S. Pat. No. 5,563,055
U.S. Pat. No. 5,565,186
U.S. Pat. No. 5,580,859
U.S. Pat. No. 5,589,466
U.S. Pat. No. 5,591,616
U.S. Pat. No. 5,610,042
U.S. Pat. No. 5,612,486
U.S. Pat. No. 5,616,491
U.S. Pat. No. 5,625,125
U.S. Pat. No. 5,639,457
U.S. Pat. No. 5,656,610
U.S. Pat. No. 5,702,932
U.S. Pat. No. 5,736,524
U.S. Pat. No. 5,780,448
U.S. Pat. No. 5,789,215,
U.S. Pat. No. 5,945,100
U.S. Pat. No. 5,981,274
U.S. Pat. No. 5,994,624
Alda et al., *Clin. Cancer Res.*, 4:235-240, 1998.
Angel et al., *Cell*, 49:729, 1987a.
Angel et al., *Cell*, 49:729, 1987b.
Atchison and Perry, *Cell*, 46:253, 1986.
Atchison and Perry, *Cell*, 48:121, 1987.
Ausubel et al., In: *Current Protocols in Molecular Biology*, John, Wiley & Sons, Inc, NY, 1994; 1996.
Banerji et al., *Cell*, 27:299, 1981.
Banerji et al., *Cell*, 33(3):729-740, 1983.
Barrio et al., *Biochem. Biophys. Res. Commun.*, 46:597-604, 1972.
Bello et al., *Biochem. Pharmacol.*, 63:1585-1588, 2002.
Berkhout et al., *Cell*, 59:273-282, 1989.
Bishop et al., *J. Biol. Chem.*, 273:21482-21488, 1998.
Blanar et al., *EMBO J.*, 8:1139, 1989.
Bodine and Ley, *EMBO J.*, 6:2997, 1987.
Boshart et al., *Cell*, 41:521, 1985.
Bosze et al., *EMBO J.*, 5(7):1615-1623, 1986.
Braddock et al., *Cell*, 58:269, 1989.
Brinster et al., *Proc. Natl. Acad. Sci. USA*, 82(13):4438-4442, 1985.
Bugreev and Mazin, *Proc. Natl. Acad. Sci. USA*, 101:9988-9993, 2004.
Bulla and Siddiqui, *J. Virol.*, 62:1437, 1986.
Caldecott and Jeggo, *Mutat. Res.*, 255:111-121, 1991.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.

Celander and Haseltine, *J. Virology*, 61:269, 1987.
Celander et al., *J. Virology*, 62:1314, 1988.
Chang et al., *Mol. Cell. Biol.*, 9:2153, 1989.
Chatterjee et al., *Proc. Natl. Acad. Sci. USA*, 86:9114, 1989.
Chen and Okayama, *Mol. Cell Biol.*, 7(8):2745-2752, 1987.
Chen et al., *J. Biol. Chem.*, 274:32931-32935, 1999.
Chen et al., *Proc. Natl. Acad. Sci. USA*, 95:5287-5292, 1998.
Choi et al., *J. Mol. Biol.*, 262(2):151-167, 1996.
Cohen et al., *J. Cell. Physiol.*, 5:75, 1987.
Colli et al., *Nucleic Acids Res.*, 29:1534-1538, 2001.
Connell et al., *Cancer Res.*, 64:3002-3005, 2004.
Costa et al., *Mol. Cell. Biol.*, 8:81-90, 1988.
Cripe et al., *EMBO J.*, 6:3745, 1987.
Cui et al., *Mutat. Res.*, 434:75-88, 1999.
Culotta and Hamer, *Mol. Cell. Biol.*, 9:1376-1380, 1989.
Dandolo et al., *J. Virology*, 47:55-64, 1983.
Davies et al., *Mol. Cell*, 7:273-282, 2001.
Deschamps et al., *Science*, 230:1174-1177, 1985.
Edbrooke et al., *Mol. Cell. Biol.*, 9:1908-1916, 1989.
Edlund et al., *Science*, 230:912-916, 1985.
Ellouze et al., *Eur. J. Biochem.*, 262:88-94, 1999.
Esashi et al., *Nature*, 434:598-604, 2005.
Fechheimer et al., *Proc Natl. Acad. Sci. USA*, 84:8463-8467, 1987.
Feng and Holland, *Nature*, 334:6178, 1988.
Firak and Subramanian, *Mol. Cell. Biol.*, 6:3667, 1986.
Foecking and Hofstetter, *Gene*, 45(1):101-105, 1986.
Fujita et al., *Cell*, 49:357, 1987.
Fuller, and Painter, *Mutat. Res.*, 193:109-121, 1988.
Fung-Leung et al., *Cell*, 65(3):443-449, 1991b.
Fung-Leung et al., *J Exp Med.*, 174(6):1425-1429, 1991a.
Gasior et al., *Proc. Natl. Acad. Sci. USA*, 98:8411-8418, 2001.
Gillies et al., *Cell*, 33:717, 1983.
Gloss et al., *EMBO J.*, 6:3735, 1987.
Godbout et al., *Mol. Cell. Biol.*, 8:1169, 1988.
Godthelp et al., *Nucleic Acids Res.*, 30:2172-2182, 2002.
Goodbourn and Maniatis, *Cell*, 41(2):509-520, 1985.
Goodbourn et al., *Cell*, 45:601, 1986.
Gopal, *Mol. Cell Biol.*, 5:1188-1190, 1985.
Graham and Van Der Eb, *Virology*, 52:456-467, 1973.
Greene et al., *Immunology Today*, 10:272, 1989.
Grosschedl and Baltimore, *Cell*, 41:885, 1985.
Han et al., *Cancer Res.*, 62:2890-2896, 2002.
Han et al., *Comb. Chem. High Throughput Screen*, 7:55-62, 2004.
*Handbook of Pharmaceutical Salts: Properties, Selection and Use*, Stahl & Wermuth (Eds.), Verlag Helvetica Chimica Acta, 2002.
Hansen et al., *Int. J. Cancer*, 105:472-479, 2003.
Harland and Weintraub, *J. Cell Biol.*, 101(3):1094-1099, 1985.
Haslinger and Karin, *Proc. Nat'l Acad. Sci. USA.*, 82:8572, 1985.
Hauber and Cullen, *J. Virology*, 62:673, 1988.
Hen et al., *Nature*, 321:249, 1986.
Henning and Sturzbecher, *Toxicology*, 193:91-109, 2003.
Hensel et al., *Lymphokine Res.*, 8:347, 1989.
Herr and Clarke, *Cell*, 45:461, 1986.
Hirochika et al., *J. Virol.*, 61:2599, 1987.
Hirsch et al., *Mol. Cell. Biol.*, 10:1959, 1990.
Holbrook et al., *Virology*, 157:211, 1987.
Horlick and Benfield, *Mol. Cell. Biol.*, 9:2396, 1989.
Huang et al., *Cell*, 27:245, 1981.
Hug et al., *Mol. Cell. Biol.*, 8:3065-3079, 1988.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Inouye and Inouye, *Nucleic Acids Res.*, 13:3101-3109, 1985.
Ito et al., *J. Gene Med.*, 7(8):1044-1052, 2005.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson et al., *Mol. Cell. Biol.*, 9(8):3393-3399, 1989.
Kadesch and Berg, *Mol. Cell. Biol.*, 6:2593, 1986.
Kaeppler et al., *Plant Cell Reports*, 9:415-418, 1990.
Kaneda et al., *Science*, 243:375-378, 1989.
Karin et al., *Mol. Cell. Biol.*, 7:606, 1987.
Karin et al., *Mol. Cell. Biol.*, 7:606, 1987.
Katinka et al., *Cell*, 20:393, 1980.
Katinka et al., *Nature*, 290:720, 1981.
Kato et al, *J. Biol. Chem.*, 266:3361-3364, 1991.
Kawamoto et al., *Mol. Cell. Biol.*, 8:267, 1988.
Kiledjian et al., *Mol. Cell. Biol.*, 8:145, 1988.
Kim et al., *J. Biochem. (Tokyo)*, 129:469-475, 2001.
Klamut et al., *Mol. Cell. Biol.*, 10:193, 1990.
Koch et al., *Mol. Cell. Biol.*, 9:303, 1989.
Kriegler and Botchan, *Mol. Cell. Biol.*, 3:325, 1983.
Kriegler et al., *Cell*, 38:483, 1984a.
Kriegler et al., In: *Cancer Cells 2/Oncogenes and Viral Genes*, Van de Woude et al. eds, Cold Spring Harbor, Cold Spring Harbor Laboratory, 1984b.
Krzyzosiak et al., *Nucleic Acids Res.*, 9:2841-2851, 1981.
Kuhl et al., *Cell*, 50:1057, 1987.
Kunz et al., *Nucl. Acids Res.*, 17:1121, 1989.
Larsen et al., *Proc. Natl. Acad. Sci. USA.*, 83:8283, 1986.
Laspia et al., *Cell*, 59:283, 1989.
Latimer et al., *Mol. Cell. Biol.*, 10:760, 1990.
Lee et al., *Nature*, 294:228, 1981.
Lee et al., *Nucleic Acids Res.*, 12:4191-206, 1984.
Lin et al., *Mol. Cell. Biol.*, 10:850, 1990.
Liu et al., *Mol. Cell*, 1:783-793, 1998.
Liu et al., *Nucleic Acids Res.*, 30:1009-1015, 2002.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Maacke et al., *Int. J. Cancer*, 88:907-913, 2000a.
Maacke et al., *J. Cancer Res. Clin. Oncol.*, 128:219-222, 2002.
Maacke et al., *Oncogene*, 19:2791-2795, 2000b.
Macejak and Sarnow, *Nature*, 353:90-94, 1991.
Majors and Varmus, *Proc. Natl. Acad. Sci. USA.*, 80:5866, 1983.
*Manipulating the Mouse Embryo; A Laboratory Manual* 2nd edition (eds., Hogan, Beddington, Costantimi and Long, Cold Spring Harbor Laboratory Press, 1994.
Marcus et. al., *Cancer*, 77(4):697-670, 1996.
Masson et al., *Genes Dev.*, 15:3296-3307, 2001.
Masson et al., *Proc. Natl. Acad. Sci. USA*, 98:8440-8446, 2001.
McNeall et al., *Gene*, 76:81, 1989.
Menetski and Kowalczykowski, *J. Mol. Biol.*, 181:281-295, 1985.
Miksicek et al., *Cell*, 46:203, 1986.
Mordacq and Linzer, *Genes and Dev.*, 3:760, 1989.
Moreau et al., *Nucl. Acids Res.*, 9:6047, 1981.
Moynahan et al., *Mol. Cell*, 7:263-272, 2001.
Muesing et al., *Cell*, 48:691, 1987.
Neuberger et al., *Nucleic Acids Res.*, 16(14B):6713-6724, 1988.
Ng et al., *Nuc. Acids Res.*, 17:601, 1989.

Nicolau and Sene, *Biochim. Biophys. Acta,* 721:185-190, 1982.
Nicolau et al., *Methods Enzymol.,* 149:157-176, 1987.
Ohnishi et al., *Biochem. Biophys. Res. Commun.,* 245:319-324, 1998.
Omirulleh et al., *Plant Mol. Biol.,* 21(3):415-428, 1993.
Omitz et al., *Mol. Cell. Biol.* 7:3466, 1987.
Ondek et al., *EMBO J.,* 6:1017, 1987.
Palmiter et al., *Cell,* 29:701, 1982.
PCT Appln. WO 94/09699
PCT Appln. WO 95/06128
Pech et al., *Mol. Cell. Biol.,* 9:396, 1989.
Pellegrini et al., *Nature,* 420:287-293, 2002.
Pelletier and Sonenberg, *Nature,* 334(6180):320-325, 1988.
Perez-Stable and Constantini, *Mol. Cell. Biol.,* 10:1116, 1990.
Pfeffer et al., *Cell,* 73(3):457-467, 1993.
Picard and Schaffner, *Nature,* 307:83, 1984.
Pinkert et al., *Genes and Dev.,* 1:268, 1987.
Ponta et al., *Proc. Natl. Acad. Sci. USA.,* 82:1020, 1985.
Porter et al., *Br. J. Surg.,* 81:1512-1515, 1994.
Potrykus et al., *Mol. Gen. Genet.,* 199:183-188, 1985.
Qiao et al., *Br. J. Cancer,* 93:137-143, 2005.
Queen and Baltimore, *Cell,* 35:741, 1983.
Quinn et al., *Mol. Cell. Biol.,* 9:4713, 1989.
Raderschall et al., *Cancer Res.,* 62:219-225, 2002.
Redondo et al., *Science,* 247:1225, 1990.
Reisman and Rotter, *Mol. Cell. Biol.,* 9:3571, 1989.
Remington's Pharmaceutical Sciences, 18th Ed. Mack Printing Company, 1289-1329, 1990.
Remington's Pharmaceutical Sciences, 18th Ed. Mack Printing Company, pp. 1289-1329, 1990.
Resendez Jr. et al., *Mol. Cell. Biol.,* 8:4579, 1988.
Rippe et al., *Mol. Cell. Biol.,* 9(5):2224-22277, 1989.
Rippe, et al., *Mol. Cell Biol.,* 10:689-695, 1990.
Rittling et al., *Nucl. Acids Res.,* 17:1619, 1989.
Rubin et al., *N. Engl. J. Med.,* 335:1413-1416, 1996.
Russell et al., *Cancer Res.,* 63:7377-7383, 2003.
Sambrook and Russell, Molecular Cloning: A Laboratory Manual 3rd Ed., Cold Spring Harbor Laboratory Press, 2001.
Schaffner et al., *J. Mol. Biol.,* 201:81, 1988.
Searle et al., *Mol. Cell. Biol.,* 5:1480, 1985.
Secrist et al., *Biochemistry,* 11:3499-3506, 1972.
Sharp and Marciniak, *Cell,* 59:229, 1989.
Shaul and Ben-Levy, *EMBO J.,* 6:1913, 1987.
Sherman et al., *Mol. Cell. Biol.,* 9:50, 1989.
Shin et al., *Embo. J.,* 22:4566-4576, 2003.
Shinohara et al., *Cell,* 69:457-470, 1992.
Sleigh and Lockett, *J. EMBO,* 4:3831, 1985.
Slupianek et al., *Mol. Cell Biol.,* 22:4189-4201, 2002.
Slupianek et al., *Mol. Cell,* 8:795-806, 2001.
Spalholz et al., *Cell,* 42:183, 1985.
Spandau and Lee, *J. Virology,* 62:427, 1988.
Spandidos and Wilkie, *EMBO J.,* 2:1193, 1983.
Stephens and Hentschel, *Biochem. J.,* 248:1, 1987.
Stuart et al., *Nature,* 317:828, 1985.
Sugiyama et al., *J. Biol. Chem.,* 272:7940-7945, 1997.
Sullivan and Peterlin, *Mol. Cell. Biol.,* 7:3315, 1987.
Swartzendruber and Lehman, *J. Cell. Physiology,* 85:179, 1975.
Takata et al., *Mol. Cell Biol.,* 21:2858-2866, 2001.
Takebe et al., *Mol. Cell. Biol.,* 8:466, 1988.
Tavernier et al., *Nature,* 301:634, 1983.
Taylor and Kingston, *Mol. Cell. Biol.,* 10:165, 1990a.
Taylor and Kingston, *Mol. Cell. Biol.,* 10:176, 1990b.
Taylor et al., *J. Biol. Chem.,* 264:15160, 1989.
Tebbs et al., *Proc. Natl. Acad. Sci. USA,* 92:6354-6358, 1995.
Thiesen et al., *J. Virology,* 62:614, 1988.
Thompson and Schild, *Biochimie.,* 81:87-105, 1999.
Thompson and Schild, *Mutat. Res.,* 477:131-153, 2001.
Treisman, *Cell,* 42:889, 1985.
Tronche et al., *Mol. Biol. Med.,* 7:173, 1990.
Tronche et al., *Mol. Cell. Biol.,* 9:4759, 1989.
Trudel and Constantini, *Genes and Dev.,* 6:954, 1987.
Tyndall et al., *Nuc. Acids. Res.,* 9:6231, 1981.
Vasseur et al., *Proc. Natl. Acad. Sci. USA.,* 77:1068, 1980.
Vispe et al., *Nucleic Acids Res.,* 26:2859-2864, 1998.
Wang and Calame, *Cell,* 47:241, 1986.
Wang et al., *J. Natl. Cancer Inst.,* 93:1473-1478, 2001.
Weber et al., *Cell,* 36:983, 1984.
Wiese et al., *Nucleic Acids Res.,* 30:1001-1008, 2002.
Winoto and Baltimore, *Cell,* 59:649, 1989.
Wittung et al., *Eur. J. Biochem.,* 245:715-719, 1997.
Wong et al., *Gene,* 10:87-94, 1980.
Wong et al., *J. Biol. Chem.,* 272:31941-31944, 1997.
Yoshikawa et al., *Int. J. Cancer,* 88:28-36, 2000.
Yu et al., *Mol. Cell,* 12:1029-1041, 2003.
Yuan et al., *Cancer Res.,* 59:3547-3551, 1999.
Yutzey et al. *Mol. Cell. Biol.,* 9:1397, 1989.
Zaitseva et al., *J. Biol. Chem.,* 274:2907-2915, 1999.
Zhang et al., *J. Biomol. Screen,* 4:67-73, 1999.

SEQUENCE LISTING

```
<160> NUMBER OF SEQ ID NOS: 16

<210> SEQ ID NO 1
<211> LENGTH: 69
<212> TYPE: PRT
<213> ORGANISM: Homo sapiens

<400> SEQUENCE: 1

Glu Arg Asp Glu Lys Ile Lys Glu Pro Thr Leu Leu Gly Phe His Thr
1               5                   10                  15

Ala Ser Gly Lys Lys Val Lys Ile Ala Lys Glu Ser Leu Asp Lys Val
            20                  25                  30

Lys Asn Leu Phe Asp Glu Lys Glu Gln Gly Thr Ser Glu Ile Thr Ser
        35                  40                  45

Phe Ser His Gln Trp Ala Lys Thr Leu Lys Tyr Arg Glu Ala Cys Lys
    50                  55                  60
```

```
Asp Leu Glu Leu Ala
 65

<210> SEQ ID NO 2
<211> LENGTH: 69
<212> TYPE: PRT
<213> ORGANISM: Artificial
<220> FEATURE:
<223> OTHER INFORMATION: Synthetic peptide

<400> SEQUENCE: 2

Glu Arg Asp Glu Lys Ile Lys Glu Pro Thr Leu Leu Gly Phe His Ala
 1               5                  10                  15

Ala Ser Gly Lys Lys Val Lys Ile Ala Lys Glu Ser Leu Asp Lys Val
                 20                  25                  30

Lys Asn Leu Phe Asp Glu Lys Glu Gln Gly Thr Ser Glu Ile Thr Ser
             35                  40                  45

Phe Ser His Gln Trp Ala Lys Thr Leu Lys Tyr Arg Glu Ala Cys Lys
 50                  55                  60

Asp Leu Glu Leu Ala
 65

<210> SEQ ID NO 3
<211> LENGTH: 37
<212> TYPE: PRT
<213> ORGANISM: Homo sapiens

<400> SEQUENCE: 3

Glu Arg Asp Glu Lys Ile Lys Glu Pro Thr Leu Leu Gly Phe His Thr
 1               5                  10                  15

Ala Ser Gly Lys Lys Val Lys Ile Ala Lys Glu Ser Leu Asp Lys Val
                 20                  25                  30

Lys Asn Leu Phe Asp
             35

<210> SEQ ID NO 4
<211> LENGTH: 25
<212> TYPE: PRT
<213> ORGANISM: Homo sapiens

<400> SEQUENCE: 4

Glu Arg Asp Glu Lys Ile Lys Glu Pro Thr Leu Leu Gly Phe His Thr
 1               5                  10                  15

Ala Ser Gly Lys Lys Val Lys Ile Ala
                 20                  25

<210> SEQ ID NO 5
<211> LENGTH: 61
<212> TYPE: PRT
<213> ORGANISM: Homo sapiens

<400> SEQUENCE: 5

Pro Thr Leu Leu Gly Phe His Thr Ala Ser Gly Lys Lys Val Lys Ile
 1               5                  10                  15

Ala Lys Glu Ser Leu Asp Lys Val Lys Asn Leu Phe Asp Glu Lys Glu
                 20                  25                  30

Gln Gly Thr Ser Glu Ile Thr Ser Phe Ser His Gln Trp Ala Lys Thr
             35                  40                  45

Leu Lys Tyr Arg Glu Ala Cys Lys Asp Leu Glu Leu Ala
 50                  55                  60
```

```
<210> SEQ ID NO 6
<211> LENGTH: 29
<212> TYPE: PRT
<213> ORGANISM: Homo sapiens

<400> SEQUENCE: 6

Pro Thr Leu Leu Gly Phe His Thr Ala Ser Gly Lys Lys Val Lys Ile
1               5                   10                  15

Ala Lys Glu Ser Leu Asp Lys Val Lys Asn Leu Phe Asp
            20                  25

<210> SEQ ID NO 7
<211> LENGTH: 26
<212> TYPE: PRT
<213> ORGANISM: Homo sapiens

<400> SEQUENCE: 7

Pro Thr Leu Leu Gly Phe His Thr Ala Ser Gly Lys Lys Val Lys Ile
1               5                   10                  15

Ala Lys Glu Ser Leu Asp Lys Val Lys Asn
            20                  25

<210> SEQ ID NO 8
<211> LENGTH: 23
<212> TYPE: PRT
<213> ORGANISM: Homo sapiens

<400> SEQUENCE: 8

Pro Thr Leu Leu Gly Phe His Thr Ala Ser Gly Lys Lys Val Lys Ile
1               5                   10                  15

Ala Lys Glu Ser Leu Asp Lys
            20

<210> SEQ ID NO 9
<211> LENGTH: 21
<212> TYPE: PRT
<213> ORGANISM: Homo sapiens

<400> SEQUENCE: 9

Pro Thr Leu Leu Gly Phe His Thr Ala Ser Gly Lys Lys Val Lys Ile
1               5                   10                  15

Ala Lys Glu Ser Leu
            20

<210> SEQ ID NO 10
<211> LENGTH: 17
<212> TYPE: PRT
<213> ORGANISM: Homo sapiens

<400> SEQUENCE: 10

Pro Thr Leu Leu Gly Phe His Thr Ala Ser Gly Lys Lys Val Lys Ile
1               5                   10                  15

Ala

<210> SEQ ID NO 11
<211> LENGTH: 25
<212> TYPE: PRT
<213> ORGANISM: Homo sapiens

<400> SEQUENCE: 11

Gly Phe His Thr Ala Ser Gly Lys Lys Val Lys Ile Ala Lys Glu Ser
```

```
                 1               5                  10                  15
Leu Asp Lys Val Lys Asn Leu Phe Asp
             20                  25

<210> SEQ ID NO 12
<211> LENGTH: 25
<212> TYPE: PRT
<213> ORGANISM: Artificial
<220> FEATURE:
<223> OTHER INFORMATION: Synthetic peptide

<400> SEQUENCE: 12

Gly Phe His Ala Ala Ser Gly Lys Lys Val Lys Ile Ala Lys Glu Ser
 1               5                  10                  15
Leu Asp Lys Val Lys Asn Leu Phe Asp
             20                  25

<210> SEQ ID NO 13
<211> LENGTH: 25
<212> TYPE: PRT
<213> ORGANISM: Artificial
<220> FEATURE:
<223> OTHER INFORMATION: Synthetic peptide

<400> SEQUENCE: 13

Gly Glu His Thr Ala Ser Gly Lys Lys Val Lys Ile Ala Lys Glu Ser
 1               5                  10                  15
Leu Asp Lys Val Lys Asn Leu Phe Asp
             20                  25

<210> SEQ ID NO 14
<211> LENGTH: 25
<212> TYPE: PRT
<213> ORGANISM: Artificial
<220> FEATURE:
<223> OTHER INFORMATION: Synthetic peptide

<400> SEQUENCE: 14

Gly Glu His Ala Ala Ser Gly Lys Lys Val Lys Ile Ala Lys Glu Ser
 1               5                  10                  15
Leu Asp Lys Val Lys Asn Leu Phe Asp
             20                  25

<210> SEQ ID NO 15
<211> LENGTH: 26
<212> TYPE: PRT
<213> ORGANISM: Homo sapiens

<400> SEQUENCE: 15

Gly Phe Thr Thr Ala Thr Glu Phe His Gln Arg Arg Ser Glu Ile Ile
 1               5                  10                  15
Gln Ile Thr Thr Gly Ser Lys Glu Leu Asp
             20                  25

<210> SEQ ID NO 16
<211> LENGTH: 26
<212> TYPE: PRT
<213> ORGANISM: Artificial
<220> FEATURE:
<223> OTHER INFORMATION: Synthetic peptide

<400> SEQUENCE: 16
```

```
Gly Glu Thr Thr Ala Thr Glu Phe His Gln Arg Arg Ser Glu Ile Ile
1               5                   10                  15

Gln Ile Thr Thr Gly Ser Lys Glu Leu Asp
                20              25
```

Figure 9I:
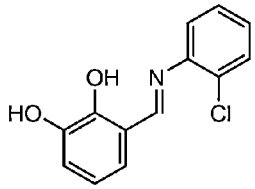
Figure 9I:
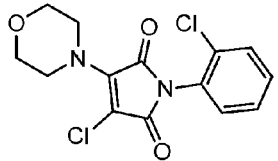
Figure 9I:
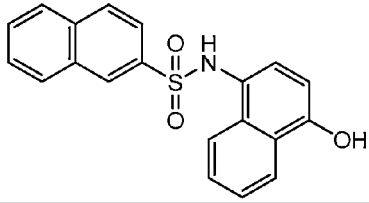
Figure 9I:
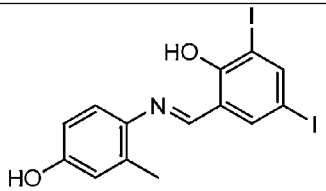
Figure 9I:
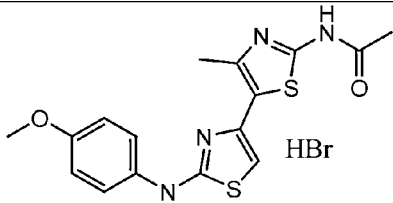
Figure 9I:
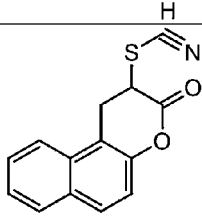
Figure 9I:
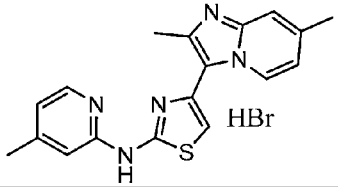
Figure 9K:
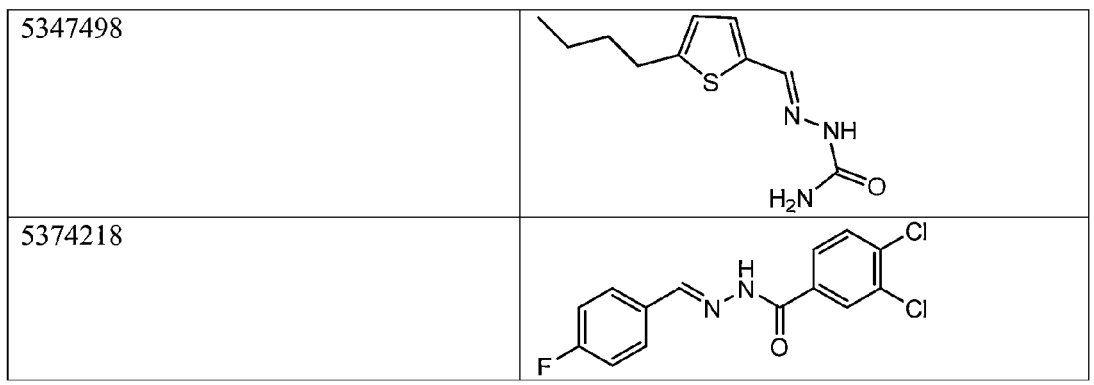
Figure 9K:
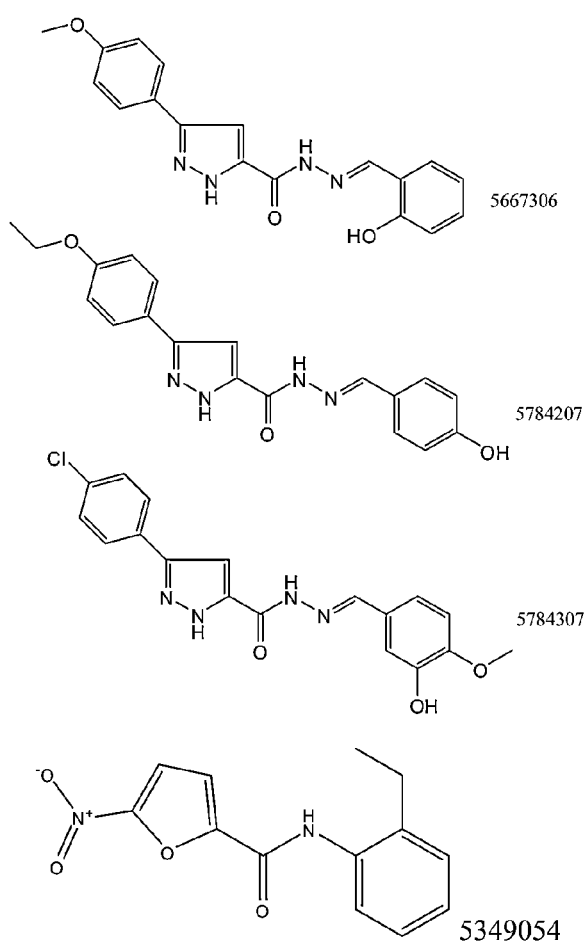

The invention claimed is:

1. A method for inhibiting a RAD51 protein in a cell comprising providing to the cell an effective amount of a small molecule that inhibits the activity of RAD51 protein, wherein the small molecule is compound 5349669, 5344003, 5354404, or 5353472 shown in FIGS. 9H-9I, or a salt thereof.

2. The method of claim 1, wherein the RAD51 inhibitor decreases RAD51 filament formation.

3. The method of claim 1, wherein the RAD51 inhibitor does not interact with a RAD51 DNA binding domain.

4. The method of claim 1, wherein the RAD51 inhibitor interferes with RAD51 ATPase activity.

5. The method of claim 1, wherein the RAD51 inhibitor is not a nucleotide diphosphate, a nucleotide analog, a DNA minor groove binding drug, a xanthine, or xanthine derivative.

6. The method of claim 1, wherein the cell is a cancer cell.

7. The method of claim 6, wherein the cancer cell is resistant to chemotherapy or radiation.

8. The method of claim 6, wherein the cancer cell is a cell of the lung, liver, skin, eye, brain, gum, tongue, hematopoietic system or blood, head, neck, breast, pancreas, prostate, kidney, bone, testicles, ovary, cervix, gastrointestinal tract, lymph system, small intestine, colon, or bladder.

9. The method of claim 1, wherein the cell is chemotherapy- or radiation-resistant.

10. The method of claim 9, wherein the cancer cell is resistant to a DNA damaging agent.

11. The method of claim 10, wherein the DNA damaging agent is an alkylating agent, nitrosourea, anti-metabolite, plant alkaloid, plant extract, or radioisotope.

12. The method of claim 10, wherein the DNA damaging agent is radiation.

13. The method of claim 11, wherein the DNA damaging agent is actinomycin, amsacrine, anthracyclines, bleomycin, busulfan, camptothecin, carboplatin, chlorambucil, cisplatin, cyclophosphamide, cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide or etoposide (VP16).

14. The method of claim 1, wherein the RAD51 protein inhibitor is administered to the cells of a patient intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularly, mucosally, intrapericardially, intraumbilically, intraocularally, orally, topically, locally, by inhalation, by injection, by infusion, by continuous infusion, by localized perfusion bathing target cells directly, via a catheter, or via a lavage.

15. The method of claim 1, wherein the RAD51 protein inhibitor is provided to the cell multiple times.

16. The method of claim 1, wherein the RAD51 inhibitor is compound 5349669 shown in FIG. 9H.

17. A method for inhibiting RAD51 in cancer cells of a cancer patient comprising administering to the cancer patient an effective amount of a RAD51 small molecule that directly inhibits RAD51 activity in a cell, wherein the RAD51 small molecule inhibitor is a compound 5349669, 5344003, 5354404, or 5353472 shown in FIGS. 9H-9I, or a salt thereof.

18. The method of claim 17, further comprising administering to the cancer patient chemotherapy or radiation.

19. The method of claim 17, wherein the RAD51 inhibitor is compound 5349669 shown in FIG. 9H.

20. A method for inhibiting RAD51 in cancer cells of a subject comprising providing to the subject an effective amount of a composition comprising compound 5349669 shown in FIG. 9H, or a salt thereof.

* * * * *

UNITED STATES PATENT AND TRADEMARK OFFICE
CERTIFICATE OF CORRECTION

PATENT NO. : 9,198,914 B2  
APPLICATION NO. : 14/074395  
DATED : December 1, 2015  
INVENTOR(S) : Philip P. Connell et al.

Page 1 of 1

It is certified that error appears in the above-identified patent and that said Letters Patent is hereby corrected as shown below:

On the title page in item (60), "Jul. 30, 2007" should read --Jul. 28, 2007--.

Signed and Sealed this  
Twenty-ninth Day of March, 2016

Michelle K. Lee  
*Director of the United States Patent and Trademark Office*